United States Patent
Sugano et al.

(10) Patent No.: US 6,825,371 B2
(45) Date of Patent: Nov. 30, 2004

(54) CATALYSTS FOR POLYMERIZATION OF α-OLEFINS, PROCESS FOR PRODUCING α-OLEFIN POLYMERS, NOVEL TRANSITION METAL COMPOUNDS AND CATALYST COMPONENTS FOR POLYMERIZATION OF α-OLEFIN

(75) Inventors: Toshihiko Sugano, Yokohama (JP); Masami Kashimoto, Yokohama (JP); Taku Kato, Yokohama (JP)

(73) Assignee: Mitsubishi Chemical Corporation (JP)

( * ) Notice: Subject to any disclaimer, the term of this patent is extended or adjusted under 35 U.S.C. 154(b) by 72 days.

(21) Appl. No.: 10/308,096

(22) Filed: Dec. 3, 2002

(65) Prior Publication Data

US 2003/0166459 A1 Sep. 4, 2003

Related U.S. Application Data

(62) Division of application No. 09/966,068, filed on Oct. 1, 2001, now Pat. No. 6,590,045, which is a division of application No. 08/987,768, filed on Dec. 9, 1997, now Pat. No. 6,340,652.

(30) Foreign Application Priority Data

| Dec. 9, 1996 | (JP) | ................................ 8-328352 |
| Apr. 10, 1997 | (JP) | ................................ 9-108210 |
| Jul. 24, 1997 | (JP) | ................................ 9-214186 |

(51) Int. Cl.[7] .......................... C07F 17/00; B01J 31/00
(52) U.S. Cl. .......................... 556/11; 556/12; 556/28; 556/43; 556/53; 556/58; 526/160; 526/943; 502/103; 502/117
(58) Field of Search ...................... 556/11, 12, 28, 556/43, 53, 58; 526/160, 943; 502/103, 117

(56) References Cited

U.S. PATENT DOCUMENTS

| 4,289,651 A | 9/1981 | Benton et al. .......... 252/429 B |
| 4,727,124 A | 2/1988 | Konrad et al. .............. 526/105 |
| 5,283,043 A | 2/1994 | Johnson et al. .......... 423/328.2 |
| 5,308,811 A | 5/1994 | Suga et al. .................... 502/62 |
| 5,399,636 A | 3/1995 | Alt et al. ..................... 526/129 |
| 5,489,659 A | 2/1996 | Sugano et al. ............... 526/127 |
| 5,510,502 A * | 4/1996 | Sugano et al. ................. 556/11 |
| 5,670,683 A | 9/1997 | Langhauser et al. ........ 556/406 |
| 5,753,578 A | 5/1998 | Santi et al. .................. 502/114 |
| 5,830,820 A | 11/1998 | Yano et al. .................... 502/62 |
| 5,854,165 A | 12/1998 | Yabunouchi et al. ....... 502/117 |
| 5,869,417 A | 2/1999 | Woo et al. .................. 502/107 |
| 5,928,982 A | 7/1999 | Suga et al. .................. 502/118 |
| 6,218,558 B1 * | 4/2001 | Kato et al. ..................... 556/12 |
| 6,218,588 B1 | 4/2001 | Dommisse et al. ........... 585/12 |
| 6,252,097 B1 * | 6/2001 | Sugano et al. ................. 556/11 |
| 6,340,652 B1 | 1/2002 | Sugano et al. .............. 502/118 |
| 6,344,530 B2 | 2/2002 | Sugano et al. .............. 526/160 |
| 6,509,426 B2 * | 1/2003 | Kato et al. ................... 526/127 |
| 6,590,045 B2 * | 7/2003 | Sugano et al. .............. 526/126 |

FOREIGN PATENT DOCUMENTS

| EP | 0 270 314 | 6/1988 |
| EP | 0 511 665 A3 | 11/1992 |
| EP | 0 511 665 A2 | 11/1992 |
| EP | 0 611 772 A2 | 8/1994 |
| EP | 0 697 418 A1 | 2/1996 |
| EP | 0 728 773 A1 | 8/1996 |

* cited by examiner

Primary Examiner—Porfirio Nazario-Gonzalez
(74) Attorney, Agent, or Firm—Nixon & Vanderhye P.C.

(57) ABSTRACT

The present invention relates to a catalyst for polymerization of α-olefin, which comprises:

an essential component (A) of a transition metal compound, an essential component (B) of an ion exchangeable layer compound except for silicate, or an inorganic silicate, and an optional component (C) of an organoaluminum compound, said component (A) being represented by the general formula (I):

(I)

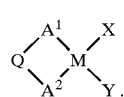

2 Claims, No Drawings

CATALYSTS FOR POLYMERIZATION OF α-OLEFINS, PROCESS FOR PRODUCING α-OLEFIN POLYMERS, NOVEL TRANSITION METAL COMPOUNDS AND CATALYST COMPONENTS FOR POLYMERIZATION OF α-OLEFIN

This application is a division of application No. 09/966,068, filed Oct. 1, 2001, now U.S. Pat. No. 6,590,045, which in turn is a division of application Ser. No. 08/987,768 filed Dec. 9, 1997 now U.S. Pat. No. 6,340,652, the entire content of each of which is hereby incorporated by referrence in this application.

BACKGROUND OF THE INVENTION

The present invention relates to catalysts for polymerization of α-olefin, a process for producing α-olefin polymers, novel transition metal compounds and catalyst components for polymerization of α-olefin.

As catalysts for polymerization of α-olefin, those comprising metallocene and aluminoxane have been proposed (Japanese Patent Application Laid-open (KOKAI) No. 60-35007, Japanese Patent Publication (KOKOKU) No. 4-12283, etc.). However, since the afore-mentioned catalysts are soluble in reaction solvent, the obtained polymer has extremely poor properties in which the polymer has irregular particle shape, has low bulk density and includes a large amount of fine powder therein. Therefore, in the case where these catalysts are applied to a slurry polymerization or a gas-phase polymerization of α-olefin, there have been caused various problems concerning the production of polymers, for example, it has been difficult to conduct safe operations continuously, for the production of polymers.

On the other hand, in order to solve the afore-mentioned problems, there have been proposed catalysts obtained by supporting one or both of a transition metal compound and an organoaluminum on an inorganic oxide such as silica or alumina or an organic substance (Japanese Patent Applications Laid-Open (KOKAI) Nos. 61-108610, 60-135408, 61-296008, 3-74412 and 3-74415, etc.).

However, polymers obtained by using such catalysts have contained a large amount of fine particles or coarse particles, and deteriorated in particle properties such as low bulk density. Further, there arises problems in which the catalysts have a low catalytic activity for the polymerization based on unit weight of solid components thereof, and the obtained polymers have disadvantages such as lower molecular weight or lower stereo regularity as compared to those obtained by using catalysts not supported on a carrier.

SUMMARY OF THE INVENTION

The present invention has been attained for solving the afore-mentioned problems in the prior arts.

It is an object of the present invention to provide catalysts for polymerization of α-olefins, capable of producing α-olefin polymers which are free from poor in properties caused by supporting the catalyst on a carrier such as low molecular weight or low stereo regularity, and which can show not only a narrow composition distribution but also excellent transparency and mechanical strength, and to a process for producing the α-olefin polymer by using the said catalyst.

It is another object of the present invention to provide novel transition metal compounds and catalyst components (catalytically active components) for polymerization of α-olefin.

As a result of the present inventors' earnest studies, it has been found that by using a catalyst comprising a specific transition metal compound and either a specific ion exchangeable layer compound or an inorganic silicate, the above-mentioned objects can be readily achieved.

In a first aspect of the present invention, there is provided a catalyst for polymerization of α-olefin, which comprises:

an essential component (A) of a transition metal compound, an essential component (B) of an ion exchangeable layer compound except for silicate, or an inorganic silicate, and an optional component (C) of an organoaluminum compound, said component (A) being represented by the general formula (I):

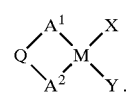

(I)

wherein $A^1$ and $A^2$ are independently a conjugate 5-membered ring ligand with the proviso that $A^1$ and $A^2$ may be the same or different in a molecule, and at least one of $A^1$ and $A^2$ forms a 7- to 10-membered condensed ring including adjacent two carbon atoms of the conjugate 5-membered ring, which condensed ring is formed by joining two adjacent substituent groups on the conjugate 5-membered ring; Q is a bridging group of the two conjugate 5-membered rings of $A^1$ and $A^2$ at optional positions of the 5-membered rings; M is a metal atom selected from the group consisting of elements belonging to Group 4–6 of the Periodic Table; and X and Y are independently a hydrogen atom, a halogen atom, a hydrocarbon group, an amino group, a halogenated hydrocarbon group, an oxygen-containing hydrocarbon group, a nitrogen-containing hydrocarbon group, a phosphorus-containing hydrocarbon group or a silicon-containing hydrocarbon group.

In a second aspect of the present invention, there is provided a catalyst for polymerization of α-olefin, which comprises:

an essential component (A) of a transition metal compound, an essential component (D) of an aluminumoxy compound, an ionic compound capable of reacting with the component (A) so as to convert the component (A) to a cation, or a Lewis acid, and an optional component (E) of a fine particle carrier, said component (A) being represented by the following general formula (II), (III), (IV), (V) or (VI) included in the above general formula (I).

General Formula (II)

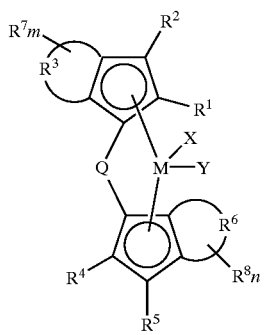

(II)

General Formula (III)

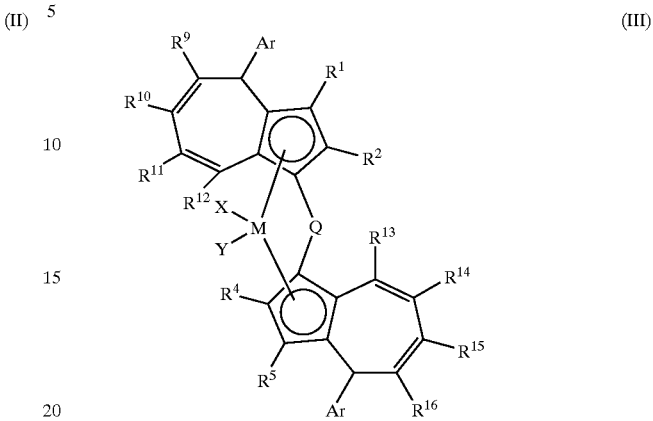

(III)

wherein $R^1$, $R^2$, $R^4$ and $R^5$ are independently a hydrogen atom, a hydrocarbon group having 1 to 10 carbon atoms, a silicon-containing hydrocarbon group having 1 to 18 carbon atoms or halogenated hydrocarbon group having 1 to 18 carbon atoms; $R^3$ and $R^6$ are independently a saturated or unsaturated divalent hydrocarbon group having 3 to 10 carbon atoms, which forms a condensed ring in cooperation with each of 5-membered rings to which $R^3$ and $R^6$ are respectively bonded, with the proviso that at least one of $R^3$ and $R^6$ has 5 to 8 carbon atoms and forms a 7- to 10-membered condensed ring having at least one unsaturated bond derived from $R^3$ or $R^6$; $R^7$ and $R^8$ are independently a hydrocarbon group having 1 to 20 carbon atoms, a halogenated hydrocarbon group having 1 to 20 carbon atoms, an oxygen-containing hydrocarbon group having 1 to 20 carbon atoms, an amino group, a nitrogen-containing hydrocarbon group having 1 to 20 carbon atoms or a sulfur-containing hydrocarbon group having 1 to 20 carbon atoms with the proviso that at least one of $R^7$ and $R^8$ is the halogenated hydrocarbon group having 1 to 20 carbon atoms; m and n are independently an integer of 0 to 20 with the proviso that m and n are not 0 at the same time; Q is a bridging group of the two 5-membered rings, and is a divalent hydrocarbon group having 1 to 20 carbon atoms, a divalent halogenated hydrocarbon group having 1 to 20 carbon atoms, a silylene or an oligosilylene group which may have a hydrocarbon group or halogenated hydrocarbon group having 1 to 20 carbon atoms or a germylene group which may have a hydrocarbon group or halogenated hydrocarbon group having 1 to 20 carbon atoms; X and Y are independently a hydrogen atom, a halogen atom, a hydrocarbon group having 1 to 20 carbon atoms, a silicon-containing hydrocarbon group having 1 to 20 carbon atoms, a halogenated hydrocarbon group having 1 to 20 carbon atoms, an oxygen-containing hydrocarbon group having 1 to 20 carbon atoms, an amino group or a nitrogen-containing hydrocarbon group having 1 to 20 carbon atoms; and M is a transition metal selected from the group consisting of elements belonging to Group 4–6 of the Periodic Table.

wherein $R^1$, $R^2$, $R^4$, $R^5$, Q, X, and M have the same meanings as defined in the above general formula (II); $R^9$, $R^{10}$, $R^{11}$, $R^{12}$, $R^{13}$, $R^{14}$, $R^{15}$ and $R^{16}$ are independently a hydrocarbon group having 1 to 20 carbon atoms or a halogenated hydrocarbon group having 1 to 20 carbon atoms; and Ar is an aryl group which may be substituted, with the proviso that at least one of the two 7-membered rings is bonded to the halogenated hydrocarbon group having 1 to 20 carbon atoms.

General Formula (IV)

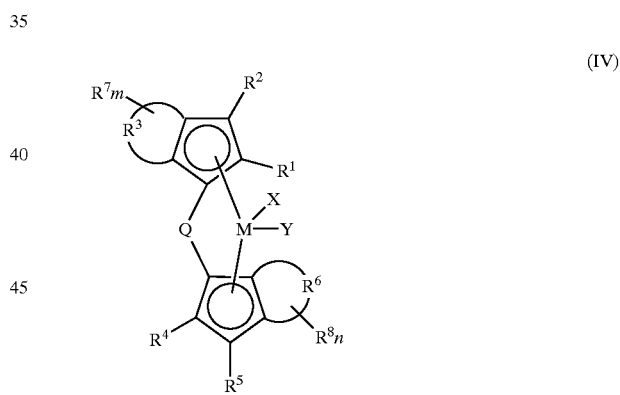

(IV)

wherein $R^1$ and $R^4$ are independently a hydrocarbon group having 7 to 12 carbon atoms, a silicon-containing hydrocarbon group having 8 to 18 carbon atoms or a halogenated hydrocarbon group having 7 to 12 carbon atoms; $R^2$ and $R^5$ are independently a hydrogen atom, a hydrocarbon group having 1 to 10 carbon atoms, a silicon-containing hydrocarbon group having 1 to 18 carbon atoms or a halogenated hydrocarbon group having 1 to 18 carbon atoms; $R^3$ and $R^6$ are independently a saturated or unsaturated divalent hydrocarbon group having 3 to 10 carbon atoms and forms a condensed ring in cooperation with 5-membered rings to which $R^3$ and $R^6$ are respectively bonded, with the proviso that at least one of $R^3$ and $R^6$ has 5 to 10 carbon atoms and forms a 7- to 10-membered condensed ring having at least one unsaturated bond derived from $R^3$ or $R^6$; $R^7$ and $R^8$ are independently a hydrocarbon group having 1 to 20 carbon atoms, an oxygen-containing hydrocarbon group having 1 to 20 carbon atoms, an amino group, a nitrogen-containing hydrocarbon group having 1 to 20 carbon atoms or a sulfur-containing hydrocarbon group having 1 to 20 carbon atoms; m and n are independently an integer of 0 to 20 with the proviso that m and n are not 0 at the same time, and when m or n is an integer of not less than 2, the $R^7$ or the $R^8$ may be bonded to each other to form a ring; Q is a bridging group of the two 5-membered rings, and is a divalent hydrocarbon group having 1 to 20 carbon atoms, a divalent halogenated hydrocarbon group having 1 to 20 carbon atoms, a silylene or an oligosilylene group which may be substituted with a hydrocarbon group having 1 to 20 carbon atoms or a halogenated hydrocarbon group having 1 to 20 carbon atoms, or a germylene group which may be substituted with a hydrocarbon group having 1 to 20 carbon atoms or a halogenated hydrocarbon group having 1 to 20 carbon atoms; X and Y are independently a hydrogen atom, a halogen atom, a hydrocarbon group having 1 to 20 carbon atoms, a silicon-containing hydrocarbon group having 1 to 20 carbon atoms, a halogenated hydrocarbon group having 1 to 20 carbon atoms, an oxygen-containing hydrocarbon group having 1 to 20 carbon atoms, an amino group or a nitrogen-containing hydrocarbon group having 1 to 20 carbon atoms; and M is a transition metal selected from the group consisting of elements belonging to Group 4–6 of the Periodic Table.

General Formula (V)

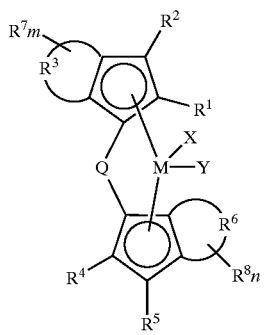

(V)

wherein $R^1$ and $R^4$ are independently a hydrocarbon group having 7 to 12 carbon atoms, a silicon-containing hydrocarbon group having 8 to 18 carbon atoms or a halogenated hydrocarbon group having 7 to 12 carbon atoms; $R^2$ and $R^5$ are independently a hydrogen atom, a hydrocarbon group having 1 to 10 carbon atoms, a silicon-containing hydrocarbon group having 1 to 18 carbon atoms or a halogenated hydrocarbon group having 1 to 18 carbon atoms; $R^3$ and $R^6$ are independently a saturated or unsaturated divalent hydrocarbon group having 3 to 10 carbon atoms and forms a condensed ring in cooperation with 5-membered rings to which $R^3$ and $R^6$ are respectively bonded, with the proviso that at least one of $R^3$ and $R^6$ has 5 to 10 carbon atoms and forms a 7- to 10-membered condensed ring having at least one unsaturated bond derived from $R^3$ or $R^6$; $R^7$ and $R^8$ are independently a hydrocarbon group having 1 to 20 carbon atoms, an oxygen-containing hydrocarbon group having 1 to 20 carbon atoms, an amino group, a nitrogen-containing hydrocarbon group having 1 to 20 carbon atoms or a sulfur-containing hydrocarbon group having 1 to 20 carbon atoms; m and n are independently an integer of 0 to 20 with the proviso that m and n are not 0 at the same time, and when m or n is an integer of not less than 2, the $R^7$ or the $R^8$ may be bonded to each other to form a ring; Q is a bridging group of the two 5-membered rings, and is a divalent hydrocarbon group having 1 to 20 carbon atoms, a divalent halogenated hydrocarbon group having 1 to 20 carbon atoms, a silylene or an oligosilylene group which may be substituted with a hydrocarbon group having 1 to 20 carbon atoms or a halogenated hydrocarbon group having 1 to 20 carbon atoms, or a germylene group which may be substituted with a hydrocarbon group having 1 to 20 carbon atoms or a halogenated hydrocarbon group having 1 to 20 carbon atoms; X and Y are independently a hydrogen atom, a halogen atom, a hydrocarbon group having 1 to 20 carbon atoms, a silicon-containing hydrocarbon group having 1 to 20 carbon atoms, a halogenated hydrocarbon group having 1 to 20 carbon atoms, an oxygen-containing hydrocarbon group having 1 to 20 carbon atoms, an amino group or a nitrogen-containing hydrocarbon group having 1 to 20 carbon atoms; and M is a transition metal selected from the group consisting of elements belonging to Group 4–6 of the Periodic Table.

General Formula (VI)

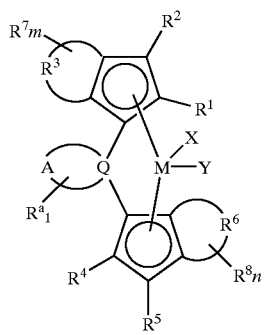

(VI)

wherein $R^1$, $R^2$, $R^4$ and $R^5$ are independently a hydrogen atom, a hydrocarbon group having 1 to 10 carbon atoms, a silicon-containing hydrocarbon group having 1 to 18 carbon atoms or a halogenated hydrocarbon group having 1 to 18 carbon atoms; $R^3$ and $R^6$ are independently a saturated or unsaturated divalent hydrocarbon group having 3 to 10 carbon atoms and forms a condensed ring in cooperation with 5-membered rings to which $R^3$ and $R^6$ are respectively bonded, with the proviso that at least one of $R^3$ and $R^6$ has 5 to 8 carbon atoms and forms a 7- to 10-membered condensed ring having at least one unsaturated bond derived from $R^3$ or $R^6$; $R^7$ and $R^8$ are independently a hydrocarbon group having 1 to 20 carbon atoms, an oxygen-containing hydrocarbon group having 1 to 20 carbon atoms, an amino group, a nitrogen-containing hydrocarbon group having 1 to 20 carbon atoms or a sulfur-containing hydrocarbon group having 1 to 20 carbon atoms; Q is a silicon atom, a germanium atom or a tin atom; A is a divalent unsaturated hydrocarbon group having 3 to 12 carbon atoms and forms a ring in cooperation with the Q to which A is bonded; $R^a$ is a saturated or unsaturated hydrocarbon group having 1 to 10 carbon atom; m and n are independently an integer of 0 to 20 with the proviso that m and n are not 0 at the same time, that when m or n is an integer of not less than 2, the $R^7$ or the $R^8$ may be bonded to each other to form a ring; l is an integer of 0 to 22, when l is an integer of not less than 2, the $R^a$ may be bonded to each other to form a ring; X and Y are independently a hydrogen atom, a halogen atom, a hydrocarbon group having 1 to 20 carbon atoms, a silicon-containing hydrocarbon group having 1 to 20 carbon atoms, a halogenated hydrocarbon group having 1 to 20 carbon atoms, an oxygen-containing hydrocarbon group having 1 to 20 carbon atoms, an amino group or a nitrogen-containing hydrocarbon group having 1 to 20 carbon atoms; and M is a transition metal selected from the group consisting of elements belonging to Group 4–6 of the Periodic Table.

In a third aspect of the present invention, there is provided a process for producing an α-olefin polymer, comprising bringing an α-olefin into contact with any of the catalysts defined in the afore-mentioned first and second aspects to conduct the polymerization or copolymerization of the α-olefin.

In a fourth aspect of the present invention, there is provided a novel transition metal compound represented by the afore-mentioned general formula (II).

In a fifth aspect of the present invention, there is provided a novel transition metal compound represented by the afore-mentioned general formula (III).

In a sixth aspect of the present invention, there is provided a novel transition metal compound represented by the afore-mentioned general formula (IV).

In a seventh aspect of the present invention, there is provided a novel transition metal compound represented by the afore-mentioned general formula (V).

In an eighth aspect of the present invention, there is provided a novel transition metal compound represented by the afore-mentioned general formula (VI).

In a ninth aspect of the present invention, there is provided a catalyst component for polymerization of α-olefin which comprises a transition metal compound represented by the afore-mentioned general formula (II).

In a tenth aspect of the present invention, there is provided a catalyst component for polymerization of α-olefin which comprises a transition metal compound represented by the afore-mentioned general formula (III).

In an eleventh aspect of the present invention, there is provided a catalyst component for polymerization of α-olefin which comprises a transition metal compound represented by the afore-mentioned general formula (IV).

In a twelfth aspect of the present invention, there is provided a catalyst component for polymerization of α-olefin which comprises a transition metal compound represented by the afore-mentioned general formula (V).

In a thirteenth aspect of the present invention, there is provided a catalyst component for polymerization of α-olefin which comprises a transition metal compound represented by the afore-mentioned general formula (VI).

DETAILED DESCRIPTION OF THE INVENTION

The present invention is described in detail below.

The catalyst for polymerization of α-olefin according to the present invention comprises a specific transition metal compound (component A) as an essential component.

First, the component A of transition metal compound is explained below. In the present invention, as the transition metal compound, there can be used those compounds represented by the general formula (I):

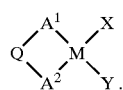

(I)

In the afore-mentioned general formula (I), $A^1$ and $A^2$ are conjugate 5-membered ring ligands with the proviso that $A^1$ and $A^2$ may be the same or different in a molecule and at least one of $A^1$ and $A^2$ forms a 7- to 10-membered condensed ring including adjacent two carbon atoms of the conjugate 5-membered ring, which condensed ring is formed by joining two adjacent substituent groups on the conjugate 5-membered ring. Further, the conjugate 5-membered ring ligands represented by $A^1$ and $A^2$ may have substituent groups bonded to carbon atoms other than those bonded to the group Q.

An typical example of the above conjugate 5-membered ring ligands is a cyclopentadienyl group. The cyclopentadienyl group may be an unsubstituted one, i.e., "$C_5H_4$—" having four hydrogen atoms, or may be substituted ones in which one or more of the hydrogen atoms are substituted by any substituent groups, as described above.

Examples of the substituent groups are hydrocarbon groups having 1 to 20 carbon atoms, preferably 1 to 15 carbon atoms. Specific examples of the hydrocarbon groups may include a methyl group, an ethyl group, a propyl group, a butyl group, a hexyl group, an octyl group, a phenyl group, a naphthyl group, a butenyl group, a butadienyl group, a triphenylcarbyl group or the like.

The afore-mentioned hydrocarbon groups may be monovalent groups bonded to the cyclopentadienyl group. Further, the two hydrocarbon substituent groups may be bonded with each other at end positions thereof to form a condensed ring. Typical examples of the cyclopentadienyl groups having the condensed ring may include indene, fluorene, azulene or derivatives thereof. Incidentally, in the present invention, the transition metal compounds used are required to have at least one 7- to 10-membered ring as the condensed ring, as described in detail hereinafter.

As the substituent groups other than the afore-mentioned hydrocarbon groups, there can be exemplified hydrocarbon groups containing silicon, oxygen, nitrogen, phosphorus, boron, sulfur or the like. Typical examples of the hydrocarbon residues may include a methoxy group, an ethoxy group, a phenoxy group, a furyl group, a trimethylsilyl group, a diethylamino group, a diphenylamino group, a pyrazolyl group, an indolyl group, a carbazolyl group, a dimethylphosphino group, a diphenylphosphino group, a diphenylboron group, a dimethoxyboron group, a thienyl group or the like.

As other substituent groups, there can be exemplified halogen, halogen-containing hydrocarbons or the like. Typical examples of the other substituent groups may include a chlorine atom, a bromine atom, a fluorine atom, a trichloromethyl group, a thrifluoromethyl group, a fluorophenyl group, a pentafluorophenyl group or the like.

Meanwhile, in the transition metal compounds used in the present invention, at least one of the conjugate 5-membered ring ligands $A^1$ and $A^2$ has a 7- to 10-membered condensed ring including adjacent two carbon atoms thereof and the condensed ring is formed by joining two adjacent substituent groups on the conjugate 5-membered ring. That is, at least one of $A^1$ and $A^2$ must form a 7- to 10-membered condensed ring which includes adjacent two carbon atoms of the conjugate 5-membered ring ligand.

Examples of the afore-mentioned ligands which constitute at least one of $A^1$ and $A^2$, may include a hydroazulenyl group, a methylhydroazulenyl group, an ethylhydroazulenyl group, a dimethylhydroazulenyl group, a methylethylhydroazulenyl group, a methylisopropylhydroazulenyl group, a methylphenylisopropylhydroazulenyl group, various hydrogenated azulenyl groups, a bicyclo-[6.3.0]-undecanyl group, a methyl-bicyclo-[6.3.0]-undecanyl group, an ethyl-bicyclo-[6.3.0]-undecanyl group, a phenyl-bicyclo-[6.3.0]-undecanyl group, a methylphenyl-bicyclo-[6.3.0]-undecanyl group, an ethylphenyl-bicyclo-[6.3.0]-undecanyl group, a methyldiphenyl-bicyclo-[6.3.0]-undecanyl group, a methylbicyclo-[6.3.0]-undecadienyl group, a methylphenyl-bicyclo-[6.3.0]-undecadienyl group, an ethylphenyl-bicyclo-[6.3.0]-undecadienyl group, a methylisopropyl-bicyclo-[6.3.0]-undecadienyl group, a bicyclo-[7.3.0]-dodecanyl group or derivatives thereof, a bicyclo-[7.3.0]-dodecadienyl group or derivatives thereof, a bicyclo-[8.3.0]-tridecanyl group or derivatives thereof, a bicyclo-[8.3.0]-tridecadienyl group or derivatives thereof, or the like.

The afore-mentioned groups may further have substituent groups such as hydrocarbon groups, hydrocarbon groups containing silicon, oxygen, nitrogen, phosphorus, boron, sulfur or the like, halogens or halogen-containing hydrocarbons, etc., as described hereinbefore.

The Q is a bridging group of the two conjugate 5-membered rings of $A^1$ and $A^2$ at optional positions of the 5-membered rings. That is, the Q is a divalent bonding group and acts to cross-link the two conjugate 5-membered rings with each other. The kinds of bonding groups Q are not particularly restricted. Examples of the bonding groups Q may include (a) divalent hydrocarbon or halogenated hydrocarbon groups having usually 1 to 20 carbon atoms, preferably 1 to 12 carbon atoms, more specifically, unsaturated divalent hydrocarbon groups such as alkylene groups, cycloalkylene groups, arylene groups, haloalkylene groups or halocycloalkylene groups; (b) silylene groups or oligosilylene groups; (c) silylene groups or oligosilylene groups substituted with hydrocarbon or halogenated hydrocarbon groups having usually 1 to 20 carbon atoms, preferably 1 to 12 carbon atoms; (d) germylene groups; (e) germylene groups substituted with hydrocarbon or halogenated hydrocarbon groups having usually 1 to 20 carbon atoms; or the like. Among them, alkylene groups, cycloalkylene groups, arylene groups, silylene groups substituted with hydrocarbon groups or germylene groups substituted with hydrocarbon groups are preferred.

The M represents a transition metal atom selected from the group consisting of elements belonging to Group 4–6 of the Periodic Table. Among them, Group 4 transition metals such as titanium, zirconium or hafnium are preferred, and zirconium or hafnium is more preferred.

The X and Y represent independently a hydrogen atom, a halogen atom, a hydrocarbon group, an amino group, a halogenated hydrocarbon group, an oxygen-containing hydrocarbon group, a nitrogen-containing hydrocarbon group, a phosphorus-containing hydrocarbon group or a silicon-containing hydrocarbon group. Each of the afore-mentioned hydrocarbon groups may have usually 1 to 20 carbon atoms, preferably 1 to 12 carbon atoms. Specific examples of the preferred X and Y may include a hydrogen atom, a chlorine atom, a methyl group, an isobutyl group, a phenyl group, a dimethyl amino group, a diethyl amino group or the like.

Some groups of the transition metal compounds represented by the aforementioned general formula (I), i.e., the transition metal compounds represented by the below-mentioned general formula (II), (III), (IV), (V) and (VI) are novel compounds.

The novel transition metal compounds classified into the first group is explained below. The transition metal compounds of the first group is represented by the general formula (II):

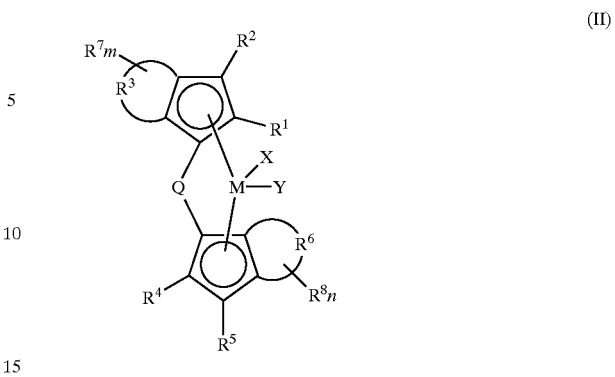

(II)

The novel transition metal compound represented by the general formula (II) involves compounds (a) in which the 5-membered ring ligand having substituent groups $R^1$, $R^2$ and $R^3$ and the 5-membered ring ligand having substituent groups $R^4$, $R^5$ and $R^6$ are asymmetrical with respect to a plane containing M, X and Y when viewed as to the relative positions thereof through the group Q, and compounds (b) in which the 5-membered ring ligand having substituent groups $R^1$, $R^2$ and $R^3$ and the 5-membered ring ligand having substituent groups $R^4$, $R^5$ and $R^6$ are symmetrical with respect to a plane containing M, X and Y when viewed as to the relative positions thereof through the group Q.

In order to produce α-olefin polymers having a high molecular weight and a high melting point, the afore-mentioned compounds (a), i.e., the compounds in which the two 5-membered ring ligands do not have a relationship of real and mirror images with respect to the plane containing M, X and Y, can be preferably used. Also, in case of use of the novel transition metal compound represented by the following general formulae (III), (IV), (V) and (VI).

In the general formula (II), $R^1$, $R^2$, $R^4$ and $R^5$ are independently a hydrogen atom, a hydrocarbon group having 1 to 10 carbon atoms, a silicon-containing hydrocarbon group having 1 to 18 carbon atoms or halogenated hydrocarbon group having 1 to 18 carbon atoms, as described above.

Specific examples of the afore-mentioned hydrocarbon group having 1 to 10 carbon atoms may include alkyl groups such as methyl, ethyl, n-propyl, i-propyl, n-butyl, i-butyl, s-butyl, t-butyl, n-pentyl, n-hexyl, cyclopropyl, cyclopentyl, cyclohexyl or methylcyclohexyl; alkenyl groups such as vinyl, propenyl or cyclohexenyl; aralkyl groups such as benzyl, phenylethyl or phenylpropyl; aryl-alkenyl groups such as trans-styryl; aryl groups such as phenyl, tolyl, dimethylphenyl, ethylphenyl, trimethylphenyl, 1-naphthyl or 2-naphthyl; or the like.

Specific examples of the afore-mentioned silicon-containing hydrocarbon atom having 1 to 18 carbon atoms may include trialkylsilyl groups such as trimethylsilyl, triethylsilyl or t-butyldimethylsilyl; triarylsilyl groups such as triphenylsilyl; (alkyl)(aryl)silyl groups such as dimethylphenylsilyl; alkylsilylalkyl groups such as bis(trimethylsilyl)methyl; or the like.

As the afore-mentioned halogen atoms contained in the halogenated hydrocarbon groups having 1 to 18 carbon atoms, there can be used a fluorine atom, a chlorine atom, a bromine atom and an iodine atom. In the case where the halogen atom contained in the halogenated hydrocarbon group is, for example, a fluorine atom, the fluorine atom can be bonded to optional position(s) of the hydrocarbon group. Specific examples of the halogenated hydrocarbon groups may include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoromethyl, 2,2,1,1-tetrafluoroethyl, pentafluoroethyl, pentachloroethyl, pentafluoropropyl, nonafluorobutyl, trifluorovinyl, 1,1-difluorobenzyl, 1,1,2,2-tetrafluorophenylethyl, o-, m- or p-fluorophenyl, o-, m- or p-chlorophenyl, o-, m- or p-bromophenyl, 2,4-, 3,5-, 2,6- or 2,5-difluorophenyl, 2,4-, 3,5-, 2,6- or 2,5-dichlorophenyl, 2,4,6-trifluorophenyl, 2,4,6-trichlorophenyl, pentafluorophenyl, pentachlorophenyl, 4-fluoronaphthyl, 4-chloronaphthyl, 2,4-difluoronaphthyl, heptafluoro-1-naphthyl, heptachloro-1-naphthyl, o-, m- or p-trifluoromethylphenyl, o-, m- or p-trichloromethylphenyl, 2,4-, 3,5-, 2,6- or 2,5-bis(trifluoromethyl)phenyl, 2,4-, 3,5-, 2,6- or 2,5-bis(trichloromethyl)phenyl, 2,4,6-tris(trifluoromethyl)phenyl, 4-trifluoromethylnaphthyl, 4-trichloromethylnaphthyl, 2,4-bis(trifluoromethyl)naphthyl or the like.

Among them, as the $R^1$ and $R^4$, hydrocarbon groups having 1 to 7 carbon atoms such as methyl, ethyl, propyl, butyl or benzyl are preferred, and as the $R^2$ and $R^5$, a hydrogen atom is preferred.

In the general formula (II), $R^3$ and $R^6$ are independently a saturated or unsaturated divalent hydrocarbon group having 3 to 10 carbon atoms and forms a condensed ring in cooperation with the 5-membered ring to which the $R^3$ or $R^6$ is bonded. The condensed ring formed by the $R^3$ or $R^6$ may be a 5- to 12-membered ring. However, it is essentially required that at least one of the $R^3$ and $R^6$ has 5 to 8 carbon atoms and forms a 7- to 10-membered condensed ring having at least one unsaturated bond derived from the $R^3$ or $R^6$. In this case, it is preferred that both of the condensed rings are 7- to 10-membered rings.

Specific examples of the $R^3$ and $R^6$ may include divalent saturated hydrocarbon groups such as trimethylene, tetramethylene, pentamethylene, hexamethylene or heptamethylene; divalent unsaturated hydrocarbon groups such as propenylene, 2-butenylene, 1,3-butadienylene, 1-pentenylene, 2-pentenylene, 1,3-pentadienylene, 1,4-pentadienylene, 1-hexenylene, 2-hexenylene, 3-hexenylene, 1,3-hexadienylene, 1,4-hexadienylene, 1,5-hexadienylene, 2,4-hexadienylene, 2,5-hexadienylene or 1,3,5-hexatrienylene; or the like. Among them, pentamethylene, 1,3-pentadienylene, 1,4-pentadienylene or 1,3,5-hexatrienylene are preferred, and 1,3-pentadienylene or 1,4-pentadienylene are especially preferred.

In the general formula (II), $R^7$ and $R^8$ are independently a hydrocarbon group having 1 to 20 carbon atoms, a halogenated hydrocarbon group having 1 to 20 carbon atoms, an oxygen-containing hydrocarbon group having 1 to 20 carbon atoms, an amino group, a nitrogen-containing hydrocarbon group having 1 to 20 carbon atoms or a sulfur-containing hydrocarbon group having 1 to 20 carbon atoms. However, it is required that at least one of the $R^7$ and $R^8$ is the halogenated hydrocarbon group having 1 to 20 carbon atoms.

Specific examples of the afore-mentioned hydrocarbon group having 1 to 20 carbon atoms may include alkyl groups such as methyl, ethyl, n-propyl, i-propyl, n-butyl, i-butyl, s-butyl, t-butyl, n-pentyl, n-hexyl, cyclopropyl, cyclopentyl, cyclohexyl or methylcyclohexyl; alkenyl groups such as vinyl, propenyl or cyclohexenyl; aralkyl groups such as benzyl, phenylethyl or phenylpropyl; arylalkenyl groups such as trans-styryl; aryl groups such as phenyl, tolyl, dimethylphenyl, ethylphenyl, trimethylphenyl, 1-naphthyl, 2-naphthyl, acenaphthyl, phenanthryl or anthryl; or the like. Among them, alkyl groups having 1 to 4 carbon atoms such as methyl, ethyl, n-propyl, i-propyl, n-butyl, i-butyl, s-butyl, t-butyl or cyclopropyl, and aryl groups having 6 to 20 carbon atoms such as phenyl, tolyl, dimethylphenyl, ethylphenyl, trimethylphenyl, 1-naphthyl or 2-naphthyl are preferred.

As the afore-mentioned halogen atoms contained in the halogenated hydrocarbon groups having 1 to 20 carbon atoms, there can be used a fluorine atom, a chlorine atom, a bromine atom and an iodine atom. In the case where the halogen atom contained in the halogenated hydrocarbon group is, for example, a fluorine atom, the fluorine atom can be bonded to optional position(s) of the hydrocarbon group. Specific examples of the halogenated hydrocarbon groups may include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, pentafluoropropyl, nonafluorobutyl, trifluorovinyl, 1,1-difluorobenzyl, 1,1,2,2-tetrafluorophenylethyl, o-, m- or p-fluorophenyl, o-, m- or p-chlorophenyl, o-, m- or p-bromophenyl, 2,4-, 3,5-, 2,6- or 2,5-difluorophenyl, 2,4-, 3,5-, 2,6- or 2,5-dichlorophenyl, 2,4,6-trifluorophenyl, 2,4,6-trichlorophenyl, pentafluorophenyl, pentachlorophenyl, 4-fluoronaphthyl, 4-chloronaphthyl, 2,4-difluoronaphthyl, heptafluoro-1-naphthyl, heptachloro-1-naphthyl, o-, m- or p-trifluoromethylphenyl, o-, m- or p-trichloromethylphenyl, 2,4-, 3,5-, 2,6- or 2,5-bis(trifluoromethyl)phenyl, 2,4-, 3,5-, 2,6- or 2,5-bis(trichloromethyl)phenyl, 2,4,6-tris(trifluoromethyl)phenyl, 4-trifluoromethylnaphthyl, 4-trichloromethylnaphthyl, 2,4-bis(trifluoromethyl)naphthyl or the like. Among them, fluorinated hydrocarbon groups or chlorinated hydrocarbon groups are preferred, and o-, m- or p-fluorophenyl, o-, m- or p-chlorophenyl or o-, m- or p-trifluoromethylphenyl are especially preferred.

Specific examples of the afore-mentioned oxygen-containing hydrocarbon groups having 1 to 20 carbon atoms may include alkoxy groups such as methoxy, ethoxy, propoxy, cyclopropoxy or butoxy; aryloxy groups such as phenoxy, methylphenoxy, dimethylphenoxy or naphthoxy; arylalkoxy groups such as phenylethoxy or naphthylmethoxy; oxygen-containing heterocyclic groups such as furyl group; or the like.

Specific examples of the afore-mentioned nitrogen-containing hydrocarbon groups having 1 to 20 carbon atoms may include alkylamino groups such as methylamino, dimethylamino, ethylamino or diethylamino; arylamino groups such as phenylamino or diphenylamino; (alkyl)(aryl) amino groups such as (methyl)(phenyl) amino; nitrogen-containg heterocyclic groups such as pyrazolyl or indolyl; or the like.

In the general formula (II), m and n are independently an integer of 0 to 20, preferably 1 to 5. If m and/or n are an integer of 2 to 20, a plurality of the $R^7$ or $R^8$ may be the same or different. The integers m and n are not zero at the same time. That is, it is essential that the divalent groups $R^3$ and/or $R^6$ have the afore-mentioned substituent groups $R^7$ or $R^8$, and the substituent groups $R^7$ and/or $R^8$ are the halogenated hydrocarbon groups having 1 to 20 carbon atoms. In addition, when the integer m or n is not less than 2, the $R^7$ or the $R^8$ may be bonded to each other to form an additional ring. The substituent group $R^7$ or $R^8$ may be bonded to any position of $R^3$ or $R^6$, but it is preferred that the substituent groups $R^7$ or $R^8$ is bonded to the carbon atoms of $R^3$ or $R^6$, adjacent to the 5-membered ring (the carbon at α-position).

In the general formula (II), Q is a bridging group of the two 5-membered rings, and is a divalent hydrocarbon group having 1 to 20 carbon atoms, a silylene or an oligosilylene group which may have a hydrocarbon or halogenated hydrocarbon group having 1 to 20 carbon atoms or a germylene group which may have a hydrocarbon group or halogenated hydrocarbon group having 1 to 20 carbon atoms. When silylene group or germylene group has two hydrocarbon or halogenated hydrocarbon groups, those groups may be bonded to each other to form a ring.

Specific examples of the group Q may include alkylene groups such as methylene, methylmethylene, dimethylmethylene, 1,2-ethylene, 1,3-trimethylene, 1,4-tetramethylene, 1,2-cyclohexylene or 1,4-cyclohexylene; arylalkylene groups such as (methyl)(phenyl)methylene or diphenylmethylene; silylene groups; alkylsilylene groups such as methylsilylene, dimethylsilylene, diethylsilylene, di(n-propyl)silylene, di(i-propyl)silylene or di(cyclohexyl) silylene; (alkyl)(aryl)silylene groups such as methylphenylsilylene or methyltolylsilylene; arylsilylene groups such as diphenylsilylene; haloalkylsilylene groups such as di(chloromethyl)silylene or di(2-chloroethyl)silylene; (alkyl)(haloalkyl)silylene groups such as methyl(4-chlorophenyl)silylene; di(haloalkyl)silylene groups such as di(4-chlorophenyl)silylene or bis(3,5-dichlorophenyl) silylene; germylene groups; alkyl germylene groups obtained by substituting germanium for a silicon atom of the afore-mentioned silylene groups having the $C_1$ to $C_{20}$ hydrocarbon groups; alkyl aryl germylene groups or aryl germylene groups; or the like. Among them, the silylene groups having the $C_1$ to $C_{20}$ hydrocarbon groups or the germylene groups having the $C_1$ to $C_{20}$ hydrocarbon groups are preferred, and the alkylsilylene groups, the alkyl arylsilylene groups or the arylsilylene groups are especially preferred.

In the general formula (II), X and Y represent independently a hydrogen atom, a halogen atom, a hydrocarbon group having 1 to 20 carbon atoms, silicon-containing hydrocarbon group having 1 to 20 carbon atoms, a halogenated hydrocarbon group having 1 to 20 carbon atoms, an oxygen-containing hydrocarbon group having 1 to 20 carbon atoms, an amino group or a nitrogen-containing hydrocarbon group having 1 to 20 carbon atoms.

As the afore-mentioned halogen atoms, there can be used a fluorine atom, a chlorine atom, a bromine atom and an iodine atom. As the afore-mentioned hydrocarbon groups having 1 to 20 carbon atoms and the halogenated hydrocarbon group having 1 to 20 carbon atoms, there can be exemplified the same hydrocarbon groups and halogenated hydrocarbon groups as defined above with respect to the $R^7$ and $R^8$.

Specific examples of the afore-mentioned silicon-containing hydrocarbon groups may include trialkylsilylmethyl groups such as trimethylsilylmethyl or triethylsilylmethyl; di(alkyl)(aryl)silyl methyl groups such as dimethylphenylsilylmethyl, diethylphenylsilylmethyl, dimethyltolylsilylmethyl; or the like.

Specific examples of the afore-mentioned oxygen-containing hydrocarbon groups having 1 to 20 carbon atoms may include alkoxy groups such as methoxy, ethoxy, propoxy, cyclopropoxy or butoxy; aryloxy groups such as phenoxy, methylphenoxy, dimethylphenoxy or naphthoxy; arylalkoxy groups such as phenylmethoxy or naphthylmethoxy; or the like.

Specific examples of the afore-mentioned nitrogen-containing hydrocarbon groups having 1 to 20 carbon atoms may include alkylamino groups such as methylamino, dimethylamino, ethylamino or diethylamino; arylamino groups such as phenylamino or diphenylamino; (alkyl)(aryl) amino groups such as (methyl)(phenyl) amino; or the like.

In the general formula (II), the X and Y are preferably a hydrogen atom, a halogen atom, a hydrocarbon group having 1 to 20 carbon atoms or a nitrogen-containing hydrocarbon group having 1 to 20 carbon atoms. Among them, the halogen atom, the hydrocarbon group having 1 to 20 carbon atoms or the nitrogen-containing hydrocarbon group having 1 to 20 carbon atoms are more preferred. Further, the especially preferred X and Y are a chlorine atom, a methyl group, an i-butyl group, a phenyl group, a dimethylamino group and a diethylamino group.

In the general formula (II), M represents a transition metal selected from the group consisting of elements belonging to Group 4–6 of the Periodic Table. Among them, Group 4 transition metals such as titanium, zirconium or hafnium are preferred. Further, zirconium or hafnium are more preferred.

The novel transition metal compounds represented by the general formula (II) can be produced by optional methods according to the kinds of substituent groups or bonding manners thereof. Typically, the transition metal compounds can be produced through the following reaction scheme. Incidentally, "$H_2R_a$" and "$H_2R_b$" in the reaction scheme have the following chemical formulae:

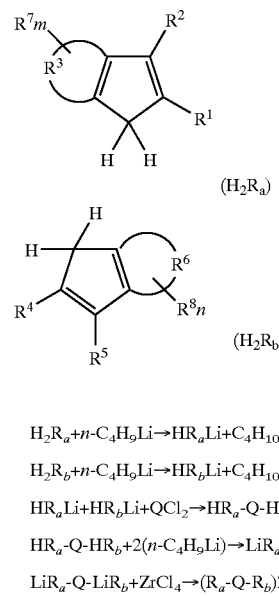

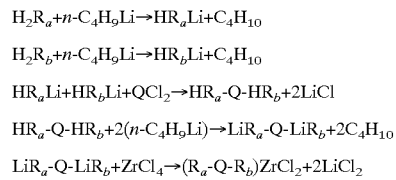

$H_2R_a + n\text{-}C_4H_9Li \rightarrow HR_aLi + C_4H_{10}$ $H_2R_b + n\text{-}C_4H_9Li \rightarrow HR_bLi + C_4H_{10}$ $HR_aLi + HR_bLi + QCl_2 \rightarrow HR_a\text{-}Q\text{-}HR_b + 2LiCl$ $HR_a\text{-}Q\text{-}HR_b + 2(n\text{-}C_4H_9Li) \rightarrow LiR_a\text{-}Q\text{-}LiR_b + 2C_4H_{10}$ $LiR_a\text{-}Q\text{-}LiR_b + ZrCl_4 \rightarrow (R_a\text{-}Q\text{-}R_b)ZrCl_2 + 2LiCl_2$ In addition, the metal salts of the cyclopentadienyl compounds such as the afore-mentioned $HR_aLi$ and $HR_bLi$ may be produced by addition reaction of alkyl groups or aryl groups, for example, as described in European Patent No. 697418. More specifically, an alkyl lithium compound or an aryl lithium compound is reacted with an azulene derivative in an inert solvent to produce a lithium salt of a dihydroazulenyl derivative. As the alkyl lithium compounds, there can be used methyl lithium, i-propyl lithium, n-butyl lithium, t-butyl lithium or the like. As the aryl lithium compounds, there can be used phenyl lithium, p-chlorophenyl lithium, p-fluorophenyl lithium, p-trifluoromethylphenyl lithium, naphthyl lithium or the like. In addition, as the inert solvents, there can be used hexane, benzene, toluene, diethyl ether, tetrahydrofuran or mixed solvents thereof.

Next, the novel transition metal compounds classified into the second group are explained below. The transition metal compounds of the second group are specific compounds among those belonging to the first group, which are represented by the general formula (III):

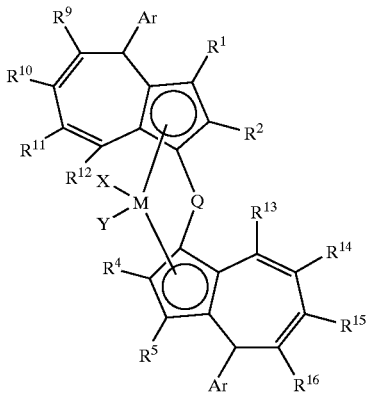

(III)

In the general formula (III), $R^1$, $R^2$, $R^4$, $R^5$, Q, X, Y and M have the same meanings as defined in the above general formula (II), and $R^9$, $R^{10}$, $R^{11}$, $R^{12}$, $R^{13}$, $R^{14}$, $R^{15}$ and $R^{16}$ bonding to 7-membered ring are independently a hydrocarbon group having 1 to 20 carbon atoms or a halogenated hydrocarbon group having 1 to 20 carbon atoms. The Ar represents an aryl group. However, it is required that at least one of the two 7-membered rings is substituted with the halogenated hydrocarbon group having 1 to 20 carbon atoms. As the hydrocarbon groups having 1 to 20 carbon atoms or the halogenated hydrocarbon groups having 1 to 20 carbon atoms, there can be exemplified the same hydrocarbon groups and halogenated hydrocarbon groups as defined above with respect to the general formula (II). Specific examples of the aryl groups may include a phenyl group, a naphthyl group, an anthryl group, a phenanthryl group or the like. These aryl groups may be substituted by 1 to 5 halogen atoms or halogenated hydrocarbon groups.

Next, the novel transition metal compounds classified into the third group are explained below. The transition metal compounds of the third group are represented by the general formula (IV):

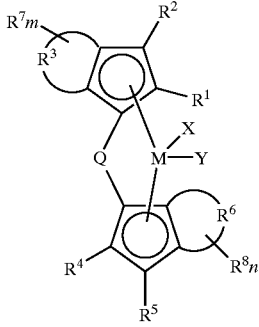

(IV)

In the general formula (IV), $R^1$ and $R^4$ are independently a hydrogen atom, a hydrocarbon group having 1 to 6 carbon atoms, a silicon-containing hydrocarbon group having 1 to 7 carbon atoms or a halogenated hydrocarbon group having 1 to 6 carbon atoms.

Examples of the afore-mentioned hydrocarbon groups having 1 to 6 carbon atoms may include alkyl groups such as methyl, ethyl, n-propyl, i-propyl, n-butyl, i-butyl, s-butyl, t-butyl, n-pentyl, n-hexyl, cyclopropyl, cyclopentyl or cyclohexyl; alkenyl groups such as vinyl, propenyl or cyclohexenyl; a phenyl group; or the like.

Examples of the afore-mentioned silicon-containing hydrocarbon groups having 1 to 7 carbon atoms may include trialkylsilyl groups such as trimethylsilyl, triethylsilyl or t-butyldimethylsilyl; alkylsilylalkyl groups such as bis (trimethylsilyl)methyl; or the like.

As the halogen atom in the afore-mentioned halogenated hydrocarbon groups having 1 to 6 carbon atoms, there may be used the same atoms as described with respect to the general formula (II). In case where the halogen atom contained in the halogenated hydrocarbon group is, for example, a fluorine atom, the afore-mentioned halogenated hydrocarbon groups is that substituted with fluorine atom at optional position(s) thereof. Specific examples of the halogenated hydrocarbon groups may include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, pentafluoropropyl, nonafluorobutyl, trifluorovinyl, o-, m- or p-fluorophenyl, o-, m- or p-chlorophenyl, o-, m- or p-bromophenyl, 2,4-, 3,5-, 2,6- or 2,5-difluorophenyl, 2,4-, 3,5-, 2,6- or 2,5-dichlorophenyl, 2,4,6-trifluorophenyl, 2,4,6-trichlorophenyl, pentafluorophenyl, pentachlorophenyl, or the like.

Among them, as the $R^1$ and $R^4$, the hydrocarbon groups having 1 to 6 carbon atoms such as methyl, ethyl, propyl or butyl are preferred.

In the general formula (IV), $R^2$ and $R^5$ are independently a hydrogen atom, a hydrocarbon group having 1 to 10 carbon atoms, a silicon-containing hydrocarbon group having 1 to 18 carbon atoms or a halogenated hydrocarbon group having 1 to 18 carbon atoms. Specific examples of the substituents $R^2$ and $R^5$ may be the same as those described in the general formula (II).

In the general formula (IV), $R^3$ is a saturated or unsaturated divalent hydrocarbon group having 3 to 10 carbon atoms and forms a condensed ring in cooperation with a 5-membered ring to which $R^3$ is bonded. Accordingly, the condensed ring formed by the $R^3$ is a 5- to 12-membered ring. Specific examples of the $R^3$ may include divalent saturated hydrocarbon groups such as trimethylene, tetramethylene, pentamethylene or hexamethylene; divalent unsaturated hydrocarbon groups such as propenylene, 2-butenylene, 1,3-butadienylene, 1-pentenylene, 2-pentenylene, 1,3-pentadienylene, 1,4-pentadienylene, 1-hexenylene, 2-hexenylene, 3-hexenylene, 1,3-hexadienylene, 1,4-hexadienylene, 1,5-hexadienylene, 2,4-hexadienylene, 2,5-hexadienylene or 1,3,5-hexatrienylene; or the like. Among them, pentamethylene, 1,3-pentadienylene, 1,4-pentadienylene or 1,3,5-hexatrienylene are preferred. Further, pentamethylene, 1,3-pentadienylene or 1,4-pentadienylene are more preferred. Still further, 1,3-pentadienylene or 1,4-pentadienylene are especially preferred.

That is, it is preferred that the $R^3$ is a $C_5$ divalent saturated or unsaturated hydrocarbon group forms a condensed ring in cooperation with the 5-membered ring to which the $R^3$ is bonded. It is more preferred that the $R^3$ is pentadienylene.

In the general formula (IV), $R^6$ is a saturated or unsaturated divalent hydrocarbon group having 5 to 8 carbon atoms and forms a condensed ring in cooperation with a 5-membered ring to which $R^6$ is bonded. Accordingly, the condensed ring formed by the $R^6$ is a 7- to 10-membered ring. Specific examples of the $R^6$ may include divalent saturated hydrocarbon groups such as pentamethylene, hexamethylene or heptamethylene; divalent unsaturated hydrocarbon groups such as 1-pentenylene, 2-pentenylene, 1,3- pentadienylene, 1,4-pentadienylene, 1-hexenylene, 2-hexenylene, 3-hexenylene, 1,3-hexadienylene, 1,4-hexadienylene, 1,5-hexadienylene, 2,4-hexadienylene, 2,5-hexadienylene or 1,3,5-hexatrienylene; or the like. Among them, pentamethylene, 1,3-pentadienylene, 1,4-pentadienylene or 1,3,5-hexatrienylene are preferred. Further, pentamethylene, 1,3-pentadienylene or 1,4-pentadienylene are more preferred. Still further, 1,3-pentadienylene or 1,4-pentadienylene are especially preferred.

That is, it is preferred that the $R^6$ is a $C_5$ divalent saturated or unsaturated hydrocarbon group forms a condensed ring in cooperation with the 5-membered ring to which the $R^6$ is bonded. It is more preferred that the $R^6$ is pentadienylene.

In the general formula (IV), $R^7$ and $R^8$ are independently a hydrocarbon group having 1 to 20 carbon atoms, an oxygen-containing hydrocarbon group having 1 to 20 carbon atoms, an amino group, a nitrogen-containing hydrocarbon group having 1 to 20 carbon atoms or a sulfur-containing hydrocarbon group having 1 to 20 carbon atoms, with the proviso that at least one $R^8$ is present at a β- or remoter position on $R^6$ with respect to the 5-membered ring. As the $R^7$ and $R^8$ of the general formula (IV), there may be used the same groups as those described in general formula (II) except for the halogenated hydrocarbon groups.

In the general formula (IV), m is an integer of 0 to 20 and n is an integer of 1 to 16. When m or n is an integer of not less than 2, the $R^7$ or the $R^8$ may be bonded to each other to form a ring. The m and n are preferably an integer of 1 to 5, more preferably 2 to 5. In the case where the m and/or n are an integer of not less than 2, a plurality of $R^7$ (or a plurality of $R^8$) may be the same or different. The position of $R^3$ to which the $R^7$ is bonded or the position of $R^6$ to which the $R^8$ is bonded is not particularly restricted except for the afore-mentioned definitions concerning the bonding position of the $R^8$, but it is preferred that the $R^7$ or the $R^8$ is bonded to a carbon atom of the $R^3$ or $R^6$ adjacent to the 5-membered ring (i.e., carbon atom of α-position).

In the general formula (IV), Q is a bridging group of the two 5-membered rings, and represents a divalent hydrocarbon group having 1 to 20 carbon atoms, a silylene or an oligosilylene group which may be substituted with a hydrocarbon group having 1 to 20 carbon atoms or a halogenated hydrocarbon group having 1 to 20 carbon atoms, or a germylene group which may be substituted with a hydrocarbon group having 1 to 20 carbon atoms or a halogenated hydrocarbon group having 1 to 20 carbon atoms. As the Q of the general formula (IV), there may be used the same groups as those described in general formula (II).

In the general formula (IV), X and Y are independently a hydrogen atom, a halogen atom, a hydrocarbon group having 1 to 20 carbon atoms, a halogenated hydrocarbon group having 1 to 20 carbon atoms, a silicon-containing hydrocarbon group having 1 to 20 carbon atoms, an oxygen-containing hydrocarbon group having 1 to 20-carbon atoms, an amino group or a nitrogen-containing hydrocarbon group having 1 to 20 carbon atoms. As the X and Y of the general formula (IV), there may be used the same groups as those described in general formula (II).

In the general formula (IV), M is a transition metal selected from the group consisting of elements belonging to Group 4–6 of the Periodic Table. As the M of the general formula (IV), there may be used the same transition metals as those described in general formula (II).

The novel transition metal compounds represented by the general formula (IV) can be produced by the same production method as used for the transition metal compound represented by the general formula (II).

Next, the novel transition metal compounds classified into the fourth group are explained below. The transition metal compounds of the fourth group are represented by the general formula (V):

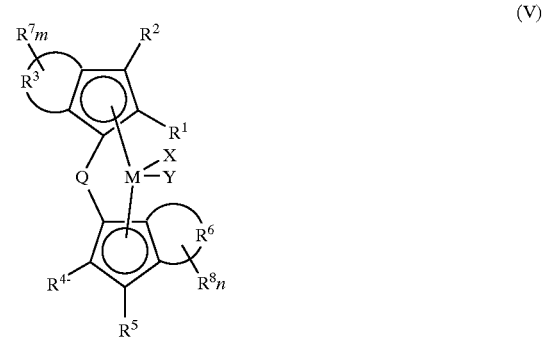

(V)

In the general formula (V), $R^1$ and $R^4$ are independently a hydrocarbon group having 7 to 12 carbon atoms, a silicon-containing hydrocarbon group having 8 to 18 carbon atoms or a halogenated hydrocarbon group having 7 to 12 carbon atoms Specific examples of the afore-mentioned $R^1$ and $R^4$ May include alkyl groups such as n-heptyl, 1,1,2,2-tetramethylpropyl, n-octyl, s-octyl, n-nonyl or cyclohexylmethyl; alkenyl groups such as 1-heptenyl, 2-heptenyl or cyclohexenylmethyl; aralkyl groups such as benzyl, 1-phenylethyl or 2-phenylethyl; aryl groups such as o-, m- or p-tolyl or 2,5-dimethylphenyl; or the like.

Specific examples of the afore-mentioned silicon-containing hydrocarbon group having 8 to 18 carbon atoms may include trialkylsilyl groups such as tripropylsilyl. tri-n-butylsilyl or tri-t-butylsilyl; (alkyl)(aryl) silyl groups such as dimethylphenylsilyl or methyldiphenylsilyl; alkylsilyl alkyl groups such as tris(trimethylsilyl)methyl; or the like.

As the halogen atom in the afore-mentioned halogenated hydrocarbon groups having 7 to 12 carbon atoms, there may be used the same atoms as described with respect to the general formula (II). In case where the halogen atom contained in the halogenated hydrocarbon group is, for example, a fluorine atom, the afore-mentioned halogenated hydrocarbon groups is that substituted with fluorine atom at optional position thereof. Specific examples of the halogenated hydrocarbon groups may include 1,1-difluorobenzyl, 1,1,2, 2-tetrafluorophenylethyl, 4-fluoronaphthyl, 4-chloronaphthyl, 2,4-difluoronaphthyl, heptafluoro-1-naphthyl, heptachloro-1-naphthyl, o-, m- or p-trifluoromethylphenyl, o-, m- or p-trichloromethylphenyl, 2,4-, 3,5-, 2,6- or 2,5-bis(trifluoromethyl)phenyl, 2,4-, 3,5-, 2,6- or 2,5-bis(trichloromethyl)phenyl, 2,4,6-tris (trifluoromethyl)phenyl, 4-trifluoromethylnaphthyl, 4-trichloromethylnaphthyl, 2,4-bis(trifluoromethyl)naphthyl or the like.

Among them, as $R^1$ and $R^4$, the hydrocarbon groups such as n-heptyl, benzyl or 1-phenylethyl are preferred. Further, the aralkyl groups such as benzyl or 1-phenylethyl are more preferred.

In the general formula (V), $R^2$ and $R^5$ are independently a hydrogen atom, a hydrocarbon group having 1 to 10 carbon atoms, a silicon-containing hydrocarbon group having 1 to 18 carbon atoms or a halogenated hydrocarbon group having 1 to 18 carbon atoms. As the $R^2$ and $R^5$ of the general formula (V), there may be used the same groups as described in the general formula (II)

In the general formula (V), $R^3$ and $R^6$ are independently a saturated or unsaturated divalent hydrocarbon group having 3 to 10 carbon atoms and forms a condensed ring in cooperation with 5-membered rings to which $R^3$ and $R^6$ are respectively bonded, with the proviso that at least one of $R^3$ and $R^6$ has 5 to 10 carbon atoms and forms a 7- to 10-membered condensed ring having at least one unsaturated bond derived from $R^3$ or $R^6$. As the $R^3$ and $R^6$ of the general formula (V), there may be used the same groups as described in the general formula (II).

In the general formula (V), $R^7$ and $R^8$ are independently a hydrocarbon group having 1 to 20 carbon atoms, an oxygen-containing hydrocarbon group having 1 to 20 carbon atoms, an amino group, a nitrogen-containing hydrocarbon group having 1 to 20 carbon atoms or a sulfur-containing hydrocarbon group having 1 to 20 carbon atoms. As the $R^7$ and $R^8$ of the general formula (V), there may be used the same groups as described in the general formula (II) except for halogenated hydrocarbon groups.

In the general formula (V), m and n are independently an integer of 0 to 20, preferably 1 to 5. In the case where the m and/or n is an integer of 2 to 20, a plurality of $R^7$ (or a plurality of $R^8$) may be the same or different. However, in this case, m and n are not zero at the same time. In addition, when the m or n is an integer of not less than 2, $R^7$ or $R^8$ may be bonded to each other to form a ring. The substituent group $R^7$ or $R^8$ may be bonded to any position of $R^3$ or $R^6$, but it is preferred that the $R^7$ or the $R^8$ is bonded to a carbon atom of $R^3$ or $R^6$ adjacent to the 5-membered ring (i.e., carbon atom of α-position).

In the general formula (V), Q is a bridging group of the two 5-membered rings, and represents a divalent hydrocarbon group having 1 to 20 carbon atoms, a silylene or an oligosilylene group which may be substituted with a hydrocarbon group having 1 to 20 carbon atoms or a halogenated hydrocarbon group having 1 to 20 carbon atoms, or a germylene group which may be substituted with a hydrocarbon group having 1 to 20 carbon atoms or a halogenated hydrocarbon group having 1 to 20 carbon atoms. As the Q of the general formula (V), there may be used the same groups as described for that of the general formula (II)

In the general formula (V), X and Y are independently a hydrogen atom, a halogen atom, a hydrocarbon group having 1 to 20 carbon atoms, a halogenated hydrocarbon group having 1 to 20 carbon atoms, a silicon-containing hydrocarbon group having 1 to 20 carbon atoms, an oxygen-containing hydrocarbon group having 1 to 20 carbon atoms, an amino group or a nitrogen-containing hydrocarbon group having 1 to 20 carbon atoms. As the X and Y of the general formula (V), there may be used the same groups as described for those of the general formula (II).

In the general formula (V), M is a transition metal selected from the group consisting of elements belonging to Group 4–6 of the Periodic Table. As the M of the general formula (V), there may be used the same transition metals as described for that of the general formula (II).

The novel transition metal compounds represented by the general formula (V) can be produced by the same production method as used for the transition metal compound represented by the general formula (II).

Next, the novel transition metal compounds classified into the fifth group are explained below. The transition metal compounds of the fifth group are represented by the general formula (VI):

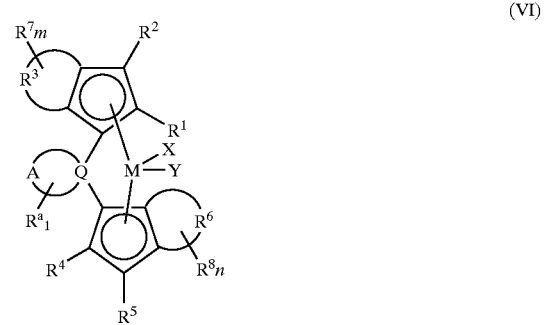

In the general formula (VI), $R^1$, $R^2$, $R^4$ and $R^5$ are independently a hydrogen atom, a hydrocarbon group having 1 to 10 carbon atoms, a silicon-containing hydrocarbon group having 1 to 18 carbon atoms or a halogenated hydrocarbon group having 1 to 18 carbon atoms. As the $R^1$, $R^2$, $R^4$ and $R^5$ of the general formula (VI), there may be used the same groups as described for those of the general formula (II).

In the general formula (VI), $R^3$ and $R^6$ are independently a saturated or unsaturated divalent hydrocarbon group having 3 to 10 carbon atoms and forms a condensed ring in cooperation with 5-membered rings to which $R^3$ and $R^6$ are respectively bonded, with the proviso that at least one of $R^3$ and $R^6$ has 5 to 8 carbon atoms and forms a 7- to 10-membered condensed ring having at least one unsaturated bond derived from $R^3$ or $R^6$. As the $R^3$ and $R^6$ of the general formula (VI), there may be used the same groups as described for those of the general formula (II) except for halogenated hydrocarbon groups.

In the general formula (VI), $R^7$ and $R^8$ are independently a hydrocarbon group having 1 to 20 carbon atoms, an oxygen-containing hydrocarbon group having 1 to 20 carbon atoms, an amino group, a nitrogen-containing hydrocarbon group having 1 to 20 carbon atoms or a sulfur-containing hydrocarbon group having 1 to 20 carbon atoms. As the $R^7$ and $R^8$ of the general formula (VI), there may be used the same groups as described for those of the general formula (II).

In the general formula (VI), Q is a silicon atom, a germanium atom or a tin atom. Among them, a silicon atom and a germanium atom are preferred.

In the general formula (VI), A is a divalent unsaturated hydrocarbon group having 3 to 12 carbon atoms and forms a ring in cooperation with the Q to which A is bonded. Specific examples of such unsaturated hydrocarbon groups may include divalent unsaturated hydrocarbon groups such as propenylene, butenylene, butadienylene, pentenylene, pentadienylene, hexenylene, hexadienylene, hexatrienylene or the like. Among them, divalent hydrocarbon groups having 3 to 5 carbon atoms such as propenylene, butenylene, butadienylene, pentenylene or pentadienylene are preferred. Further, butadienylene is more preferred.

In the general formula (VI), $R^a$ is a saturated or unsaturated hydrocarbon group having 1 to 10 carbon atom. Specific examples of such unsaturated hydrocarbon groups may include alkyl groups such as methyl, ethyl, n-propyl, i-propyl, n-butyl, i-butyl, s-butyl, t-butyl, n-pentyl, n-hexyl, cyclopropyl or cyclopentyl; alkenyl groups such as vinyl, propenyl, butenyl, butadienyl, hexenyl or hexadienyl; aralkyl groups such as benzyl, phenylethyl or phenylpropyl; arylalkenyl groups such as trans-styryl; aryl groups such as phenyl, tolyl, dimethylphenyl, ethylphenyl, trimethylphenyl, 1-naphthyl or 2-naphthyl; or the like. Among them, methyl, ethyl, n-propyl, i-propyl, propenyl or butenyl are preferred.

In the general formula (VI), m and n are independently an integer of 0 to 20. The m and n are preferably an integer of 1 to 5. In the case where the m and/or n are an integer of 2 to 20, a plurality of $R^7$ (or a plurality of $R^8$) may be the same or different. However, in this case, m and n are not zero at the same time. In addition, when the m or n is an integer of not less than 2, $R^7$ or $R^8$ may be bonded to each other to form a ring. The position of $R^3$ to which the $R^7$ is bonded or the position of $R^6$ to which the $R^8$ is bonded is not particularly restricted, but it is preferred that the $R^7$ or the $R^8$ is bonded to a carbon atom of $R^3$ or $R^6$ adjacent to the 5-membered ring (carbon atom of α-position). The l is an integer of 0 to 22, preferably an integer of 1 to 10, more preferably an integer of 1 to 4. When the l is an integer of 2 to 22, a plurality of $R^a$ may be the same or different. Further, when the l is an integer of not less than 2, the $R^a$ may be bonded to each other to form a ring.

In the general formula (VI), X and Y are independently a hydrogen atom, a halogen atom, a hydrocarbon group having 1 to 20 carbon atoms, a halogenated hydrocarbon group having 1 to 20 carbon atoms, a silicon-containing hydrocarbon group having 1 to 20 carbon atoms, an oxygen-containing hydrocarbon group having 1 to 20 carbon atoms, an amino group or a nitrogen-containing hydrocarbon group having 1 to 20 carbon atoms. As the X and Y of the general formula (VI), there may be used the same groups as described for those of the general formula (II).

In the general formula (VI), M is a transition metal selected from the group consisting of elements belonging to Group 4–6 of the Periodic Table. As the M of the general formula (VI), there may be used the same transition metals as described for that of the general formula (II).

The novel transition metal compounds represented by the general formula (VI) can be produced by the same production method as used for the transition metal compound represented by the general formula (II). In this case, in the reaction scheme exemplified for the transition metal compound represented by the general formula (II), the $QCl_2$ is represented by the following general formula:

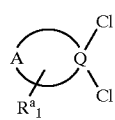

(QCl₂)

Specific examples of the transition metal compounds according to the present invention may include the below-mentioned compounds. Incidentally, although these compounds are indicated below merely by chemical names thereof, it is intended that each involves both compounds having symmetrical and asymmetrical stereo structures as mentioned above. First, for better understanding of nomenclatures of these transition metal compounds, the structural formula of zirconium chloride compound (1) is represented below. It should be noted that the zirconium chloride compound is also named as "methylene bis{1,1'-(2-methyl-4-phenyl-1,4-dihydroazulenyl)}zirconium dichloride, if the nomenclature derived from a compound before complexing thereof which has a skeleton of 1,4-dihydroazulene is considered.

(Chemical formula)

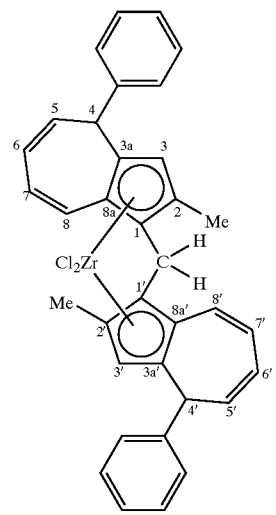

(1) methylene bis{1,1'-(2-methyl-4-phenyl-4-hydroazulenyl)}zirconium dichloride;
(2) methylene bis{1,1'-(4-hydroazulenyl)}zirconium dichloride;
(3) methylene bis{1,1'-(2-methyl-4-hydroazulenyl)}zirconium dichloride;
(4) methylene bis{1,1'-(2,4-dimethyl-4-hydroazulenyl)}zirconium dichloride;
(5) methylene bis{1,1'-2-ethyl-4-hydroazulenyl)}zirconium dichloride;
(6) methylene bis{1,1'-(2-ethyl-4-methyl-4-hydroazulenyl)}zirconium dichloride;
(7) methylene bis{1,1'-(2-ethyl-4-phenyl-4-hydroazulenyl)}zirconium dichloride;
(8) methylene bis{1,1'-(2,4,4-trimethyazulenyl)}zirconium dichloride;
(9) methylene bis{1,1'-(2-methyl-4,5,6,7,8-pentahydroazulenyl)}zirconium dichloride;
(10) methylene bis{1,1'-(2-methyl-4-phenyl-4,5,6,7,8-pentahydroazulenyl)}zirconium dichloride;
(11) methylene bis{1,1'-(4-methyl-4-hydroazulenyl)}zirconium dichloride;
(12) methylene bis{1,1'-(4-phenyl-4-hydroazulenyl)}zirconium dichloride;
(13) methylene bis{1,1'-(4-isopropyl-4-hydroazulenyl)}zirconium dichloride;
(14) methylene bis{1,1'-(4-naphthyl-4-hydroazulenyl)}zirconium dichloride;
(15) methylene bis{1,1'-(2-phenyl-4-hydroazulenyl)}zirconium dichloride;
(16) methylene bis{1,1'-(2-benzyl-4-hydroazulenyl)}zirconium dichloride;
(17) methylene bis{1,1'-(2-styryl-4-hydroazulenyl)}zirconium dichloride;
(18) methylene bis{1,1'-(2-t-butyl-4-hydroazulenyl)}zirconium dichloride;
(19) methylene bis(1,1'-cyclopentacyclooctenyl)zirconium dichloride;
(20) methylene bis{1,1'-(4-methylcyclopentacyclooctenyl)}zirconium dichloride;
(21) methylene bis{1,1'-(4-ethylcyclopentacyclooctenyl)}zirconium dichloride;
(22) methylene bis{(1,1'-(4-phenylcyclopentacyclooctenyl)}zirconium dichloride;
(23) methylene bis{1,1'-(2-ethyl-4-phenylcyclopentacyclooctenyl)}zirconium dichloride;

(24) methylene bis{1,1'-(4-methyl-4,5,6,7,8,9-hexahydrocyclopentacyclooctenyl)}zirconium dichloride;
(25) methylene bis(9-bicyclo[8.3.0]trideca-2-methylpentaenyl) zirconium dichloride;
(26) methylene bis(9-bicyclo[8.3.0]trideca-2,12-dimethylpentaenyl) zirconium dichloride;
(27) methylene bis(9-bicyclo[8.3.0]trideca-2,12-dimethyloctahydropentaenyl) zirconium dichloride;
(28) methylene bis(9-bicyclo[8.3.0]trideca-2-phenyl,12-ethylpentaenyl) zirconium dichloride;
(29) ethylene bis{1,1'-(4-hydroazulenyl)}zirconium dichloride;
(30) ethylene bis{1,1'-(2-methyl-4-hydroazulenyl)}zirconium dichloride;
(31) ethylene bis{1,1'-(2,4-dimethyl-4-hydroazulenyl)}zirconium dichloride;
(32) ethylene bis{1,1'-(2-methyl-4-phenyl-4-hydroazulenyl)}zirconium dichloride;
(33) ethylene bis{1,1'-(2-ethyl-4-hydroazulenyl)}zirconium dichloride;
(34) ethylene bis{1,1'-(2-ethyl-4-methyl-4-hydroazulenyl)}zirconium dichloride;
(35) ethylene bis{1,1'-(2-ethyl-4-phenyl-4-hydroazulenyl)}zirconium dichloride;
(36) ethylene bis{1,1'-(2,4,4-trimethylazulenyl)}zirconium dichloride;
(37) ethylene bis{1,1'-(2-methyl-4,5,6,7,8-pentahydroazulenyl)}zirconium dichloride;
(38) ethylene bis{1,1'-(2-methyl-4-phenyl-4,5,6,7,8-pentahydroazulenyl)}zirconium dichloride;
(39) ethylene bis{1,1'-(4-methyl-4-hydroazulenyl)}zirconium dichloride;
(40) ethylene bis{1,1'-(4-phenyl-4-hydroazulenyl)}zirconium dichloride;
(41) ethylene bis{1,1'-(4-isopropyl-4-hydroazulenyl)}zirconium dichloride;
(42) ethylene bis{1,1'-(4-naphthyl-4-hydroazulenyl)}zirconium dichloride;
(43) ethylene bis{1,1'-(2-phenyl-4-hydroazulenyl)}zirconium dichloride;
(44) ethylene bis{1,1'-(2-benzyl-4-hydroazulenyl)}zirconium dichloride;
(45) ethylene bis{1,1'-(2-styryl-4-hydroazulenyl)}zirconium dichloride;
(46) ethylene bis{1,1'-(2-t-butyl-4-hydroazulenyl)}zirconium dichloride;
(47) ethylene bis(1,1'-cyclopentacyclooctenyl) zirconium dichloride;
(48) ethylene bis{1,1'-(4-methylcyclopentacyclooctenyl)}zirconium dichloride;
(49) ethylene bis{1,1'-(4-ethylcyclopentacyclooctenyl)}zirconium dichloride;
(50) ethylene bis{1,1'-(4-phenylcyclopentacyclooctenyl)}zirconium dichloride;
(51) ethylene bis{1,1'-(2-ethyl-4-phenylcyclopentacyclooctenyl)}zirconium dichloride;
(52) ethylene bis{1,1'-(4-methyl-4,5,6,7,8,9-hexahydrocyclopentacyclooctenyl)}zirconium dichloride;
(53) ethylene bis(9-bicyclo[8.3.0]trideca-2-methylpentaenyl) zirconium dichloride;
(54) ethylene bis(9-bicyclo[8.3.0]trideca-2,12-dimethylpentaenyl) zirconium dichloride;
(55) ethylene bis(9-bicyclo[8.3.0]trideca-2,12-dimethyloctahydropentaenyl) zirconium dichloride;
(56) ethylene bis(9-bicyclo[8.3.0]trideca-2-phenyl,12-ethylpentaenyl) zirconium dichloride;
(57) ethylene(1-indenyl){1-(4-hydroazulenyl)}zirconium dichloride;
(58) ethylene{1-(2-methylindenyl)}{1-(2-methyl-4-hydroazulenyl)}zirconium dichloride;
(59) ethylene{1-(2-methyl-4,5-benzoindenyl)}{1-(2,4-dimethyl-4-hydroazulenyl)}zirconium dichloride;
(60) ethylene{1-(2-methyl-4-phenylindenyl)}{1-(2-methyl-4-phenyl-4-hydroazulenyl)}zirconium dichloride;
(61) ethylene{1-(2-ethyl-4-phenylindenyl)}{1-(2-ethyl-4-hydroazulenyl)}zirconium dichloride;
(62) ethylene{1-(2,4-dimethylcyclopentadienyl)}{1-(2-ethyl-4-methyl-4-hydroazulenyl)}zirconium dichloride;
(63) ethylene{1-(2-methyl-4,5-benzoindenyl)}{1-(2-ethyl-4-phenyl-4-hydroazulenyl)}zirconium dichloride;
(64) ethylene{1-(2-methyl-4-phenylindenyl)}{1-(2,4,4-trimethylazulenyl)}zirconium dichloride;
(65) ethylene{1-(2-methyltetrahydroindenyl)}{1-(2-methyl-4,5,6,7,8-pentahydroazulenyl)}zirconium dichloride;
(66) ethylene{1-(4-t-butyl-2-methylcyclopentadienyl)}{1-(2-methyl-4-phenyl-4,5,6,7,8-pentahydroazulenyl)}zirconium dichloride;
(67) ethylene{1-(2-ethyl-4-phenylindenyl)}{1-(4-methyl-4-hydroazulenyl)}zirconium dichloride;
(68) ethylene{1-(2-phenylindenyl)}{1-(4-phenyl-4-hydroazulenyl)}zirconium dichloride;
(69) ethylene{1-(2-propyl-4-phenylindenyl)}{1-(4-isopropyl-4-hydroazulenyl)}zirconium dichloride;
(70) ethylene{1-(2-t-butylindenyl)}{1-(4-naphthyl-4-hydroazulenyl)}zirconium dichloride;
(71) dimethylmethylene bis{1,1'-(4-hydroazulenyl)}zirconium dichloride;
(72) dimethylmethylene bis{1,1'-(2-methyl-4-hydroazulenyl)}zirconium dichloride;
(73) dimethylmethylene bis{1,1'-(2,4-dimethyl-4-hydroazulenyl)}zirconium dichloride;
(74) dimethylmethylene bis{1,1'-(2-methyl-4-phenyl-4-hydroazulenyl)}zirconium dichloride;
(75) dimethylmethylene bis{1,1'-(2-ethyl-4-hydroazulenyl)}zirconium dichloride;
(76) dimethylmethylene bis{1,1'-(2-ethyl-4-methyl-4-hydroazulenyl)}zirconium dichloride;
(77) dimethylmethylene bis{1,1'-(2-ethyl-4-phenyl-4-hydroazulenyl)}zirconium dichloride;
(78) dimethylmethylene bis{1,1'-(2,4,4-trimethylazulenyl)}zirconium dichloride;
(79) dimethylmethylene bis{1,1'-(2-methyl-4,5,6,7,8-pentahydroazulenyl)}zirconium dichloride;
(80) dimethylmethylene bis{1,1'-(2-methyl-4-phenyl-4,5,6,7,8-pentahydroazulenyl)}zirconium dichloride;
(81) dimethylmethylene bis{1,1'-(4-methyl-4-hydroazulenyl)}zirconium dichloride;
(82) dimethylmethylene bis{1,1'-(4-phenyl-4-hydroazulenyl)}zirconium dichloride;
(83) dimethylmethylene bis{1,1'-(4-isopropyl-4-hydroazulenyl)}zirconium dichloride;
(84) dimethylmethylene bis{1,1'-(4-naphthyl-4-hydroazulenyl)}zirconium dichloride;
(85) dimethylmethylene bis{1,1'-(2-phenyl-4-hydroazulenyl)}zirconium dichloride;
(86) dimethylmethylene bis{1,1'-(2-benzyl-4-hydroazulenyl)}zirconium dichloride;
(87) dimethylmethylene bis{1,1'-(2-styryl-4-hydroazulenyl)}zirconium dichloride;
(88) dimethylmethylene bis{1,1'-(2-t-butyl-4-hydroazulenyl)}zirconium dichloride;
(89) dimethylmethylene bis(1,1'-cyclopentacyclooctenyl) zirconium dichloride;

(90) dimethylmethylene bis{1,1'-(4-methylcyclopentacyclooctenyl)}zirconium dichloride;
(91) dimethylmethylene bis{1,1'-(4-ethylcyclopentacyclooctenyl)}zirconium dichloride;
(92) dimethylmethylene bis{1,1'-(4-phenylcyclopentacyclooctenyl)}zirconium dichloride;
(93) dimethylmethylene bis{1,1'-(2-ethyl-4-phenylcyclopentacyclooctenyl)}zirconium dichloride;
(94) dimethylmethylene bis{1,1'-(4-methyl-4,5,6,7,8,9-hexahydrocyclopentacyclooctenyl)}zirconium dichloride;
(95) dimethylmethylene bis(9-bicyclo[8.3.0]trideca-2-methyl pentaenyl) zirconium dichloride;
(96) dimethylmethylene bis(9-bicyclo[8.3.0]trideca-2,12-dimethylpentaenyl) zirconium dichloride;
(97) dimethylmethylene bis(9-bicyclo[8.3.0]trideca-2,12-dimethyloctahydropentaenyl) zirconium dichloride;
(98) dimethylmethylene bis(9-bicyclo[8.3.0]trideca-2-phenyl, 12-ethylpentaenyl) zirconium dichloride;
(99) dimethylmethylene(1-indenyl)}{1-(4-hydroazulenyl)}zirconium dichloride;
(100) dimethylmethylene{1-(2-methylindenyl)}{1-(2-methyl-4-hydroazulenyl)}zirconium dichloride;
(101) dimethylmethylene{1-(2-methyl-4,5-benzoindenyl)}{1-(2,4-dimethyl-4-hydroazulenyl)}zirconium dichloride;
(102) dimethylmethylene{1-(2-methyl-4-phenylindenyl)}{1-(2-methyl-4-phenyl-4-hydroazulenyl)}zirconium dichloride;
(103) dimethylmethylene{1-(2-ethyl-4-phenylindenyl)}{1-(2-ethyl-4-hydroazulenyl)}zirconium dichloride;
(104) dimethylmethylene{1-(2,4-dimethylcyclopentadienyl)}{1-(2-ethyl-4-methyl-4-hydroazulenyl)}zirconium dichloride;
(105) dimethylmethylene{1-(2-methyl-4,5-benzoindenyl)}{1-(2-ethyl-4-phenyl-4-hydroazulenyl)}zirconium dichloride;
(106) dimethylmethylene{1-(2-methyl-4-phenylindenyl)}{1-(2,4,4-trimethylazulenyl)}zirconium dichloride;
(107) dimethylmethylene{1-(2-methyltetrahydroindenyl)}{1-(2-methyl-4,5,6,7,8-pentahydroazulenyl)}zirconium dichloride;
(108) dimethylmethylene{1-(4-t-butyl-2-methylcyclopentadienyl)}{1-(2-methyl-4-phenyl-4,5,6,7,8-pentahydroazulenyl)}zirconium dichloride;
(109) dimethylmethylene{1-(2-ethyl-4-phenylindenyl)}{1-(4-methyl-4-hydroazulenyl)}zirconium dichloride;
(110) dimethylmethylene{1-(2-phenylindenyl)}{1-(4-phenyl-4-hydroazulenyl)}zirconium dichloride;
(111) dimethylmethylene{1-(2-propyl-4-phenylindenyl)}{1-(4-isopropyl-4-hydroazulenyl)}zirconium dichloride;
(112) dimethylmethylene{1-(2-t-butylindenyl)}{1-(4-naphthyl-4-hydroazulenyl)}zirconium dichloride;
(113) 2,3-butylene bis{1,1'-(2-methyl-4-phenyl-4-hydroazulenyl)}zirconium dichloride;
(114) dimethylsilylene bis{1,1'-(4-hydroazulenyl)}zirconium dichloride;
(115) dimethylsilylene bis{1,1'-(2-methyl-4-hydroazulenyl)}zirconium dichloride;
(116) dimethylsilylene bis{1,1'-(2,4-dimethyl-4-hydroazulenyl)}zirconium dichloride;
(117) dimethylsilylene bis{1,1'-(2-methyl-4-phenyl-4-hydroazulenyl)}zirconium dichloride;
(118) dimethylsilylene bis{1,1'-(2-ethyl-4-hydroazulenyl)}zirconium dichloride;
(119) dimethylsilylene bis{1,1'-(2-ethyl-4-methyl-4-hydroazulenyl)}zirconium dichloride;
(120) dimethylsilylene bis{1,1'-(2-ethyl-4-phenyl-4-hydroazulenyl)}zirconium dichloride;
(121) dimethylsilylene bis{1,1'-(2,4,4-trimethylazulenyl)}zirconium dichloride;
(122) dimethylsilylene bis{1,1'-(2-methyl-4,5,6,7,8-pentahydroazulenyl)}zirconium dichloride;
(123) dimethylsilylene bis{1,1'-(2-methyl-4-phenyl-4,5,6,7,8-pentahydroazulenyl)}zirconium dichloride;
(124) dimethylsilylene bis{1,1'-(4-methyl-4-hydroazulenyl)}zirconium dichloride;
(125) dimethylsilylene bis{1,1'-(4-phenyl-4-hydroazulenyl)}zirconium dichloride;
(126) dimethylsilylene bis{1,1'-(4-isopropyl-4-hydroazulenyl)}zirconium dichloride;
(127) dimethylsilylene bis{1,1'-(4-naphthyl-4-hydroazulenyl)}zirconium dichloride;
(128) dimethylsilylene bis{1,1'-(2-phenyl-4-hydroazulenyl)}zirconium dichloride;
(129) dimethylsilylene bis{1,1'-(2-benzyl-4-hydroazulenyl)}zirconium dichloride;
(130) dimethylsilylene bis{1,1'-(2-styryl-4-hydroazulenyl)}zirconium dichloride;
(131) dimethylsilylene bis{1,1'-(2-t-butyl-4-hydroazulenyl)}zirconium dichloride;
(132) dimethylsilylene bis(1,1'-cyclopentacyclooctenyl) zirconium dichloride;
(133) dimethylsilylene bis{1,1'-(4-methylcyclopentacyclooctenyl)}zirconium dichloride;
(134) dimethylsilylene bis{1,1'-(4-ethylcyclopentacyclooctenyl)}zirconium dichloride;
(135) dimethylsilylene bis{1,1'-(4-phenylcyclopentacyclooctenyl)}zirconium dichloride;
(136) dimethylsilylene bis{1,1'-(2-ethyl-4-phenylcyclopentacyclooctenyl)}zirconium dichloride;
(137) dimethylsilylene bis{1,1'-(4-methyl-4,5,6,7,8,9-hexahydrocyclopentacyclooctenyl)}zirconium dichloride;
(138) dimethylsilylene bis(9-bicyclo[8.3.0]trideca-2-methylpentaenyl) zirconium dichloride;
(139) dimethylsilylene bis(9-bicyclo[8.3.0]trideca-2,12-dimethylpentaenyl) zirconium dichloride;
(140) dimethylsilylene bis(9-bicyclo[8.3.0]trideca-2,12-dimethyloctahydropentaenyl) zirconium dichloride;
(141) dimethylsilylene bis(9-bicyclo[8.3.0]trideca-2-phenyl,12-ethylpentaenyl)zirconium dichloride;
(142) dimethylsilylene(1-indenyl){1-(4-hydroazulenyl)}zirconium dichloride;
(143) dimethylsilylene{1-(2-methylindenyl)}{1-(2-methyl-4-hydroazulenyl)}zirconium dichloride;
(144) dimethylsilylene{1-(2-methyl-4,5-benzoindenyl)}{1-(2,4-dimethyl-4-hydroazulenyl)}zirconium dichloride;
(145) dimethylsilylene{1-(2-methyl-4-phenylindenyl)}{1-(2-methyl-4-phenyl-4-hydroazulenyl)}zirconium dichloride;
(146) dimethylsilylene{1-(2-ethyl-4-phenylindenyl)}{1-(2-ethyl-4-hydroazulenyl)}zirconium dichloride;
(147) dimethylsilylene{1-(2,4-dimethylcyclopentadienyl)}{1-(2-ethyl-4-methyl-4-hydroazulenyl)}zirconium dichloride;
(148) dimethylsilylene{1-(2-methyl-4,5-benzoindenyl)}{1-(2-ethyl-4-phenyl-4-hydroazulenyl)}zirconium dichloride;
(149) dimethylsilylene{1-(2-methyl-4-phenylindenyl)}{1-(2,4,4-trimethylazulenyl)}zirconium dichloride;
(150) dimethylsilylene{1-(2-methyltetrahydroindenyl)}{1-(2-methyl-4,5,6,7,8-pentahydroazulenyl)}zirconium dichloride;

(151) dimethylsilylene{1-(4-t-butyl-2-methylcyclopentadienyl)}{1-(2-methyl-4-phenyl-4,5,6,7,8-pentahydroazulenyl)}zirconium dichloride;
(152) dimethylsilylene{1-(2-ethyl-4-phenylindenyl)}{1-(4-methyl-4-hydroazulenyl)}zirconium dichloride;
(153) dimethylsilylene{1-(2-phenylindenyl)}{1-(4-phenyl-4-hydroazulenyl)}zirconium dichloride;
(154) dimethylsilylene{1-(2-propyl-4-phenylindenyl)}{1-(4-isopropyl-4-hydroazulenyl)}zirconium dichloride;
(155) dimethylsilylene{1-(2-t-butylindenyl)}{1-(4-naphthyl-4-hydroazulenyl)}zirconium dichloride;
(156) (methyl)(phenyl)silylene bis{1,1'-(4-hydroazulenyl)}zirconium dichloride;
(157) (methyl)(phenyl)silylene bis{1,1'-(2-methyl-4-hydroazulenyl)}zirconium dichloride;
(158) (methyl)(phenyl)silylene bis{1,1'-(2,4-dimethyl-4-hydroazulenyl)}zirconium dichloride;
(159) (methyl)(phenyl)silylene bis{1,1'-(2-methyl-4-phenyl-4-hydroazulenyl)}zirconium dichloride;
(160) (methyl)(phenyl)silylene bis{1,1'-(2-ethyl-4-hydroazulenyl)}zirconium dichloride;
(161) (methyl)(phenyl)silylene bis{1,1'-(2-ethyl-4-methyl-4-hydroazulenyl)}zirconium dichloride;
(162) (methyl)(phenyl)silylene bis{1,1'-(2-ethyl-4-phenyl-4-hydroazulenyl)}zirconium dichloride;
(163) (methyl)(phenyl)silylene bis{1,1'-(2,4,4-trimethylazulenyl)}zirconium dichloride;
(164) (methyl)(phenyl)silylene bis{1,1'-(2-methyl-4,5,6,7,8-pentahydroazulenyl)}zirconium dichloride;
(165) (methyl)(phenyl)silylene bis{1,1'-(2-methyl-4-phenyl-4,5,6,7,8-pentahydroazulenyl)}zirconium dichloride;
(166) diphenylsilylene bis{1,1'-(4-hydroazulenyl)}zirconium dichloride;
(167) diphenylsilylene bis{1,1'-(2-methyl-4-hydroazulenyl)}zirconium dichloride;
(168) diphenylsilylene bis{1,1'-(2, 4-dimethyl-4-hydroazulenyl)}zirconium dichloride;
(169) diphenylsilylene bis{1,1'-(2-methyl-4-phenyl-4-hydroazulenyl)}zirconium dichloride;
(170) diphenylsilylene bis{1,1'-(2-ethyl-4-hydroazulenyl)}zirconium dichloride;
(171) diphenylsilylene bis{1,1'-(2-ethyl-4-methyl-4-hydroazulenyl)}zirconium dichloride;
(172) diphenylsilylene bis{1,1'-(2-ethyl-4-phenyl-4-hydroazulenyl)}zirconium dichloride;
(173) diphenylsilylene bis{1,1'-(2,4,4-trimethylzulenyl)}zirconium dichloride;
(174) diphenylsilylene bis{1,1'-(2-methyl-4,5,6,7,8-pentahydroazulenyl)}zirconium dichloride;
(175) diphenylsilylene bis{1,1'-(2-methyl-4-phenyl-4,5,6,7,8-pentahydroazulenyl)}zirconium dichloride;
(176) tetramethyldisilylene bis{1,1'-(4-hydroazulenyl)}zirconium dichloride;
(177) tetramethyldisilylene bis{1,1'-(2-methyl-4-hydroazulenyl)}zirconium dichloride;
(178) tetramethyldisilylene bis{1,1'-(2, 4-dimethyl-4-hydroazulenyl)}zirconium dichloride;
(179) tetramethyldisilylene bis{1,1'-(2-methyl-4-phenyl-4-hydroazulenyl)}zirconium dichloride;
(180) tetramethyldisilylene bis{1,1'-(2-ethyl-4-hydroazulenyl)}zirconium dichloride;
(181) tetramethyldisilylene bis{1,1'-(2-ethyl-4-methyl-4-hydroazulenyl)}zirconium dichloride;
(182) tetramethyldisilylene bis{1,1'-(2-ethyl-4-phenyl-4-hydroazulenyl)}zirconium dichloride;
(183) tetramethyldisilylene bis{1,1'-(2,4,4-trimethylazulenyl)}zirconium dichloride;
(184) tetramethyldisilylene bis{1,1'-(2-methyl-4,5,6,7,8-pentahydroazulenyl)}zirconium dichloride;
(185) tetramethyldisilylene bis{1,1'-(2-methyl-4-phenyl-4,5,6,7,8-pentahydroazulenyl)}zirconium dichloride;
(186) dimethylgermylene bis{1,1'-(4-hydroazulenyl)}zirconium dichloride;
(187) dimethylgermylene bis{1,1'-(2-methyl-4-hydroazulenyl)}zirconium dichloride;
(188) dimethylgermylene bis{1,1'-(2,4-dimethyl-4-hydroazulenyl)}zirconium dichloride;
(189) dimethylgermylene bis{1,1'-(2-methyl-4-phenyl-4-hydroazulenyl)}zirconium dichloride;
(190) dimethylgermylene bis{1,1'-(2-ethyl-4-hydroazulenyl)}zirconium dichloride;
(191) dimethylgermylene bis{1,1'-(2-ethyl-4-methyl-4-hydroazulenyl)}zirconium dichloride;
(192) dimethylgermylene bis{1,1'-(2-ethyl-4-phenyl-4-hydroazulenyl)}zirconium dichloride;
(193) dimethylgermylene bis{1,1'-(2,4,4-trimethylazulenyl)}zirconium dichloride;
(194) dimethylgermylene bis{1,1'-(2-methyl-4,5,6,7,8-pentahydroazulenyl)}zirconium dichloride;
(195) dimethylgermylene bis{1,1'-(2-methyl-4-phenyl-4,5,6,7,8-pentahydroazulenyl)}zirconium dichloride;
(196) dimethylsilylene bis{1,1'-(2-trifluoromethyl-4-phenyl-4-hydroazulenyl)}zirconium dichloride;
(197) dimethylsilylene bis{1,1'-(2-ethyl-4-indolyl-4-hydroazulenyl)}zirconium dichloride;
(198) dimethylsilylene bis{1,1'-(2-ethyl-4-phenoxy-4-hydroazulenyl)}zirconium dichloride;
(199) dimethylsilylene bis{1,1'-(2-fluoro-4-pyrazolyl-4-hydroazulenyl)}zirconium dichloride;
(200) silacyclohexylidene bis{1,1'-(2-methyl-4-phenyl-4-hydroazulenyl)}zirconium dichloride;
(201) cyclohexylidene bis{1,1'-(2-methyl-4-furyl-4-hydroazulenyl)}zirconium dichloride.
(202) dimethylsilylene bis{1,1'-(2-benzyl-4-phenyl-4,5,6,7,8-pentahydroazulenyl)}zirconium dichloride;
(203) dimethylsilylene bis[1,1'-{2-benzyl-4-(4-chlorophenyl)-4,5,6,7,8-pentahydroazulenyl}] zirconium dichloride;
(204) dimethylsilylene bis[1,1'-{2-benzyl-4-(4-fluorophenyl)-4,5,6,7,8-pentahydroazulenyl}] zirconium dichloride;
(205) dimethylsilylene bis[1,1'-{2-benzyl-4-(1-naphthyl)-4,5,6,7,8-pentahydroazulenyl}] zirconium dichloride;
(206) dimethylsilylene bis[1,1'-{2-benzyl-4-(2-naphthyl)-4,5,6,7,8-pentahydroazulenyl}] zirconium dichloride;
(207) dimethylsilylene bis{1,1'-(2-benzyl-4-phenyl-7-isopropyl-4,5,6,7,8-pentahydroazulenyl)}zirconium dichloride;
(208) dimethylsilylene bis[1,1'-{2-(1-phenylethyl)-4-phenyl-4,5,6,7,8-pentahydroazulenyl)}zirconium dichloride;
(209) dimethylsilylene bis[1,1'-{2-(1-phenylethyl)-4-phenyl-7-isopropyl-4,5,6,7,8-pentahydroazulenyl)}zirconium dichloride;
(210) 9-silafluorene-9,9-diyl bis{1,1'-(2-methyl-4-phenyl-4,5,6,7,8-pentahydroazulenyl)}zirconium dichloride;
(211) 1-silaindene-1,1-diyl bis{1,1'-(2-methyl-4-phenyl-4,5,6,7,8-pentahydroazulenyl)}zirconium dichloride;
(212) tetramethyl-1-silacyclopentadiene-1,1-diyl bis{1,1'-(2-methyl-4-phenyl-4,5,6,7,8-pentahydroazulenyl)}zirconium dichloride;
(213) 1-silacyclo-3-pentene-1,1-diyl bis{1,1'-(2-methyl-4-phenyl-4,5,6,7,8-pentahydroazulenyl)}zirconium dichloride;

(214) dimethylmethylene bis[1,1'-{2-methyl-4-(4-fluorophenyl)-4-hydroazulenyl}] zirconium dichloride;
(215) dimethylmethylene bis[1,1'-{2-methyl-4-(4-chlorophenyl)-4-hydroazulenyl}] zirconium dichloride;
(216) dimethylmethylene bis[1,1'-{2-methyl-4-(4-trifluoromethylphenyl)-4-hydroazulenyl}] zirconium dichloride;
(217) ethylene bis[1,1'-{2-methyl-4-(4-fluorophenyl)-4-hydroazulenyl}] zirconium dichloride;
(218) ethylene bis[1,1'-{2-methyl-4-(4-chlorophenyl)-4-hydroazulenyl}] zirconium dichloride;
(219) ethylene bis[1,1'-{2-methyl-4-(4-trifluoromethylphenyl)-4-hydroazulenyl}] zirconium dichloride;
(220) trimethylene bis[1,1'-{2-methyl-4-(4-fluorophenyl)-4-hydroazulenyl}] zirconium dichloride;
(221) trimethylene bis[1,1'-{2-methyl-4-(4-chlorophenyl)-4-hydroazulenyl)}] zirconium dichloride;
(222) trimethylene bis[1,1'-{2-methyl-4-(4-trifluoromethylphenyl)-4-hydroazulenyl}] zirconium dichloride;
(223) dimethylsilylene bis{1,1'-(2-methyl-4-trifluoromethyl-4-hydroazulenyl}] zirconium dichloride;
(224) dimethylsilylene bis[1,1'-{2-methyl-4-(2-fluorophenyl)-4-hydroazulenyl}] zirconium dichloride;
(225) dimethylsilylene bis[1,1'-{2-methyl-4-(3-fluorophenyl)-4-hydroazulenyl}] zirconium dichloride;
(226) dimethylsilylene bis[1,1'-{2-methyl-4-(4-fluorophenyl)-4-hydroazulenyl}] zirconium dichloride;
(227) dimethylsilylene bis[1,1'-{2-ethyl-4-(4-fluorophenyl)-4-hydroazulenyl}] zirconium dichloride;
(228) dimethylsilylene bis[1,1'-{2-methyl-4-(2-chlorophenyl)-4-hydroazulenyl}] zirconium dichloride;
(229) dimethylsilylene bis[1,1'-{2-methyl-4-(3-chlorophenyl)-4-hydroazulenyl}] zirconium dichloride;
(230) dimethylsilylene bis[1,1'-{2-methyl-4-(4-chlorophenyl)-4-hydroazulenyl}] zirconium dichloride;
(231) dimethylsilylene bis[1,1'-{2-ethyl-4-(4-chlorophenyl)-4-hydroazulenyl}] zirconium dichloride;
(232) dimethylsilylene bis[1,1'-{2-methyl-4-(2-trifluoromethylphenyl)-4-hydroazulenyl}] zirconium dichloride;
(233) dimethylsilylene bis[1,1'-{2-methyl-4-(3-trifluoromethylphenyl)-4-hydroazulenyl}] zirconium dichloride;
(234) dimethylsilylene bis[1,1'-{2-methyl-4-(4-trifluoromethylphenyl)-4-hydroazulenyl}] zirconium dichloride;
(235) dimethylsilylene bis[1,1'-{2-ethyl-4-(4-trifluoromethylphenyl)-4-hydroazulenyl}] zirconium dichloride;
(236) dimethylsilylene bis[1,1'-{2-methyl-4-(2,4-difluorophenyl)-4-hydroazulenyl}] zirconium dichloride;
(237) dimethylsilylene bis[1,1'-{2-methyl-4-(2,5-difluorophenyl)-4-hydroazulenyl}] zirconium dichloride;
(238) dimethylsilylene bis[1,1'-{2-methyl-4-(2,6-difluorophenyl)-4-hydroazulenyl}] zirconium dichloride;
(239) dimethylsilylene bis[1,1'-{2-methyl-4-(3,5-difluorophenyl)-4-hydroazulenyl}] zirconium dichloride;
(240) dimethylsilylene bis[1,1'-{2-methyl-4-(2,4,6-trifluorophenyl)-4-hydroazulenyl}] zirconium dichloride;
(241) dimethylsilylene[1-{2-methyl-4-(4-fluorophenyl)-4-hydroazulenyl}][1-{2-methyl-4-(4-chlorophenyl)-4-hydroazulenyl}] zirconium dichloride;
(242) dimethylsilylene bis[1,1'-{2-methyl-4-(4-fluorophenyl)-6-isopropyl-4-hydroazulenyl}] zirconium dichloride;
(243) dimethylsilylene bis[1,1'-{2,8-dimethyl-4-(4-fluorophenyl)-4-hydroazulenyl}] zirconium dichloride;
(244) dimethylsilylene bis[1,1'-{2-methyl-4-(4-chlorophenyl)-6-isopropyl-4-hydroazulenyl}] zirconium dichloride;
(245) dimethylsilylene bis[1,1'-{2-methyl-4-(4-chlorophenyl)-7-isopropyl-4-hydroazulenyl}] zirconium dichloride;
(246) dimethylsilylene bis[1,1'-{2,8-dimethyl-4-(4-chlorophenyl)-4-hydroazulenyl}] zirconium dichloride;
(247) dimethylsilylene bis[1,1'-{2-methyl-4-(4-trifluoromethylphenyl)-6-isopropyl-4-hydroazulenyl}] zirconium dichloride;
(248) dimethylsilylene bis[1,1'-{2-methyl-4-(4-trifluoromethylphenyl)-7-isopropyl-4-hydroazulenyl}] zirconium dichloride;
(249) dimethylsilylene bis[1,1'-{2-methyl-4-(4-fluorophenyl)-7-isopropyl-4-hydroazulenyl}] zirconium dichloride;
(250) dimethylsilylene bis[1,1'-{2-ethyl-4-(4-chlorophenyl)-7-isopropyl-4-hydroazulenyl}] zirconium dichloride;
(251) dimethylsilylene bis[1,1'-{2-ethyl-4-(4-fluorophenyl)-7-isopropyl-4-hydroazulenyl}] zirconium dichloride;
(252) dimethylsilylene bis[1,1'-{2-ethyl-4-(4-trifluoromethyl phenyl)-7-isopropyl-4-hydroazulenyl}] zirconium dichloride;
(253) dimethylsilylene bis[1,1'-{2-ethyl-4-(4-chlorophenyl)-7-phenyl-4-hydroazulenyl}] zirconium dichloride;
(254) dimethylsilylene bis[1,1'-{2-ethyl-4-(4-fluorophenyl)-7-phenyl-4-hydroazulenyl}] zirconium dichloride;
(255) dimethylsilylene bis[1,1'-{2-ethyl-4-(4-trifluoromethyl phenyl)-7-phenyl-4-hydroazulenyl}] zirconium dichloride;
(256) diphenylsilylene bis[1,1'-{2-ethyl-4-(4-chlorophenyl)-7-isopropyl-4-hydroazulenyl}] zirconium dichloride;
(257) diphenylsilylene bis[1,1'-{2-ethyl-4-(4-fluorophenyl)-7-isopropyl-4-hydroazulenyl}] zirconium dichloride;
(258) diphenylsilylene bis[1,1'-{2-ethyl-4-(4-trifluoromethyl phenyl)-7-isopropyl-4-hydroazulenyl}] zirconium dichloride;
(259) (methyl)(phenyl)silylene bis[1,1'-{2-ethyl-4-(4-chlorophenyl)-7-isopropyl-4-hydroazulenyl}] zirconium dichloride;
(260) (methyl)(phenyl)silylene bis[1,1'-{2-ethyl-4-(4-fluorophenyl)-7-isopropyl-4-hydroazulenyl}] zirconium dichloride;
(261) (methyl)(phenyl)silylene bis[1,1'-{2-ethyl-4-(4-trifluoromethylphenyl)-7-isopropyl-4-hydroazulenyl}] zirconium dichloride;
(262) dimethylsilylene bis[1,1'-{2-ethyl-4-(4-chlorophenyl)-7-isopropyl-4,5,6,7,8-pentahydroazulenyl}] zirconium dichloride;
(263) dimethylsilylene bis[1,1'-{2-ethyl-4-(4-fluorophenyl)-7-isopropyl-4,5,6,7,8-pentahydroazulenyl}] zirconium dichloride;
(264) dimethylsilylene bis[1,1'-{2-ethyl-4-(4-trifluoromethyl phenyl)-7-isopropyl-4,5,6,7,8-pentahydroazulenyl}] zirconium dichloride;
(265) dimethylsilylene[1-{2-ethyl-4-(4-chlorophenyl)-7-isopropyl-4-hydroazulenyl}]{1-(2-methyl-4,5-benzoindenyl)}zirconium dichloride;
(266) dimethylsilylene[1-{2-ethyl-4-(4-fluorophenyl)-7-isopropyl-4-hydroazulenyl}]{1-(2-methyl-4,5-benzoindenyl)}zirconium dichloride;
(267) dimethylsilylene[1-{2-ethyl-4-(4-trifluoromethyl phenyl)-7-isopropyl-4-hydroazulenyl}]{1-(2-methyl-4,5-benzoindenyl)}zirconium dichloride;
(268) dimethylsilylene[1-{2-ethyl-4-(4-chlorophenyl)-7-isopropyl-4-hydroazulenyl}]{1-(2-methyl-4-phenylindenyl)}zirconium dichloride;

(269) dimethylsilylene[1-{2-ethyl-4-(4-fluorophenyl)-7-isopropyl-4-hydroazulenyl}]{1-(2-methyl-4-phenylindenyl)}zirconium dichloride;
(270) dimethylsilylene[1-{2-ethyl-4-(4-trifluoromethylphenyl)-7-isopropyl-4-hydroazulenyl}]{1-(2-methyl-4-phenylindenyl)}zirconium dichloride;
(261) dimethylsilylene bis[1,1'-{2-benzyl-4-(4-chlorophenyl)-4-hydroazulenyl)}zirconium dichloride;
(272) dimethylsilylene bis[1,1'-{2-benzyl-4-(4-fluorophenyl)-4-hydroazulenyl)}zirconium dichloride;
(273) dimethylsilylene bis[1,1'-{2-benzyl-4-(4-chlorophenyl)-7-isopropyl-4-hydroazulenyl)}zirconium dichloride;
(274) dimethylsilylene bis[1,1'-{2-benzyl-4-(4-fluorophenyl)-7-isopropyl-4-hydroazulenyl)}zirconium dichloride;
(275) diphenylsilylene bis[1,1'-{2-benzyl-4-(4-chlorophenyl)-4-hydroazulenyl)}zirconium dichloride;
(276) diphenylsilylene bis[1,1'-{2-benzyl-4-(4-fluorophenyl)-4-hydroazulenyl)}zirconium dichloride;
(277) (methyl)(phenyl)silylene bis[1,1'-{2-benzyl-4-(4-chlorophenyl)-4-hydroazulenyl)}zirconium dichloride;
(278) (methyl)(phenyl)silylene bis[1,1'-{2-benzyl-4-(4-fluorophenyl)-4-hydroazulenyl)}zirconium dichloride;
(279) dimethylsilylene[1-{2-benzyl-4-(4-chlorophenyl)-4-hydroazulenyl}]{1-(2-methyl-4,5-benzoindenyl)}zirconium dichloride;
(280) dimethylsilylene[1-{2-benzyl-4-(4-fluorophenyl)-4-hydroazulenyl}]{1-(2-methyl-4,5-benzoindenyl)}zirconium dichloride;
(281) dimethylsilylene[1-{2-benzyl-4-(4-chlorophenyl)-4-hydroazulenyl}]{1-(2-methyl-4-phenylindenyl)}zirconium dichloride;
(282) dimethylsilylene[1-{2-benzyl-4-(4-fluorophenyl)-4-hydroazulenyl}]{1-(2-methyl-4-phenylindenyl)}zirconium dichloride;
(283) dimethylsilylene bis[1'-{2,8-dimethyl-4-(4-trifluoromethylphenyl)-4-hydroazulenyl}] zirconium dichloride;
(284) dimethylsilylene bis[1,1'-{2-methyl-4-(4-fluoro-1-naphthyl)-4-hydroazulenyl}] zirconium dichloride;
(285) dimethylsilylene bis[1,1'-{2-methyl-4-(4-fluoro-2-naphthyl)-4-hydroazulenyl}] zirconium dichloride;
(286) (methyl)(phenyl)silylene bis[1,1'-{2-methyl-4-(4-fluorophenyl)-4-hydroazulenyl}] zirconium dichloride;
(287) (methyl)(phenyl)silylene bis[1,1'-{2-methyl-4-(4-chlorophenyl)-4-hydroazulenyl}] zirconium dichloride;
(288) (methyl)(phenyl)silylene bis[1,1'-{2-methyl-4-(4-trifluoromethylphenyl)-4-hydroazulenyl}] zirconium dichloride;
(289) diphenylsilylene bis[1,1'-{2-methyl-4-(4-fluorophenyl)-4-hydroazulenyl}] zirconium dichloride;
(290) diphenylsilylene bis[1,1'-{2-methyl-4-(4-chlorophenyl)-4-hydroazulenyl}] zirconium dichloride;
(291) diphenylsilylene bis[1,1'-{2-methyl-4-(4-trifluoromethylphenyl)-4-hydroazulenyl}] zirconium dichloride;
(292) dimethylgermylene bis[1,1'-{2-methyl-4-(4-fluorophenyl)-4-hydroazulenyl}] zirconium dichloride;
(293) dimethylgermylene bis[1,1'-{2-methyl-4-(4-chlorophenyl)-4-hydroazulenyl}] zirconium dichloride;
(294) dimethylgermylene bis[1,1'-{2-methyl-4-(4-trifluoromethylphenyl)-4-hydroazulenyl}] zirconium dichloride;
(295) dimethylsilylene[1-{2-methyl-4-(4-fluorophenyl)-4-hydroazulenyl}]{1-(2-methyl-4-phenyl-4-hydroazulenyl)}zirconium dichloride;
(296) dimethylsilylene[1-{2-ethyl-4-(4-fluorophenyl)-4-dihydroazulenyl}]{1-(2-ethyl-4-phenyl-4-hydroazulenyl)}zirconium dichloride;
(297) dimethylsilylene[1-{2-methyl-4-(4-chlorophenyl)-4-hydroazulenyl}]{1-(2-methyl-4-phenyl-4-hydroazulenyl)}zirconium dichloride;
(298) dimethylsilylene[1-{2-methyl-4-(4-trifluoromethylphenyl)-4-hydroazulenyl}]{1-(2-methyl-4-phenyl-4-hydroazulenyl)}zirconium dichloride;
(299) dimethylsilylene[1-{2-methyl-4-(4-fluorophenyl)-4-hydroazulenyl}]{1-(2-methyl-4-phenyl-4,5,6,7,8-pentahydroazulenyl)}zirconium dichloride;
(300) dimethylsilylene[1-{2-methyl-4-(4-fluorophenyl)-4-hydroazulenyl}]{1-(2-methyl-4-(4-fluorophenyl)-4,5,6,7,8-pentahydroazulenyl)}zirconium dichloride;
(301) dimethylsilylene[1-{2-ethyl-4-(4-fluorophenyl)-4-hydroazulenyl}]{1-(2-ethyl-4-phenyl-4,5,6,7,8-pentahydroazulenyl)}zirconium dichloride;
(302) dimethylsilylene[1-{2-methyl-4-(4-chlorophenyl)-4-hydroazulenyl}]{1-(2-methyl-4-phenyl-4,5,6,7,8-pentahydroazulenyl)}zirconium dichloride;
(303) dimethylsilylene[1-{2-methyl-4-(4-trifluoromethylphenyl)-4-hydroazulenyl}]{1-(2-methyl-4-phenyl-4,5,6,7,8-pentahydroazulenyl)}zirconium dichloride;
(304) dimethylsilylene[1-{2-methyl-4-(4-fluorophenyl)-4-hydroazulenyl}]{1-(2-methyl-4-phenylindenyl)}zirconium dichloride;
(305) dimethylsilylene[1-{2-ethyl-4-(4-fluorophenyl)-4-hydroazulenyl}]{1-(2-ethyl-4-phenylindenyl)}zirconium dichloride;
(306) dimethylsilylene[1-{2-methyl-4-(4-chlorophenyl)-4-hydroazulenyl}]{1-(2-methyl-4-phenylindenyl)}zirconium dichloride;
(307) dimethylsilylene[1-{2-methyl-4-(4-trifluoromethylphenyl)-4-hydroazulenyl}]{1-(2-methyl-4-phenylindenyl)}zirconium dichloride;
(308) dimethylsilylene[1-{2-methyl-4-(4-trifluoromethylphenyl)-4-hydroazulenyl}]{1-(2-methyl-4,5-benzoindenyl)}zirconium dichloride;
(309) dimethylsilylene[1-{2-methyl-4-(4-fluorophenyl)-4-hydroazulenyl}]{1-(2-methyl-4,5-benzoindenyl)}zirconium dichloride;
(310) dimethylsilylene[1-{2-methyl-4-(4-chlorophenyl)-4-hydroazulenyl}]{1-(2-methyl-4,5-benzoindenyl)}zirconium dichloride;
(311) dimethylsilylene[1-{2-methyl-4-(4-chlorophenyl)-4,5,6,7,8-pentahydroazulenyl}]{1-(2-methyl-4-phenylindenyl)}zirconium dichloride;
(312) dimethylsilylene[1-{2-methyl-4-(4-fluorophenyl)indenyl}]{1-(2-methyl-4-phenyl-4-hydroazulenyl)}zirconium dichloride;
(313) dimethylsilylene[1-{2-ethyl-4-(4-fluorophenyl)indenyl}]{1-(2-ethyl-4-phenyl-4-hydroazulenyl)}zirconium dichloride;
(314) dimethylsilylene[1-{2-methyl-4-(4-chlorophenyl)indenyl}]{1-(2-methyl-4-phenyl-4-hydroazulenyl)}zirconium dichloride;
(315) dimethylsilylene[1-{2-methyl-4-(4-trifluoromethylphenyl)indenyl}]{1-(2-methyl-4-phenyl-4-hydroazulenyl)}zirconium dichloride;
(316) dimethylsilylene[1-{2-methyl-4-(4-trifluoromethylphenyl)indenyl}][1-{2-methyl-4-(4-chlorophenyl)-4-hydroazulenyl]zirconium dichloride;
(317) dimethylsilylene bis[1,1'-{2-methyl-4-(4-fluorophenyl)cyclopentacyclooctenyl}zirconium dichloride;
(318) dimethylsilylene bis[1,1'-{2-ethyl-4-(4-chlorophenyl)cyclopentacyclooctenyl}zirconium dichloride;
(319) dimethylsilylene bis[1,1'-{2-methyl-5-(4-trifluoromethylphenyl)cyclopentacyclooctenyl}zirconium dichloride.

(320) 9-silafluorene-9,9-diyl bis[1,1'-{2-methyl-4-(4-fluorophenyl)-4-hydroazulenyl}] zirconium dichloride;
(321) 9-silafluorene-9,9-diyl bis[1,1'-{2-methyl-4-(4-trifluoromethylphenyl)-4-hydroazulenyl}] zirconium dichloride;
(322) 1-silaindene-1,1-diyl bis[1,1'-{2-methyl-4-(4-fluorophenyl)-4-hydroazulenyl}] zirconium dichloride;
(323) 1-silaindene-1,1-diyl bis[1,1'-{2-methyl-4-(4-trifluoromethylphenyl)-4-hydroazulenyl}] zirconium dichloride;
(324) tetramethyl-1-silacyclopentadiene-1,1-diyl bis[1,1'-{2-methyl-4-(4-fluorophenyl)-4-hydroazulenyl}] zirconium dichloride;
(325) tetramethyl-1-silacyclopentadiene-1,1-diyl bis[1,1'-{2-methyl-4-(4-trifluoromethylphenyl)-4-hydroazulenyl}] zirconium dichloride;
(326) 1-silacyclo-3-pentene-1,1-diyl bis[1,1'-{2-methyl-4-(4-fluorophenyl)-4-hydroazulenyl}] zirconium dichloride;
(327) 1-silacyclo-3-pentene-1,1-diyl bis[1,1'-{2-methyl-4-(4-trifluoromethylphenyl)-4-hydroazulenyl}] zirconium dichloride;
(328) (4-fluorophenyl)methylsilylene bis[1,1'-{2-methyl-4-(4-fluorophenyl)-4-hydroazulenyl]zirconium dichloride;
(329) (4-chlorophenyl)methylsilylene bis[1,1'-{2-methyl-4-(4-fluorophenyl)-4-hydroazulenyl}] zirconium dichloride;
(330) (chloromethyl)methylsilylene bis[1,1'-{2-methyl-4-(4-trifluoromethylphenyl)-4-hydroazulenyl}] zirconium dichloride;
(331) (4-fluorophenyl)methylsilylene[1-{2-methyl-4-(4-fluorophenyl)-4-hydroazulenyl}]{1-(2-ethyl-4-phenylindenyl)}zirconium dichloride;
(332) dimethylsilylene bis{1,1'-(2-methyl-4-phenyl-7-isopropyl-4-hydroazulenyl)}zirconium dichloride;
(333) dimethylsilylene bis{1,1'-(2-ethyl-4-phenyl-7-isopropyl-4-hydroazulenyl)}zirconium dichloride;
(334) dimethylsilylene bis{1,1'-(2-propyl-4-phenyl-7-isopropyl-4-hydroazulenyl)}zirconium dichloride;
(335) dimethylsilylene bis{1,1'-(2-isopropyl-4-phenyl-7-isopropyl-4-hydroazulenyl)}zirconium dichloride;
(336) dimethylsilylene bis{1,1'-(2-phenyl-4-phenyl-7-isopropyl-4-hydroazulenyl)}zirconium dichloride;
(337) dimethylsilylene bis{1,1'-(2-trimethylsilylmethyl-4-phenyl-7-isopropyl-4-hydroazulenyl)}zirconium dichloride;
(338) dimethylsilylene bis[1,1'-{2-methyl-4-(1-naphthyl)-7-isopropyl-4-hydroazulenyl}] zirconium dichloride;
(339) dimethylsilylene bis[1,1'-{2-methyl-4-(2-naphthyl)-7-isopropyl-4-hydroazulenyl}] zirconium dichloride;
(340) dimethylsilylene bis[1,1'-{2-ethyl-4-(1-naphthyl)-7-isopropyl-4-hydroazulenyl}] zirconium dichloride;
(341) dimethylsilylene bis[1,1'-{2-ethyl-4-(2-naphthyl)-7-isopropyl-4-hydroazulenyl}] zirconium dichloride;
(342) dimethylsilylene bis{1,1'-(2-ethyl-4-phenyl-7-phenyl-4-hydroazulenyl)}zirconium dichloride;
(343) dimethylsilylene bis[1,1'-{2-ethyl-4-(1-naphthyl)-7-phenyl-4-hydroazulenyl}] zirconium dichloride;
(344) dimethylsilylene bis[1,1'-{2-ethyl-4-(2-naphthyl)-7-phenyl-4-hydroazulenyl}] zirconium dichloride;
(345) diphenylsilylene bis{1,1'-(2-methyl-4-phenyl-7-isopropyl-4-hydroazulenyl)}zirconium dichloride;
(346) diphenylsilylene bis{1,1'-(2-ethyl-4-phenyl-7-isopropyl-4-hydroazulenyl)}zirconium dichloride;
(347) diphenylsilylene bis{1,1'-(2-propyl-4-phenyl-7-isopropyl-4-hydroazulenyl)}zirconium dichloride;
(348) diphenylsilylene bis{1,1'-(2-isopropyl-4-phenyl-7-isopropyl-4-hydroazulenyl)}zirconium dichloride;
(349) diphenylsilylene bis{1,1'-(2-phenyl-4-phenyl-7-isopropyl-4-hydroazulenyl)}zirconium dichloride;
(350) diphenylsilylene bis{1,1'-(2-trimethylsilylmethyl-4-phenyl-7-isopropyl-4-hydroazulenyl)}zirconium dichloride;
(351) diphenylsilylene bis[1,1'-{2-ethyl-4-(1-naphthyl)-7-isopropyl-4-hydroazulenyl}] zirconium dichloride;
(352) diphenylsilylene bis[1,1'-{2-ethyl-4-(2-naphthyl)-7-isopropyl-4-hydroazulenyl}] zirconium dichloride;
(353) (methyl)(phenyl)silylene bis{1,1'-(2-methyl-4-phenyl-7-isopropyl-4-hydroazulenyl}] zirconium dichloride;
(354) (methyl)(phenyl)silylene bis{1,1'-(2-ethyl-4-phenyl-7-isopropyl-4-hydroazulenyl)}zirconium dichloride;
(355) (methyl)(phenyl)silylene bis[1,1'-{2-ethyl-4-(1-naphthyl)-7-isopropyl-4-hydroazulenyl}] zirconium dichloride;
(356) (methyl)(phenyl)silylene bis[1,1'-{2-ethyl-4-(2-naphthyl)-7-isopropyl-4-hydroazulenyl}] zirconium dichloride;
(357) dimethylsilylene bis{1,1'-(2-methyl-4-phenyl-7-isopropyl-4,5,6,7,8-pentahydroazulenyl)}zirconium dichloride;
(358) dimethylsilylene bis{1,1'-(2-ethyl-4-phenyl-7-isopropyl-4,5,6,7,8-pentahydroazulenyl)}zirconium dichloride;
(359) dimethylsilylene bis[1,1'-(2-ethyl-4-(1-naphthyl)-7-isopropyl-4,5,6,7,8-pentahydroazulenyl)] zirconium dichloride;
(360) dimethylsilylene bis[1,1'-(2-ethyl-4-(2-naphthyl)-7-isopropyl-4,5,6,7,8-pentahydroazulenyl)] zirconium dichloride;
(361) dimethylsilylene{1-(2-methyl-4-phenyl-7-isopropyl-4-hydroazulenyl)}{1-(2-methyl-4,5-benzoindenyl)}zirconium dichloride;
(362) dimethylsilylene{1-(2-ethyl-4-phenyl-7-isopropyl-4-hydroazulenyl)}{1-(2-methyl-4,5-benzoindenyl)}zirconium dichloride;
(363) dimethylsilylene[1-{2-ethyl-4-(1-naphthyl)-7-isopropyl-4-hydroazulenyl}]{1-(2-methyl-4,5-benzoindenyl)}zirconium dichloride;
(364) dimethylsilylene[1-{2-ethyl-4-(2-naphthyl)-7-isopropyl-4-hydroazulenyl}]{1-(2-methyl-4,5-benzoindenyl)}zirconium dichloride;
(365) dimethylsilylene{1-(2-methyl-4-phenyl-7-isopropyl-4-hydroazulenyl)}{1-(2-methyl-4-phenylindenyl)}zirconium dichloride;
(366) dimethylsilylene{1-(2-ethyl-4-phenyl-7-isopropyl-4-hydroazulenyl}{1-(2-methyl-4-phenylindenyl)}zirconium dichloride;
(367) dimethylsilylene[1-{2-ethyl-4-(1-naphthyl)-7-isopropyl-4-hydroazulenyl}]{1-(2-methyl-4-phenylindenyl)}zirconium dichloride;
(368) dimethylsilylene[1-{2-ethyl-4-(2-naphthyl)-7-isopropyl-4-hydroazulenyl}]{1-(2-methyl-4-phenylindenyl)}zirconium dichloride;
(369) methylene bis{1,1'-(2-methyl-4-phenyl-6-isopropyl-4-hydroazulenyl)}zirconium dichloride;
(370) methylene bis{1,1'-(2-methyl-4-phenyl-7-isopropyl-4-hydroazulenyl)}zirconium dichloride;
(371) methylene bis{1,1'-(2-methyl-6-isopropyl-4-hydroazulenyl)}zirconium dichloride;
(372) methylene bis{1,1'-(2-ethyl-4,7-diisopropyl-4,5,6,7,8-pentahydroazulenyl)}zirconium dichloride;
(373) methylene bis{1,1'-(4,6-dimethylcyclopentacyclooctenyl)}zirconium dichloride;
(374) methylene bis{1,1'-(4-methyl-6-isopropylcyclopentacyclooctenyl)}zirconium dichloride;

(375) methylene bis{1,1'-(2-methyl-5-phenylcyclopentacyclooctenyl)}zirconium dichloride;
(376) ethylene bis{1,1'-(2-methyl-4-phenyl-6-isopropyl-4-hydroazulenyl)}zirconium dichloride;
(377) ethylene bis{1,1'-(2-methyl-4-phenyl-7-isopropyl-4-hydroazulenyl)}zirconium dichloride;
(378) ethylene bis{1,1'-(2-methyl-6-isopropyl-4-hydroazulenyl)}zirconium dichloride;
(379) ethylene bis{1,1'-(2-ethyl-4,7-diisopropyl-4,5,6,7,8-pentahydroazulenyl)}zirconium dichloride;
(380) ethylene bis{1,1'-(4,6-dimethylcyclopentacyclooctenyl)}zirconium dichloride;
(381) ethylene bis{1,1'-(4-methyl-6-isopropylcyclopentacyclooctenyl)}zirconium dichloride;
(382) ethylene bis{1,1'-(2-methyl-5-phenylcyclopentacyclooctenyl)}zirconium dichloride;
(383) ethylene{(1-(2,4,7-trimethylindenyl)}{1-(2-methyl-4-phenyl-6-isopropyl-4-hydroazulenyl)}zirconium dichloride;
(384) ethylene{(1-(2-ethyl-4,5-benzoindenyl)}{1-(2-methyl-4-phenyl-7-isopropyl-4-hydroazulenyl)}zirconium dichloride;
(385) dimethylmethylene bis{1,1'-(2-methyl-4-phenyl-6-isopropyl-4-hydroazulenyl)}zirconium dichloride;
(386) dimethylmethylene bis{1,1'-(2-methyl-4-phenyl-7-isopropyl-4-hydroazulenyl)}zirconium dichloride;
(387) dimethylmethylene bis{1,1'-(2-methyl-6-isopropyl-4-hydroazulenyl)}zirconium dichloride;
(388) dimethylmethylene bis{1,1'-(2-ethyl-4,7-diisopropyl-4,5,6,7,8-pentahydroazulenyl)}zirconium dichloride;
(389) dimethylmethylene bis{1,1'-(4,6-dimethylcyclopentacyclooctenyl)}zirconium dichloride;
(390) dimethylmethylene bis{1,1'-(4-methyl-6-isopropylcyclopentacyclooctenyl)}zirconium dichloride;
(391) dimethylmethylene bis{1,1'-(2-methyl-5-phenylcyclopentacyclooctenyl)}zirconium dichloride;
(392) dimethylmethylene{(1-(2,4,7-trimethylindenyl)}(1-(2-methyl-4-phenyl-6-isopropyl-4-hydroazulenyl)}zirconium dichloride;
(393) dimethylmethylene{(1-(2-ethyl-4,5-benzoindenyl)}{1-(2-methyl-4-phenyl-7-isopropyl-4-hydroazulenyl)}zirconium dichloride;
(394) dimethylsilylene bis{1,1'-(2-methyl-4-phenyl-6-isopropyl-4-hydroazulenyl)}zirconium dichloride;
(395) dimethylsilylene bis{1,1'-(2-methyl-6-isopropyl-4-hydroazulenyl)}zirconium dichloride;
(396) dimethylsilylene bis{1,1'-(2-ethyl-4,7-diisopropyl-4-hydroazulenyl)}zirconium dichloride;
(397) dimethylsilylene bis{1,1'-(4,6-dimethylcyclopentacyclooctenyl)}zirconium dichloride;
(398) dimethylsilylene bis{1,1'-(4-methyl-6-isopropylcyclopentacyclooctenyl)}zirconium dichloride;
(399) dimethylsilylene bis{1,1'-(2-methyl-5-phenylcyclopentacyclooctenyl)}zirconium dichloride;
(400) dimethylsilylene{(1-(2,4,7-trimethylindenyl)}{1-(2-methyl-4-phenyl-6-isopropyl-4-hydroazulenyl)}zirconium dichloride;
(401) dimethylsilylene{(1-(2-ethyl-4,5-benzoindenyl)}{1-(2-methyl-4-phenyl-7-isopropyl-4-hydroazulenyl)}zirconium dichloride;
(402) (methyl)(phenyl)silylene bis{1,1'-(2-methyl-4-phenyl-6-isopropyl-4-hydroazulenyl)}zirconium dichloride;
(403) (methyl)(phenyl)silylene bis{1,1'-(2-methyl-4-phenyl-7-isopropyl-4-hydroazulenyl)}zirconium dichloride;
(404) diphenylsilylene bis{1,1'-(2-methyl-4-phenyl-6-isopropyl-4-hydroazulenyl)}zirconium dichloride;
(405) tetramethyldisilylene bis{1,1'-(2-methyl-4-phenyl-6-isopropyl-4-hydroazulenyl)}zirconium dichloride;
(406) tetramethyldisilylene bis{1,1'-(2-methyl-4-phenyl-7-isopropyl-4-hydroazulenyl)}zirconium dichloride;
(407) dimethylgermylene bis{1,1'-(2-methyl-4-phenyl-6-isopropyl-4-hydroazulenyl)}zirconium dichloride;
(408) dimethylgermylene bis{1,1'-(2-methyl-4-phenyl-7-isopropyl-4-hydroazulenyl)}zirconium dichloride;
(409) dimethylsilylene bis{1,1'-(2-benzyl-4-phenyl-4-hydroazulenyl)}zirconium dichloride;
(410) dimethylsilylene bis{1,1'-(2-heptyl-4-phenyl-4-hydroazulenyl)}zirconium dichloride;
(411) dimethylsilylene bis{1,1'-(2-octyl-4-phenyl-4-hydroazulenyl)}zirconium dichloride;
(412) dimethylsilylene bis[1,1'-{2-(1-phenylethyl)-4-phenyl-4-hydroazulenyl)}zirconium dichloride;
(413) dimethylsilylene bis[1,1'-{2-(2-phenylethyl)-4-phenyl-4-hydroazulenyl)}zirconium dichloride;
(414) dimethylsilylene bis[1,1'-{2-(1-naphthyl)-4-phenyl-4-hydroazulenyl)}zirconium dichloride;
(415) dimethylsilylene bis[1,1'-{2-(2-naphthyl)-4-phenyl-4-hydroazulenyl)}zirconium dichloride;
(416) dimethylsilylene bis{1,1'-(2-dimethylphenylsilyl-4-phenyl-4-hydroazulenyl)}zirconium dichloride;
(417) dimethylsilylene bis[1,1'-{2-benzyl-4-(1-naphthyl)-4-hydroazulenyl)}zirconium dichloride;
(418) dimethylsilylene bis[1,1'-{2-benzyl-4-(2-naphthyl)-4-hydroazulenyl)}zirconium dichloride;
(419) dimethylsilylene bis{1,1'-(2-benzyl-4-phenyl-7-isopropyl-4-hydroazulenyl)}zirconium dichloride;
(420) dimethylsilylene bis{1,1'-(2-heptyl-4-phenyl-7-isopropyl-4-hydroazulenyl)}zirconium dichloride;
(421) dimethylsilylene bis{1,1'-(2-octyl-4-phenyl-7-isopropyl-4-hydroazulenyl)}zirconium dichloride;
(422) dimethylsilylene bis[1,1'-{2-(1-phenylethyl)-4-phenyl-7-isopropyl-4-hydroazulenyl)}zirconium dichloride;
(423) dimethylsilylene bis[1,1'-{2-(2-phenylethyl)-4-phenyl-7-isopropyl-4-hydroazulenyl)}zirconium dichloride;
(424) dimethylsilylene bis[1,1'-{2-(1-naphthyl)-4-phenyl-7-isopropyl-4-hydroazulenyl)}zirconium dichloride;:
(425) dimethylsilylene bis[1,1'-{2-(2-naphthyl)-4-phenyl-7-isopropyl-4-hydroazulenyl)}zirconium dichloride;
(426) dimethylsilylene bis{1,1'-(2-dimethylphenylsilyl-4-phenyl-7-isopropyl-4-hydroazulenyl)}zirconium dichloride;
(427) dimethylsilylene bis[1,1'-{2-benzyl-4-(1-naphthyl)-7-isopropyl-4-hydroazulenyl)}zirconium dichloride;
(428) dimethylsilylene bis[1,1'-{2-benzyl-4-(2-naphthyl).-7-isopropyl-4-hydroazulenyl)}zirconium dichloride;
(429) diphenylsilylene bis{1,1'-(2-benzyl-4-phenyl-4-hydroazulenyl)}zirconium dichloride;
(430) diphenylsilylene bis[1,1'-{2-benzyl-4-(1-naphthyl)-4-hydroazulenyl)}zirconium dichloride;
(431) diphenylsilylene bis[1,1'-{2-benzyl-4-(2-naphthyl)-4-hydroazulenyl)}zirconium dichloride;
(432) diphenylsilylene bis{1,1'-(2-benzyl-4-phenyl-7-isopropyl-4-hydroazulenyl)}zirconium dichloride;
(433) diphenylsilylene bis[1,1'-{2-(1-phenylethyl)-4-phenyl-4-hydroazulenyl)}zirconium dichloride;
(434) diphenylsilylene bis[1,1'-{2-(1-phenylethyl)-4-phenyl-7-isopropyl-4-hydroazulenyl)}zirconium dichloride;
(435) (methyl)(phenyl)silylene bis{1,1'-(2-benzyl-4-phenyl-4-hydroazulenyl)}zirconium dichloride;
(436) (methyl)(phenyl)silylene bis[1,1'-{2-benzyl-4-(1-naphthyl)-4-hydroazulenyl)}zirconium dichloride;

(437) (methyl)(phenyl)silylene bis[1,1'-{2-benzyl-4-(2-naphthyl)-4-hydroazulenyl)}zirconium dichloride;
(438) (methyl)(phenyl)silylene bis{1,1'-(2-benzyl-4-phenyl-7-isopropyl-4-hydroazulenyl)}zirconium dichloride;
(439) (methyl)(phenyl)silylene bis[1,1'-{2-(1-phenylethyl)-4-phenyl-4-hydroazulenyl)}zirconium dichloride;
(440) (methyl)(phenyl)silylene bis[1,1'-{2-(1-phenylethyl)-4-phenyl-7-isopropyl-4-hydroazulenyl)}zirconium dichloride;
(441) dimethylsilylene{1-(2-benzyl-4-phenyl-4-hydroazulenyl)}{1-(2-methyl-4,5-benzoindenyl)}zirconium dichloride;
(442) dimethylsilylene[1-{2-benzyl-4-(1-naphthyl)-4-hydroazulenyl}]{1-(2-methyl-4,5-benzoindenyl)}zirconium dichloride;
(443) dimethylsilylene[1-{2-benzyl-4-(2-naphthyl)-4-hydroazulenyl}]{1-(2-methyl-4,5-benzoindenyl)}zirconium dichloride;
(444) dimethylsilylene[1-{2-benzyl-4-phenyl-7-isopropyl-4-hydroazulenyl}]{1-(2-methyl-4,5-benzoindenyl)}zirconium dichloride;
(445) dimethylsilylene[1-{2-(1-phenylethyl)-4-phenyl-4-hydroazulenyl}]{1-(2-methyl-4,5-benzoindenyl)}zirconium dichloride;
(446) dimethylsilylene[1-{2-(1-phenylethyl)-4-phenyl-7-isopropyl-4-hydroazulenyl}]{1-(2-methyl-4,5-benzoindenyl)}zirconium dichloride;
(447) dimethylsilylene{1-(2-benzyl-4-phenyl-4-hydroazulenyl}▽{1-(2-methyl-4-phenylindenyl)]zirconium dichloride;
(448) dimethylsilylene[1-{2-benzyl-4-(1-naphthyl)-4-hydroazulenyl}]{1-(2-methyl-4-phenylindenyl)}zirconium dichloride;
(449) dimethylsilylene[1-{2-benzyl-4-(2-naphthyl)-4-hydroazulenyl}]{1-(2-methyl-4-phenylindenyl)}zirconium dichloride;
(450) dimethylsilylene[1-{2-benzyl-4-phenyl-7-isopropyl-4-hydroazulenyl}]{1-(2-methyl-4-phenylindenyl)}zirconium dichloride;
(451) dimethylsilylene[1-{2-(1-phenylethyl)-4-phenyl-4-hydroazulenyl}]{1-(2-methyl-4-phenylindenyl)}zirconium dichloride;
(452) dimethylsilylene[1-{2-(1-phenylethyl)-4-phenyl-7-isopropyl-4-hydroazulenyl}]{1-(2-methyl-4-phenylindenyl)}zirconium dichloride;
(453) 9-silafluorene-9,9-diyl bis{1,1'-(2-methyl-4-phenyl-4-hydroazulenyl)}zirconium dichloride;
(454) 9-silafluorene-9,9-diyl bis{1,1'-(2-ethyl-4-phenyl-4-hydroazulenyl)}zirconium dichloride;
(455) 9-silafluorene-9,9-diyl bis{1,1'-(2,8-dimethyl-4-phenyl-4-hydroazulenyl)}zirconium dichloride;
(456) 9-silafluorene-9,9-diyl bis[1,1'-{2-methyl-4-(1-naphthyl)-4-hydroazulenyl}] zirconium dichloride;
(457) 9-silafluorene-9,9-diyl{1-(2-methyl-4-phenyl-4-hydroazulenyl)}{1-(2-methyl-4-phenyl-4,5,6,7,8-pentahydroazulenyl)}zirconium dichloride;
(458) 9-silafluorene-9,9-diyl{1-(2-methyl-4-phenyl-4-hydroazulenyl)}{1-(2-methyl-4-phenylindenyl)}zirconium dichloride;
(459) 1-silaindene-1,1-diyl bis{1,1'-(2-methyl-4-phenyl-4-hydroazulenyl)}zirconium dichloride;
(460) 1-silaindene-1,1-diyl bis{1,1'-(2-ethyl-4-phenyl-4-hydroazulenyl)}zirconium dichloride;
(461) 1-silaindene-1,1-diyl bis{1,1'-(2,8-dimethyl-4-phenyl-4-hydroazulenyl)}zirconium dichloride;
(462) 1-silaindene-1,1-diyl bis[1,1'-{2-methyl-4-(1-naphthyl)-4-hydroazulenyl}] zirconium dichloride;
(463) 1-silaindene-1,1-diyl{1-(2-methyl-4-phenyl-4-hydroazulenyl)}{1-(2-methyl-4-phenyl-4,5,6,7,8-pentahydroazulenyl)}zirconium dichloride;
(464) 1-silaindene-1,1-diyl{1-(2-methyl-4-phenyl-4-hydroazulenyl)}{1-(2-methyl-4-phenylindenyl)}zirconium dichloride;
(465) tetramethyl-1-silacyclopentadiene-1,1-diyl bis{1,1'-(2-methyl-4-phenyl-4-hydroazulenyl)}zirconium dichloride;
(466) tetramethyl-1-silacyclopentadiene-1,1-diyl bis{1,1'-(2-ethyl-4-phenyl-4-hydroazulenyl)}zirconium dichloride;
(467) tetramethyl-1-silacyclopentadiene-1,1-diyl bis{1,1'-(2,8-dimethyl-4-phenyl-4-hydroazulenyl)}zirconium dichloride;
(468) tetramethyl-1-silacyclopentadiene-1,1-diyl bis[1,1'-{2-methyl-4-(1-naphthyl)-4-hydroazulenyl}] zirconium dichloride;
(469) tetramethyl-1-silacyclopentadiene-1,1-diyl{1-(2-methyl-4-phenyl-4-hydroazulenyl)}{1-(2-methyl-4-phenyl-4,5,6,7,8-pentahydroazulenyl)}zirconium dichloride;
(470) tetramethyl-1-silacyclopentadiene-1,1-diyl{1-(2-methyl-4-phenyl-4-hydroazulenyl)}{1-(2-methyl-4-phenylindenyl)}zirconium dichloride;
(471) 1-silacyclo-3-pentene-1,1-diyl bis{1,1'-(2-methyl-4-phenyl-4-hydroazulenyl)}zirconium dichloride;
(472) 1-silacyclo-3-pentene-1,1-diyl bis{1,1'-(2-ethyl-4-phenyl-4-hydroazulenyl)}zirconium dichloride;
(473) 1-silacyclo-3-pentene-1,1-diyl bis{1,1'-(2,8-dimethyl-4-phenyl-4-hydroazulenyl)}zirconium dichloride;
(474) 1-silacyclo-3-pentene-1,1-diyl bis[1,1'-{2-methyl-4-(1-naphthyl)-4-hydroazulenyl}] zirconium dichloride;
(475) 1-silacyclo-3-pentene-1,1-diyl{1-(2-methyl-4-phenyl-4-hydroazulenyl)}{1-(2-methyl-4-phenyl-4,5,6,7,8-pentahydroazulenyl)}zirconium dichloride;
(476) 1-silacyclo-3-pentene-1,1-diyl{1-(2-methyl-4-phenyl-4-hydroazulenyl)}{1-(2-methyl-4-phenylindenyl)}zirconium dichloride.

In addition, as the transition metal compounds according to the present invention, there can also be exemplified those compound in which one or both of two chlorine atoms constituting the groups X and Y in the general formulae (I) to (VI) are substituted by a hydrogen atom, a fluorine atom, bromine atom, an iodine atom, a methyl group, a phenyl group, a fluorophenyl group, a benzyl group, an methoxy group, a dimethylamino group, a diethylamino group, or the like. Further, there can also be exemplified those compounds in which zirconium as the central metal M of each of the above-mentioned compounds, is substituted by titanium, hafnium, tantalum, niobium, vanadium, tungsten, molybdenum or the like. Among them, compounds containing Group 4 transition metals such as zirconium, titanium or hafnium are preferred, and compounds containing zirconium or hafnium are especially preferred.

Next, the catalyst (1) for polymerization of α-olefin according to the first aspect of the present invention is explained below. The catalyst (1) comprises, as essential components, the afore-mentioned transition metal compound (component A) and the specific ion exchangeable layer compound or the inorganic silicate (component B), and as an optional component, the organoaluminum compound (component C).

First, as the component B, the inorganic silicate or the ion exchangeable layer compound except for silicate (hereinafter referred to merely as "ion exchangeable layer compound") is described in detail below.

As the afore-mentioned ion exchangeable layer compounds as the component (B), there can be exemplified ionic crystalline compounds of a hexagonal closest packing type, an antimony type, a $CdCl_2$ type or a $CdI_2$ type, which have a layer crystal structure. Specific examples of the ion exchangeable layer compounds may include crystalline acid salts of polyvalent metals such as $\alpha$-$Zr(HAsO_4)_2 \cdot H_2O$, $\alpha$-$Zr(HPO_4)_2$, $\alpha$-$Zr(KPO_4)_2 \cdot 3H_2O$, $\alpha$-$Ti(HPO_4)_2$, $\alpha$-$Ti(HAsO_4)_2 \cdot H_2O$, $\alpha$-$Sn(HPO_4)_2 H_2O$, $\gamma$-$Zr(HPO_4)_2$, $\gamma$-$Ti(HPO_4)_2$ or $\gamma$-$Ti(NH_4PO_4)_2 \cdot H_2O$.

The afore-mentioned ion exchangeable layer compounds may be treated with salts and/or acids, if required. The ion exchangeable layer compounds except for silicates which are treated with neither salts nor acids, have such a crystal structure that layers formed by ionic bond or the like are overlapped in parallel to one another with a weak bonding force therebetween and, therefore, the layers contain ions exchangeable with each other.

As the afore-mentioned inorganic silicates as the component (B), there can be exemplified clays, clay minerals, zeolite, diatomaceous earth or the like. These inorganic silicates may be either synthesized products or naturally outputted minerals. Specific examples of clays or clay minerals may include allophane group clays or clay minerals such as allophane; kaolin group clays or clay minerals such as dickite, nacrite, kaolinite or anauxite, halloysite group clays or clay minerals such as meta-halloysite or halloysite; serpentine group clays or clay minerals such as chrysotile, lizardite or antigorite; smectite group clays or clay minerals such as montmorillonite, sauconite, beidellite, nontronite, saponite or hectorite; vermiculite minerals such as vermiculite; mica minerals such as illite, sericite or glauconite; attapulgite; sepiolite; palygorskite; bentonite; gnarl clay; gairome clay hisingerite; pyrophyllite; chlorite groups; or the like. These inorganic silicates may be in the form of mixed layers thereof. In addition, as the synthetic inorganic silicates, there can be exemplified synthetic mica, synthetic hectorite, synthetic saponite, synthetic taeniolite or the like.

Among the afore-mentioned inorganic silicates, kaolin group clays or clay minerals, halloysite group clays or clay minerals, serpentine group clays or clay minerals, smectite group clays or clay minerals, vermiculite minerals, mica minerals, synthetic mica, synthetic hectorite, synthetic saponite or synthetic taeniolite are preferred, and especially preferred inorganic silicates are smectite, vermiculite minerals, synthetic mica, synthetic hectorite, synthetic saponite and synthetic taeniolite. These inorganic silicates may be used in untreated state as they are, or may be used after subjected to treatments such as crushing by a ball mill, screening or the like. Further, these inorganic silicates may be used singly or in the form of a mixture of any two or more thereof.

The afore-mentioned ion exchangeable layer compounds except for silicates and the inorganic silicates as the component (B) can be treated with salts and/or acids to control an acid strength of these solid compounds. Further, when these compounds are treated with salts, ion composites, molecule composites or organic derivatives are formed, so that it becomes possible to appropriately change the surface area and interlayer distance thereof. Specifically, exchangeable ions existing between the respective layers can be replaced with other bulkier ions by the aid of ion exchanging properties of these compounds, thereby obtaining a layer substance having an increased interlayer distance.

If these compounds are not pre-treated as described above, it is preferred that metal cations contained therein are ion-exchanged with cations dissociated from the below-mentioned salts and/or acids.

The salts used for the afore-mentioned ion exchange, may be compounds comprising a cation which contains at least one atom selected from the group consisting of Group 1–14 atoms, preferably compounds comprising a cation which contains at least one atom selected from the group consisting of Group 1–14 atoms and at least one anion derived from an atom or atomic group selected from the group consisting of halogen atoms, inorganic acids and organic acids, more preferably compounds comprising a cation which contains at least one atom selected from the group consisting of Group 2–14 atoms and at least one anion selected from the group consisting of Cl, Br, I, F. $PO_4$, $SO_4$, $NO_3$, $CO_3$, $C_2O_4$, $ClO_4$, $OCCH_3$, $CH_3COCHCOCH_3$, $OCl_2$, $O(NO_3)_2$, $O(ClO_4)_2$, $O(SO_4)$, $OH$, $O_2Cl_2$, $OCl_3$, $OOCH$ and $OCCCH_2CH_3$. These salts may be used singly or in the form of a mixture of any two or more thereof in combination.

The acids used for the afore-mentioned ion exchange, may be selected from hydrochloric acid, sulfuric acid, nitric acid, acetic acid and oxalic acid. These acids may be used singly or in the form of a mixture of any two or more thereof. The salt treatment can be used in combination with the acid treatment. As methods in which the salt treatment and the acid treatment are used in combination, there can be exemplified a method of conducting the acid treatment after the salt treatment, a method of conducting the salt treatment after the acid treatment, a method of conducting the salt and acid treatments simultaneously, and a method of conducting the salt and acid treatments simultaneously after the salt treatment. Incidentally, the acid treatment has such effects, afore-mentioned ion exchange that impurities can be removed from the surface of the component (B), and that a part of cations contained in the crystal structure such as Al, Fe, Mg or Li can be eluted therefrom.

The treating conditions used for the salt or acid treatment are not particularly restricted. However, it is suitable that the concentration of the salt or acid is usually in the range of 0.1 to 30% by weight; the treating temperature is usually from room temperature to a boiling point of solvent used; and the treating time is usually from 5 minutes to 24 hours, such that at least a part of the compound to be treated is solved out. Further, the salts and the acids are usually used in the form of an aqueous solution.

In the afore-mentioned salt and/or acid treatments, the component (B) may be pulverized or granulated before, during or after the salt and/or acid treatments to control the shape thereof. In addition, other chemical treatments such as alkali treatment or treatments by organic substances may be used in combination. The thus-prepared component (B) has preferably a pore volume of usually not less than 0.1 cc/g, more preferably 0.3 to 5 cc/g, when measured with respect to pores having a radius of not less than 20 Å by a mercury-penetrating method. Such a component (B) generally contains an absorbed water or an interlayer water. Here, the absorbed water means water absorbed on a surface or a crystal fracture face of the ion exchangeable layer compound or the inorganic silicate, and the interlayer water means water existing between the layers.

In accordance with the present invention, it is preferred that the component (B) is used after removal of the afore-mentioned absorbed water or interlayer water. The methods for removing the water, are nor particularly restricted, but there can be used dehydrating methods such as heating, heating in the presence of a flowing gas, heating under a reduced pressure, azeotropy with an organic solvent, or the like. The heating may be conducted at such a temperature that no absorbed water and interlayer water exists in the component (B). The heating temperature is usually not less than 100° C., preferably not less than 150° C. However, the use of such a high temperature which causes destruction of the crystal structure should be avoided. The heating time is usually not less than 0.5 hour, preferably not less than one hour. The weight loss of the thus-treated component (B) is preferably not more than 3% by weight, when the suction is conducted at a temperature of 200° C. under a pressure of 1 mmHg for 2 hours. In accordance with the present invention, in the case where the component (B) whose weight loss is adjusted to not more than 3% by weight based on the weight of the component (B) is used, it is preferred that the weight loss of the component (B) is also maintained when the component (B) is brought into contact with the essential component (A) and the below-mentioned optional component (C).

Next, the organoaluminum compound (component (C)) is explained in detail below. As the component (C), there can be preferably used organoaluminum compounds represented by the general formula (VII):

$$AlR_aP_{3-a} \tag{VII}$$

wherein R is a hydrocarbon group raving 1 to 20 carbon atoms; P is a hydrogen atom, a halogen atom, an alkoxy group or a siloxy group; and "a" is a number satisfying $0 < a \leq 3$.

Specific examples of the organoaluminum compounds represented by the afore-mentioned general formula (VII) may include trialkylaluminums such as trimethylaluminum, triethylaluminum, tripropylaluminum or triisobutylaluminum, halogen-containing or alkoxy-containing alkylaluminums such as diethylaluminum monochloride or diethylaluminum monomethoxide, or the like. Among them, trialkylaluminums can be preferably used. Further, in the case of the catalyst (1) for polymerization of α-olefin according to the first aspect of the present invention, aluminoxanes such as methylaluminoxane or the like can also be used as the component (C).

The catalyst (1) for polymerization of α-olefin can be prepared by bringing the essential components (A) and (B) and the optional component (C) in contact with each other. The contacting method is not particularly restricted, but the following methods (i) to (v) can be exemplified. Incidentally, the contact between these components may be performed not only upon the production of the catalyst but also upon pre-polymerization or polymerization of the olefins.

(i) Method of bringing the components (A) and (B) into contact with each other;
(ii) Method of bringing the components (A) and (B) into contact with each other and then adding the component (C) to the mixture;
(iii) Method of bringing the components (A) and (C) into contact with each other and then adding the component (B) to the mixture;
(iv) Method of bringing the components (B) and (C) into contact with each other and then adding the component (A) to the mixture; and
(v) Method of bringing the components (A), (B) and (C) into contact with each other at the same time.

When or after the respective components are brought into contact with each other, polymers such as polyethylene or polypropylene or solid components of inorganic oxides such as silica or alumina may co-exist therein or may be contacted therewith.

In addition, the contact between the respective components can be conducted in an atmosphere of an inert gas such as nitrogen or in the presence of an inert hydrocarbon solvent such as pentane, hexane, heptane, toluene or xylene. Further, the contact is preferably conducted at a temperature of from −20° C. to a boiling point of the solvent used, more preferably from room temperature to the boiling point of the solvent used.

The amount of the component (A) used is usually in the range of $10^{-4}$ to 10 mmol, preferably $10^{-3}$ to 5 mmol based on one gram of the component (B). The amount of the component (C) used is usually in the range of 0.01 to $10^4$ mmol, preferably 0.1 to 100 mmol based on one gram of the component (B). In addition, the atomic ratio of the transition metal contained in the component (A) to aluminum contained in the component (C) is usually in the range of 1/0.01 to $1/10^6$, preferably 1/0.1 to $1/10^5$. The thus-prepared catalyst may be used as it is without washing, or may be used after washing. Further, the catalyst can be used in combination with a further component (C') which is composed of similar compounds to the component (C), if required. That is, when the components (A) and/or (B) and the component (C) are used to prepare the catalyst, the further component (C') may be added to a reaction system separately from that the component (C) used for the preparation of the catalyst. In this case, the amount of the further added component (C') can be selected such that the atomic ratio of the transition metal contained in the component (A) to aluminum contained in the further added component (C') is 1/0 to $1/10^4$.

Next, the catalyst (2) for polymerization of α-olefin according to the second aspect of the present invention, is explained in detail below. The catalyst (2) may contain, as essential components, (i) a novel transition metal compound represented by the afore-mentioned general formula (II), (III), (IV), (V) or (VI) (component (A)) and (ii) an aluminumoxy compound, an ionic compound capable of reacting with the component (A) to convert the component (A) into a cation or a Lewis acid (component (D)), and as an optional component, (iii) a fine particle carrier (component (E)). Incidentally, some of Lewis acids can act as the ionic compound capable of reacting with the component (A) to convert the component (A) into a cation. Accordingly, if the afore-mentioned compound having the properties of both the Lewis acid and the ionic compound is used, the compound is regarded as belonging to any one thereof.

As the afore-mentioned aluminumoxy compounds, there can be exemplified those compounds represented by the following general formulae (VIII), (IX) and (X):

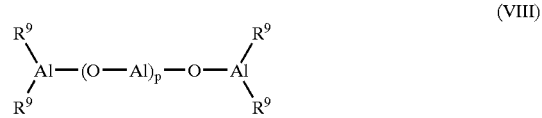

(VIII)

(IX)

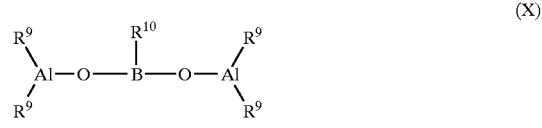

(X)

In the afore-mentioned general formulae (VIII), (IX) and (X), $R^9$ is a hydrogen atom or a hydrocarbon group having preferably 1 to 10 carbon atoms, more preferably 1 to 6 carbon atoms, providing that when a plurality of the $R^9$ are present in the same molecule, these $R^9$ may be the same or different; and p is an integer of 0 to 40, preferably 2 to 30.

The compounds represented by the general formulae (VIII) and (IX) are also called "alumoxane", and can be obtained by reacting at least one trialkylaluminum with water. Specific examples of the compounds represented by the general formulae (VIII) and (IX) may include (i) compounds obtained by reacting one kind of trialkylaluminum with water, such as methylalumoxane, ethylalumoxane, propylalumoxane, butylalumoxane or isobutylalumoxane, (ii) compounds obtained by reacting two kinds of trialkylaluminum with water, such as methylethylalumoxane, methylbutylalumoxane or methylisobutylalumoxane, or the like. Among them, methylalumoxane and methylisobutylalumoxane are preferred.

The afore-mentioned alumoxanes can be used in combination within each group or between a plurality of groups. The alumoxanes can be prepared under various known conditions. Specifically, the following methods can be used for the production of these alumoxanes:

(a) Method of directly reacting trialkylaluminum with water in the presence of an appropriate organic solvent such as toluene, benzene or ether;
(b) Method of reacting trialkylaluminum with a salt containing crystallization water, e.g., a hydrate of copper sulfate or aluminum sulfate;
(c) Method of reacting trialkylaluminum with a water content impregnated in silica gel or the like;
(d) Method of mixing trimethylaluminum and triisobutylaluminum together, and then directly reacting the mixed trialkylaluminums with water in the presence of an appropriate organic solvent such as toluene, benzene or ether;
(e) Method of mixing trimethylaluminum and triisobutylaluminum together, and then reacting the mixed trialkylaluminums with a salt containing crystallization water, e.g., a hydrate of copper sulfate or aluminum sulfate while heating;
(f) Method of impregnating water into silica gel or the like, and treating the water-impregnated silica gel, etc., with triisobutylaluminum and then with trimethylaluminum;
(g) Method of preparing methylalumoxane and isobutylalumoxane by a known method, and then mixing these two components together at a predetermined ratio to be reacted with each other while heating; and
(h) Method of adding a salt containing crystallization water such as copper sulfate pentahydrate and trimethylaluminum into an aromatic hydrocarbon solvent such as benzene or toluene and reacting these components with each other at a temperature of about −40° C. to about 40° C.

The molar ratio of water used to the trimethylaluminum is usually in the range of 0.5 to 1.5. Methylalumoxane prepared by the afore-mentioned methods is a linear or cyclic organoaluminum polymer.

The compounds represented by the general formula (X) can be obtained by reacting at least one trialkylaluminum with alkyl boric acid represented by the following general formula (XI) at a molar ratio of 10:1 to 1:1.

$$R^{10}-B-(OH)_2 \tag{XI}$$

wherein $R^{10}$ is a hydrocarbon group or a halogenated hydrocarbon group both having 1 to 10 carbon atoms, preferably 1 to 6 carbon atoms.

Specific examples of the compounds represented by the general formula (XI) may include the following reaction products:

(a) Reaction products obtained by reacting trimethylaluminum with methylboric acid at a molar ratio of 2:1;
(b) Reaction products obtained by reacting triisobutylaluminum with methylboric acid at a molar ratio of 2:1;
(c) Reaction products obtained by reacting trimethylaluminum, triisobutylaluminum and methylboric acid with each other at a molar ratio of 1:1:1;
(d) Reaction products obtained by reacting trimethylaluminum with ethylboric acid at a molar ratio of 2:1; and
(e) Reaction products obtained by reacting triethylaluminum with butylboric acid at a -molar ratio of 2:1.

In addition, as the ionic compounds capable of reacting with the component (A) to convert the component (A) into a cation, there can be exemplified those compounds represented by the general formula (XII):

$$[K]e^+[Z]e^- \tag{XII}$$

In the general formula (XII), K represents a cationic component. Examples of the cations may include carbonium cation, tropylium cation, ammonium cation, oxonium cation, sulfonium cation, phosphonium cation or the like. Further, metal cations which tend to be reduced per se, cations of organic metals or the like can also be used.

Specific examples of the afore-mentioned cations may include triphenyl carbonium, diphenyl carbonium, cyclohepta trienium, indenium, triethylammonium, tripropylammonium, tributylammonium, N,N-dimethylammonium, dipropylammonium, dicyclohexylammonium, triphenylphosphonium, trimethylphosphonium, tris(dimethylphenyl)phosphonium, tris(methylphenyl)phosphonium, triphenylsulfonium, triphenyloxonium, triethyloxonium, pyrylium, silver ion, gold ion, platinum ion, copper ion, palladium ion, mercury ion, ferrocenium ion or the like.

In the general formula (XII), Z represents an ionic anion component (generally a non-coordinated component), which constitutes a counter anion against the cation produced by the conversion of the component (A). As the anion Z, there can be exemplified anions of organic boron compounds, anions of organoaluminum compounds, anions of organogallium compounds, anions of organophosphorus compounds, anions of organoarsenic compounds, anions of organoanthimony compounds or the like. Specific examples of these organic compounds are as follows.

(a) tetraphenylboron, tetrakis(3,4,5-trifluorophenyl)boron, tetrakis{3,5-bis(trifluoromethyl)phenyl}boron, tetrakis{3,5-di(t-butyl)phenyl}boron, tetrakis(pentafluorophenyl)boron, or the like;
(b) tetraphenylaluminum, tetrakis(3,4,5-trifluorophenyl) aluminum, tetrakis{3,5-bis(trifluoromethyl)phenyl) aluminum, tetrakis(3,5-di(t-butyl)phenyl)aluminum, tetrakis(pentafluorophenyl)aluminum, or the like;
(c) tetraphenylgallium, tetrakis(3,4,5-trifluorophenyl) gallium, tetrakis{3,5-bis(trifluoromethyl)phenyl)gallium, tetrakis(3,5-di(t-butyl)phenyl)gallium, tetrakis(pentafluoro)phenylgallium, or the like;
(d) tetraphenyl phosphorus, tetrakis(pentafluorophenyl) phosphorus, or the like;
(e) tetraphenyl arsenic, tetrakis(pentafluorophenyl) arsenic, or the like;
(f) tetraphenyl antimony, tetrakis(pentafluorophenyl) antimony, or the like; and
(g) decaborate, undecaborate, carbadodecaborate, decachlorodecaborate, or the like.

Further, as the Lewis acids, especially those capable of converting the component (A) into a cation, there can be exemplified various organoboron compounds, halogenated metal compounds, solid acids or the like. Specific examples of these Lewis acids are as follows:

(a) organoboron compounds such as triphenylboron, tris(3, 5-difluorophenyl)boron or tris(pentafluorophenyl)boron;
(b) halogenated metal compounds such as aluminum chloride, aluminum bromide, aluminum iodide, magnesium chloride, magnesium bromide, magnesium iodide, magnesium chloride bromide, magnesium chloride iodide, magnesium bromide iodide, magnesium chloride hydride, magnesium chloride hydroxide, magnesium bromide hydroxide, magnesium chloride alkoxide or magnesium bromide alkoxide; and
(c) solid acids such as alumina or silica-alumina.

In the catalyst (2) for polymerization of α-olefin, the fine particle carrier as the optional component (E) may be composed of an inorganic or organic compound, and in the form of granules or particles having a particle diameter of usually 5 μm to 5 mm, preferably 10 μm to 2 mm.

As the afore-mentioned inorganic carrier, there can be exemplified oxides such as $SiO_2$, $Al_2O_3$, MgO, ZrO, $TiO_2$, $B_2O_3$ or ZnO; composite oxides such as $SiO_2$—MgO, $SiO_2$—$Al_2O_3$, $SiO_2$—$TiO_2$, $SiO_2$—$Cr_2O_3$ or $SiO_2$—$Al_2O_3$—MgO; or the like.

As the afore-mentioned organic carrier, there can be exemplified fine particles of porous polymers, for example, polymers or copolymers of α-olefins having 2 to 14 carbon atoms such as ethylene, propylene, 1-butene or 4-methyl-1-pentene; polymers or copolymers of aromatic unsaturated hydrocarbons such as styrene or divinylbenzene; or the like. These organic carriers have a specific surface area of usually 20 to 1,000 $m^2/g$, preferably 50 to 700 $m^2/g$, and a pore volume of usually not less than 0.1 $cm^3/g$, preferably not less than 0.3 $cm^3/g$, more preferably not less than 0.8 $cm^3/g$.

The catalyst (2) for polymerization of α-olefin may contain, as other optional components than the fine particle carrier, for example, protic compounds such as $H_2O$, methanol, ethanol or butanol; electron donative compounds such as ethers, esters or amines; alkoxy-containing compounds such as phenylborate, dimethylmethoxyaluminum, phenylphosphite, tetraethoxysilane or diphenyldimethoxysilane; or the like.

As still further optional components other than the afore-mentioned compounds, there can be exemplified tri lower-alkylaluminums such as trimethylaluminum, triethylaluminum or triisobutylaluminum; halogen-containing alkylaluminums such as diethylaluminum chloride, diisobutylaluminum chloride or methylaluminum sesqui-chloride; alkylaluminum hydrides such as diethylaluminum hydride; alkoxy-containing alkylaluminums such as diethylaluminum ethoxide or dimethylaluminum butoxide; aryloxy-containing alkylaluminums such as diethylaluminum phenoxide; or the like.

In the catalyst (2) for polymerization of α-olefin, the aluminum-oxy compound, the ionic compound capable of reacting with the component (A) to convert the component (A) into a cation, and the Lewis acid as the component (D) are used singly or in the form of a mixture of any two or more thereof in combination. Incidentally, it is preferred that as the still further optional components, one or more kinds of the afore-mentioned lower-alkylaluminum, halogen-containing alkylaluminum, alkylaluminum hydride, alkoxy-containing alkylaluminum or aryloxy-containing alkylaluminum are contained in the catalyst (2) for polymerization of α-olefin, together with the aluminum-oxy compound, the ionic compound or the Lewis acid.

The catalyst (2) for polymerization of α-olefin may be prepared by bringing the components (A) and (D) into contact with each other inside or outside of a polymerization vessel and in the presence or absence of a monomer to be polymerized. In this case, the components (A) and (D), and if required, the component (E), etc., may be introduced separately into the polymerization vessel. Alternatively, the components (A) and (D) may be introduced into the polymerization vessel after both the components have been preliminarily brought into contact with each other. Further, after the components (A) and (D) are mixed together and impregnated into the component (E), the mixture may be introduced into the polymerization vessel.

The contact between the respective components can be conducted in an atmosphere containing an inert gas such as nitrogen or in the presence of an inert hydrocarbon solvent such as pentane, hexane, heptane, toluene or xylene. In addition, the contact can be conducted at a temperature of from −20° C. to a boiling point of the solvent used, preferably from room temperature to the boiling point of the solvent used. The thus-produced catalyst may be used as it is without washing, or may be used after washing. Further, the obtained catalyst may be used in combination with additional components, if required.

Also, when the components (A), (D) and (E) are preliminarily brought into contact with each other, the contact can be performed in the presence of the monomer to be polymerized, i.e., α-olefin to partially polymerize the α-olefin (so-called pre-polymerization). More specifically, before the polymerization, the α-olefin such as ethylene, propylene, 1-butene, 1-hexene, 1-octene, 4-methyl-1-pentene, 3-methyl-1-butene, vinylcycloalkanes or styrene is pre-polymerized and washed, if required. The thus-produced pre-polymerization product can be used as a catalyst. In this case, it is preferred that the pre-polymerization is conducted in the presence of an inert solvent under such a moderate reaction condition that the polymer is produced in an amount of usually 0.01 to 1,000 g, preferably 0.1 to 100 g based on one gram of the solid catalyst.

The amounts of the components (A) and (D) used are optional. For example, in the case of solution polymerization, the amount of the component (A) used is usually in the range of $10^{-7}$ to $10^2$ mmol/liter (calculated as the transition metal), preferably $10^{-4}$ to 1 mmol/liter. In the case where the aluminum-oxy compound is used as the component (D), the molar ratio of Al to the transition metal is usually in the range of 10 to $10^5$, preferably 100 to $2\times10^4$, more preferably 100 to $10^4$. On the other hand, in the case where the ionic compound or the Lewis acid is used as the component (D), the molar ratio of the ionic compound or the Lewis acid to the transition metal is usually in the range of 0.1 to 1,000, preferably 0.5 to 100, more preferably 1 to 50.

Next, the method for producing an α-olefin polymer according to the present invention, is explained in detail below. In accordance with the present invention, the afore-mentioned catalyst and α-olefin are brought into contact with each other to polymerize or copolymerize the α-olefin. The catalyst for polymerization of α-olefin according to the present invention can be applied to not only a solution polymerization using a solvent, but also a liquid-phase non-solvent polymerization using substantially no solvent, a gas-phase polymerization or a melt polymerization. These polymerizations can be conducted either in a continuous manner or in a batch manner.

As the solvents used for the solution polymerization, there can be exemplified inert saturated aliphatic or aromatic hydrocarbons such as hexane, heptane, pentane, cyclohexane, benzene or toluene. These solvents can be used singly or in the form of a mixture of any two or more thereof. The polymerization temperature is usually in the range of −78° C. to 250° C., preferably −20° C. to 100° C. The olefin pressure in the reaction system is not particularly restricted, but preferably from ordinary pressure to 2,000 kgf/cm²G (Geuge), more preferably from ordinary pressure to 50 kgf/cm²G. Further, the molecular weight of the resultant α-olefin polymer can be controlled by known methods such as appropriate selection of reaction temperature and reaction pressure used or introduction of hydrogen.

As the raw α-olefins, there can be used α-olefins having usually 2 to 20 carbon atoms, preferably 2 to 10 carbon atoms. Specific examples of the α-olefins may include ethylene, propylene, 1-butene, 4-methyl-1-pentene, 1-hexene, 1-octene, 1-decene, 1-dodecene, 1-tetradecene, 1-hexadecene, 1-octadecene, 1-eicosene or the like. The catalyst according to the present invention can be preferably applied to stereoregulated polymerization of α-olefins having 3 to 10 carbon atoms, especially to the polymerization of propylene.

Further, the catalyst according to the present invention can be applied to not only homopolymerization or copolymerization of the afore-mentioned α-olefins, but also copolymerization of the α-olefins with the other monomers. As the other monomers copolymerizable with the α-olefins, there can be exemplified conjugated dienes or non-conjugated dienes such as butadiene, 1,4-hexadiene, 7-methyl-1,6-octadiene, 1,8-nonadiene or 1,9-decadiene; cyclic olefins such as cyclopropene, cyclobutene, cyclopentene, norbornene or dicyclopentadiene; or the like. The polymerization or copolymerization of the α-olefins can be performed in multiple stages whose reaction conditions are different from each other, i.e., in a manner of so-called multi-step polymerization, for example, block copolymerization comprising pre-polymerization of propylene and copolymerization of ethylene with the polypropyrene prepared by the said pre-polymerization.

As described above, in accordance with the polymerization method according to the present invention, there can be obtained an α-olefin polymer which has a narrow molecular weight distribution and a narrow composition distribution, is excellent in transparency and mechanical strength and exhibits a good flowability.

Also, in the case where the polymerization of propylene was conducted by using the catalyst according to the present invention, there can be obtained a crystalline polypropylene which can show a high value [mmmm] (e.g., not less than 90%) and a unique regio defect amount: 2,1-inversion of 0.5 to 2.0 mol % and 1,3-insertion of 0.06 to 0.40 mol %. The regio defect amount can be calculated according to the following formula:

2,1-insertion percentage (%)=(Y/X)×1,000×⅕, 1,3-insertion percentage (%)=(Z/X)×1,000×⅕, X=sum of integrated values from 27 ppm to 48 ppm, $Y=(A①+A②+A③+A④+A⑤+A⑥)/6$, $Z=(A⑦+A⑧+A⑨)/6$ In the above formulae, A①, A②, A③, A④, A⑤, A⑥, A⑦, A⑧ and A⑨ are areas at 42.3 ppm, 35.9 ppm, 38.6 ppm, 30.6 ppm, 36.0 ppm, 31.5 ppm, 31.0 ppm, 37.2 ppm and 27.4 ppm, respectively, and indicate ratios between quantities of carbon atoms existing at respective positions of the following partial structures (I) and (II):

Substructure (I):

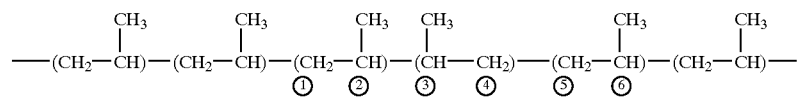

Substructure (II):

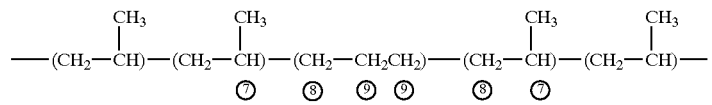

In addition, in accordance with the present invention, there can be provided novel transition metal compounds. Especially, in the case where the catalyst containing the transition metal compound represented by the general formulae (II)–(VI) according to the present invention is used, the α-olefin polymer which is free from reduction of its molecular. weight and deterioration of its stereo regularity, can show a high molecular weight and a high melting point, and therefore, is applicable to extrusion molding or injection molding, can be produced with a high yield. The reason therefor is considered as follows, though not exactly known.

That is, in the novel transition metal compound represented by the general formulae (II) and (III), since the groups $R^3$ and $R^6$ each form a condensed ring having not less than 7 members, the substituent groups $R^7$ and $R^8$ bonded thereto take such a spatial arrangement as inclined at a certain angle relative to a plane of the condensed ring constituted by the 5-membered ring and the $R^3$ or $R^6$. In addition, the substituent groups $R^7$ and R8 contain halogen atom(s) which is spatially bulkier than a hydrogen atom. The halogen atom acts to provide an appropriate steric hindrance and an appropriate configuration which cannot be achieved only by the hydrocarbon. As a result, effects of regulating the direction of growth of polymer chains and the direction of coordination of monomers are enhanced, thereby improving the stereo regularity of the obtained polymers and further increasing the melting point thereof.

Further, it is considered that the halogen atom exerts an electronic effect on centrally located metals, e.g., zirconium or hafnium, and the electronic effect and the afore-mentioned stereostructure can effectively prevent the chain transfer reaction, thereby increasing a molecular weight of the obtained polymer. Furthermore, since the 7- to 10-membered ring formed by the groups $R^3$ or $R^6$ has double bond(s), the movement of the substituent groups $R^7$ and $R^8$ is inhibited and configuration of the ligands is firmly fixed. For this reason, it is considered that even if the polymerization temperature is increased, the substituent groups $R^7$ and $R^8$ do not lose the effects of regulating the direction of growth of polymer chains and the direction of coordination of monomers, thereby obtaining a high-molecular weight polymer having an excellent stereo regularity.

In the novel transition metal compound represented by the general formula (IV), since the substituent group $R^6$ forms a condensed ring having not less than 7 members, the substituent group $R^8$ bonded thereto has such a spatial arrangement as inclined at a certain angle relative to a plane of the condensed ring constituted by the 5-membered ring and the $R^6$. In addition, the substituent group $R^8$ is present at a β- or remoter position on $R^6$ with respect to the 5-membered ring. These conditions allow the transition metal compound to have a spatially bulkier structure, thereby imparting an appropriate steric hindrance and an appropriate configuration thereto. As a result, the same effects as given by the transition metal compound of the general formula (II) car be obtained.

In the novel transition metal compound represented by the general formula (V), since the substituent group $R^3$ and $R^6$ forms a condensed ring having not less than 7 members, the substituent group $R^7$ and $R^8$ bonded thereto has such a spatial arrangement as inclined at a certain angle relative to a plane of the condensed ring constituted by the 5-membered ring and the $R^3$ or $R^6$. In addition, bulkier $R^1$ and $R^4$ are bonded to the 5-membered ring. These conditions allow the transition metal compound to have a spatially bulkier structure, thereby imparting an appropriate steric hindrance and an appropriate configuration thereto. As a result, the same effects as provided by the transition metal compound of the general formula (II) can be obtained.

Further, in the novel transition metal compound represented by the general formula (VI), since the groups $R^3$ and $R^6$ each form a condensed ring having not less than 7 members, the substituent groups $R^7$ and $R^8$ bonded thereto have such a spatial arrangement as inclined at a certain angle relative to a plane of the condensed ring constituted by the 5-membered ring and the $R^3$ or $R^6$. In addition, the cyclic substituent group A is bonded to the cross-linking group Q. These conditions allow the transition metal compound to have a spatially bulkier structure, thereby imparting an appropriate steric hindrance and an appropriate configuration thereto. As a result, the same effects as provided by the transition metal compound of the general formula (II) can be obtained. Moreover, since the 7- to 10-membered ring formed by the groups $R^3$ or $R^6$ and the group A contain double bonds therein, the movements of the substituent groups $R^7$, $R^8$ and $R^a$ are inhibited so that configuration of the ligands is firmly fixed. For this reason, it is considered that even if the polymerization temperature is increased, it is possible to obtain a high-molecular weight polymer having an excellent stereo regularity.

EXAMPLES

The present invention is described in more detail below by way of examples, but these examples are not intended to limit the scope of the present invention. Incidentally, in the following examples, all the catalyst preparation processes and polymerization processes were conducted in a purified nitrogen atmosphere. In addition, solvents were dehydrated with MS-4A and then deaerated by bubbling with purified nitrogen before they were used for these processes. Further, the activity of each solid catalyst component per unit weight thereof is referred to as "catalytic activity" and indicated by a unit of "g-polymer/g-solid catalyst component", whereas the activity of each complex component per unit weight thereof is referred to as "complex activity" and indicated by a unit of "g-polymer/g-complex component".

(1) Measurement of Melt Flow Rate (MFR):

Six grams of an acetone solution containing 0.6% by weight of a thermal stabilizer (BHT) was added to 6 g of the obtained polymer. After drying, the polymer was charged into a melt indexer (230° C.) and allowed to stand for 5 minutes under a load of 2.16 Kg. Thereafter, the polymer was extruded to measure the amount of the extruded polymer. Based on the thus-measured amount of the extruded polymer, the amount per 10 minutes was calculated and used as a value of MFR.

(2) Measurement of Molecular Weight Distribution:

The molecular weight distribution of the obtained polymer was determined from the Q-value (Mw/Mn) of weight-average molecular weight (Mw) to number-average molecular weight (Mn) thereof which were measured by gel permeation chromatography (GPC). The measurement of the molecular weights was conducted at 135° C. by a GPC apparatus (150 CV type manufactured by Waters), using ortho-dichlorobenzene as a solvent.

(3) Measurement of Melting Point:

Using a differential scanning calorimeter (DSC) manufactured by E. I. du Pont, the melt flow rate of the obtained polymer was measured after the polymer was heated two times from 20° C. to 200° C. at a heating rate of 10° C./min.

(4) Measurement of Stereo Regularity:

300 mg of the polymer sample was dissolved in a mixed solvent composed of 2.5 ml of ortho-dichlorobenzene and 0.5 ml of benzene-$d_6$. The obtained solution was subjected to a nuclear magnetic resonance (NMR) analysis by using JEOL EX-270 Spectrometer. The NMR analysis was conducted at a temperature of 130° C., an irradiation time of 0.744 sec and a pulse delay of 2.256 sec, and cumulatively repeated 20,000 times to determine a stereo regularity of the obtained polymer.

Example 1

(1) Chemical Treatment of Clay Minerals:

Thirty grams of a 35% hydrochloric acid solution was diluted with 70 ml of desalted water. Next, 11.7 g of commercially available montmorillonite ("KUNIPIA F" produced by KUNIMINE INDUSTRIES CO., LTD.) was dispersed in the dilute solution. The resultant dispersion was heated up to a boiling point thereof while stirring and boiled for 2 hours. Thereafter, the product was sufficiently washed with desalted water and, after pre-drying, dried at 200° C. for 2 hours under a reduced pressure to obtain a component (B).

(2) Preparation of Solid Catalyst Component:

3.0 g of the chemically treated montmorillonite obtained in the above item (1) was charged into a 100 ml flask and dispersed in 20 ml of toluene to obtain a slurry. Successively, 1.3 ml of triethylaluminum was added to the slurry at room temperature while stirring. After stirring the slurry at room temperature for one hour, the supernatant was removed and the solid residue was washed with toluene to obtain a solid catalyst component.

(3) Synthesis of dimethylsilylene bis{1,1'-(2-methyl-4-phenyl-4-hydroazulenyl}zirconium dichloride (Component (A)):

(a) Synthesis of Racemic and Meso Mixture:

2.22 g of 2-methylazulene produced according to the method described in Japanese Patent Application Laid-Open (KOKAI) No. 62-207232, was dissolved in 30 ml of hexane. 15.6 ml of a cyclohexane/diethyl ether solution of phenyl lithium (1.0 equivalent) was gradually added to the above-obtained hexane solution at 0° C. After-stirring at room temperature for one hour, the obtained solution was cooled to −78° C., and then mixed with 30 ml of tetrahydrofuran. The solution was mixed with 0.95 ml of dimethyldichlorosilane and the temperature thereof was raised to room temperature. The solution was further heated to 50° C. and stirred for 1.5 hours. After an aqueous ammonium chloride solution was added, the solution was separated into aqueous and organic phases. The organic phase was dried with magnesium sulfate and stirred under a reduced pressure to remove the solvent. The thus-obtained crude product was purified by column chromatography (hexane:dichloromethane=5:1) to obtain 1.48 g of dimethyl bis{1,1'-(2-methyl-4-phenyl-1,4-dihydroazulenyl)silane.

768 mg of the thus-produced dimethyl bis{1,1'-(2-methyl-4-phenyl-1,4-dihydroazulenyl}silane was dissolved in 15 ml of diethyl ether. 1.98 ml of a hexane solution of n-butyl lithium (1.64 mol/liter) was dropped into the solution at −78° C., and the solution was stirred for 12 hours while the temperature thereof was gradually raised to room temperature. The solvent was removed under a reduced pressure, thereby obtain a solid component. The obtained solid component was washed with hexane, and then dried and solidified under a reduced pressure. 20 ml of a mixed solvent composed of toluene and diethyl ether (40:1) was added to the dried product, and further 325 mg of zirconium tetrachloride was added thereto at −60° C. The mixture was stirred for 15 hours while the temperature thereof was gradually raised to room temperature. The obtained solution was concentrated under a reduced pressure and then mixed with hexane to obtain, as a precipitate, 150 mg of a racemic and mesa mixture of dimethylsilylene bis{1,1'-(2-methyl-4-phenyl-4-hydroazulenyl}zirconium dichloride (a mixture showing the below-mentioned spectrum data).

(b) Purification of Racemic Compound:

887 mg of the above-produced racemic and meso mixture was dissolved in 30 ml of dichloromethane and charged into a Pyrex vessel equipped with a 100W high-pressure mercury vapor lamp. While stirring, the solution was irradiated (300 nm to 600 nm) for 30 minutes under atmospheric pressure to enhance a percentage of the racemic compound in the mixture, and stirred under a reduced pressure to remove the solvent. 7 ml of toluene was added to the obtained yellow solid. After stirring, the mixture was allowed to stand to precipitate the yellow solid, followed by removing the supernatant. Similar washing procedures were repeated three times using 4 ml of toluene, 2 ml of toluene and 2 ml of hexane. The thus-obtained solid product was dried and solidified under a reduced pressure to obtain 437 mg of a racemic compound of dimethylsilylene bis{1,1'-(2-methyl-4-phenyl-4-hydroazulenyl}zirconium dichloride.

(c) Chemical Shift of $^1$H-NMR of Racemic Compound:

300 MHz, $C_6D_6$ (ppm) δ 0.51 (s, 6H, Si(CH$_3$)$_2$), 1.92 (s, 6H, CH$_3$), 5.30 (br d, 2H), 5.75–5.95 (m, 6H), 6.13 (s, 2H), 6.68 (d, J=14 Hz, 2H), 7.05–7.20 (m, 2H, arom), 7.56 (d, J=7 Hz, 4H)

(d) Chemical Shift of $^1$H-NMR of Meso Compound:

300 MHz, $C_6D_6$ (ppm) δ 0.44 (s, 6H, SiCH$_3$), 0.59 (s, 6H, SiCH$_3$), 1.84 (s, 6H, CH$_3$), 5.38 (br d, 2H), 5.75–6.00 (m, 6H), 6.13 (s, 2H), 6.78 (d, J=14 Hz, 2H), 7.00–7.20 (m, 2H, arom), 7.56 (d, J=7 Hz, 4H)

(4) Polymerization of Propylene:

0.5 mmol (calculated as Al atom) of triethylaluminum (produced by TOSOH AKZO CORP.) and 100 mg of the solid catalyst component obtained in the above item (2) were charged into a 2-liter stirring-type autoclave. On the other hand, 0.975 mg (1.5 μmol) of the above-prepared racemic compound as a component (A) was diluted with 3 ml of toluene and charged into a catalyst feeder equipped with a safety rupture disc. Thereafter, 1,500 ml of propylene was charged into the autoclave and the content of the autoclave was heated to 70° C. Successively, an argon gas having a pressure of 80 kgf/cm$^2$G was introduced into the catalyst feeder to break the safety rupture disc, so that the component (A) was supplied into the autoclave to initiate the polymerization of propylene.

After the polymerization was continued for 2 hours, unreacted propylene-was purged to obtain 166.5 g of polypropylene. As a result of the measurements, it was confirmed that the catalyst activity was 1665 and the complex activity was 17.1×10$^4$. Further, it was confirmed that the obtained polypropylene had a melting point (Tm) of 150.1° C., a melt flow rate (MFR),of 2.5, a weight-average molecular weight (Mw) of 3.1×10$^5$ and a Q-value (Mw/Mn) of 2.8. The measurement of $^{13}$C-NMR spectrum showed that the [mmmm] was 98.9%, the 2,1-inversion was 0.9% and the 1,3-insertion was 0.08%. The results are shown in Tables 1 and 2.

Reference Example 1
<Polymerization of Propylene>

4 mmol (calculated as Al atom) of methylalumoxane ("MMAO" produced by TOSOH AKZO CORP.) and 0.26 mg (0.4 μmol) of the racemic compound obtained in Example 1 were charged into a 2-liter stirring-type autoclave. Further, 1,500 ml of propylene was charged into the autoclave and the content of the autoclave was heated to 70° C. to conduct the polymerization of propylene for one hour, thereby obtaining 43.5 g of polypropylene. As a result of the measurements, it was confirmed that the complex activity was 16.7×10$^4$ and the obtained polypropylene had a melting point (Tm) of 150.9° C., a melt flow rate (MFR) of 1.3, a weight-average molecular weight (Mw) of 3.5×10$^5$ and a Q-value (Mw/Mn) of 2.7. Further, the measurement of $^{13}$C-NMR spectrum showed that the [mmmm] was 99.0%, the 2,1-inversion was 0.9% and the 1,3-insertion was 0.10%. The results are shown in Tables 1 and 2.

Example 2
<Polymerization of Propylene>

The same procedure as defined in Example 1(3) was conducted except that the polymerization temperature was changed to 80° C., to obtain 235 g of polypropylene. As a result of the measurements, it was confirmed that the catalyst activity was 2350 and the complex activity was 24.1×10$^4$, and the obtained polypropylene had a melting point (Tm) of 148.8° C., a melt flow rate (MFR) of 8.5, a weight-average molecular weight (Mw) of 2.1×10$^5$ and a Q-value (Mw/Mn) of 2.7. Further, the measurement of $^{13}$C-NMR spectrum showed that the [mmmm] was 98.8%, the 2,1-inversion was 0.9% and the 1,3-insertion was 0.06%. The results are shown in Tables 1 and 2.

Example 3
<Polymerization of Propylene>

500 ml of dried and deaerated toluene, 0.5 mmol (calculated as Al atom) of triethylaluminum (produced by TOSOH AKZO CORP.) and 100 mg of the solid catalyst component obtained in the above Example 1(2) were charged into a 1.5-liter stirring-type autoclave whose interior was sufficiently dried and replaced with a propylene gas. While maintaining at 20° C., the autoclave was charged with 4 μmol of the racemic compound obtained in Example 1. Thereafter, the reaction system in the autoclave was heated to 70° C. to initiate the polymerization of propylene while adjusting the propylene pressure in the autoclave to 5 kgf/cm²G. After the polymerization was continued for one hour, unreacted propylene was purged and obtained a slurry containing a polymer. The slurry was filtered and dried to recover 17 g of polypropylene. Further, the filtrate was concentrated so that 0.05 g of polypropylene dissolved in the filtrate was recovered. As a result of the measurements, it was confirmed that the catalyst activity was 170 and the complex activity was $0.65 \times 10^4$, and the obtained polypropylene had a melting point (Tm) of 150.9° C., a melt flow rate (MFR) of 3.5, a weight-average molecular weight (Mw) of $3.0 \times 10^5$ and a Q-value (Mw/Mn) of 2.8. The measurement of $^{13}$C-NMR spectrum showed that the [mmmm] was 99.0%, the 2,1-inversion was 0.7% and the 1,3-insertion was 0.10%. The results are shown in Tables 1 and 2.

Example 4

(1) Chemical Treatment and Granulation of Clay Minerals:

3 Kg of commercially available montmorillonite was pulverized by a vibrating ball mill and dispersed in 16 liters of 3% hydrochloric acid solution. The dispersion was heated at 90° C. for 3 hours while stirring to obtain an aqueous slurry of chemically treated montmorillonite. Successively, after the solid content of the aqueous slurry was adjusted to 15%, the slurry was sprayed by means of a spray drier to conduct granulation of the solid component, followed by washing with desalted water. The thus-obtained particles had a spherical shape.

Next, 10.0 g of the chemically treated montmorillonite obtained in the above was charged into a 200 ml flask and subjected to heating and desiccation treatment at 200° C. for 2 hours under a reduced pressure. It was confirmed that the weight of the montmorillonite was reduced by 1.3 g as a result of the heating and desiccation treatment.

(2) Preparation of Solid Catalyst Component:

3.0 g of the chemically treated montmorillonite obtained in the above (1) was charged into a 100 ml flask and dispersed in 20 ml of toluene to obtain a slurry. Successively, 1.3 ml of triethylaluminum was added to the slurry at room temperature while stirring. After both the components were contacted with each other at room temperature for one hour, the supernatant was removed and the solid residue was washed with toluene to obtain a solid catalyst component.

(3) Polymerization of Propylene:

0.5 mmol (calculated as Al atom) of triethylaluminum (produced by TOSOH AKZO CORP.), 100.0 mg of the solid catalyst component obtained in the above (2) and 750 g of liquid propylene were charged into a 2-liter stirring-type autoclave. Thereafter, the content of the autoclave was heated to 70° C. and then supplied with 5.0 ml of a toluene solution containing dimethylsilylene bis{1,1'-(2-methyl-4-phenyl-4-hydroazulenyl}zirconium dichloride (2.0 μmol/ml) as a complex component. The polymerization of propylene was continued at 70° C. for 2 hours while stirring. After completion of the polymerization, unreacted propylene was purged to obtain 180 g of polypropylene. As a result of the measurements, it was confirmed that the catalyst activity was 1800 and the complex activity was $2.7 \times 10^4$, and the obtained polypropylene had a melting point (Tm) of 148.4° C., a melt flow rate (MFR) of 11.1, a weight-average molecular weight (Mw) of $1.9 \times 10^5$ and a Q-value (Mw/Mn) of 2.7. Further, the measurement of $^{13}$C-NMR spectrum showed that the [mmmm] was 98.8%, the 2,1-inversion was 0.9% and the 1,3-insertion was 0.10%. The results are shown in Tables 1 and 2.

Example 5

<Copolymerization of Propylene and Ethylene>

0.5 mmol (calculated as Al atom) of triethylaluminum, 100.0 mg of the solid catalyst component obtained in Example 1 and 750 g of liquid propylene were charged into a 2-liter stirring-type autoclave. After the content of the autoclave was heated to 70° C., 3.0 ml of a toluene solution containing dimethylsilylene bis{1,1'-(2-methyl-4-phenyl-4-hydroazulenyl}zirconium dichloride (2.0 μmol/ml) as a complex component was supplied into the autoclave together with pressurized ethylene. The supply of ethylene was continued such that the mole percentage of (ethylene) to (propylene+ethylene) in a gas composition within the autoclave was 3–5 mol %. Under this condition, the polymerization of propylene was continued at 70° C. for 2 hours while stirring. After completion of the polymerization, unreacted propylene and unreacted ethylene were purged to obtain 230 g of polypropylene/ethylene copolymer. As a result of the measurements, it was confirmed that the catalyst activity was 3830, the complex activity was $5.9 \times 10^4$, and the thus-obtained polypropylene/ethylene copolymer had an ethylene content of 0.8 mol %, a melting point (Tm) of 141.7° C., a melt flow rate (MFR) of 9.7, a weight-average molecular weight (Mw) of $2.1 \times 10^5$ and a Q-value (Mw/Mn) of 2.6. Further, the measurement of $^{13}$C-NMR spectrum showed that the [mmmm] was 98.8%, the 2,1-inversion was 0.8% and the 1,3-insertion was 0.08%. The results are shown in Tables 1 and 2.

Comparative Example 1

(1) Synthesis of dimethylsilylene bis{1,1'-(2-methyl-4,5-benzoindenyl}zirconium dichloride:

Dimethylsilylene bis{1,1'-(2-methyl-4,5-benzoindenyl}zirconium dichloride was synthesized according to the method described in Example 7 of Japanese Patent Application Laid-open (KOKAI) No. 8-208733.

(2) Polymerization of Propylene:

The same procedure as defined in Example 1 was conducted except that the afore-mentioned compound (in item (1)) was used as the component (A) and the polymerization time was one hour, to obtain 160 g of polypropylene. As a result of the measurements, it was confirmed that the catalyst activity was 1600, the complex activity was $5.8 \times 10^4$, and the obtained polypropylene had a melting point (Tm) of 132.0° C., a melt flow rate (MFR) of 200, a weight-average molecular weight (Mw) of $1.1 \times 10^5$ and a Q-value (Mw/Mn) of 2.2. Further, the measurement of $^{13}$C-NMR spectrum showed that the [mmmm] was 95.1%, the 2,1-inversion was 0.8% and the 1,3-insertion was not detected. The results are shown in Tables 1 and 2.

Comparative Example 2

<Polymerization of Propylene>

The same procedure as defined in Reference Example 1 was conducted except that the afore-mentioned compound synthesized in Comparative Example 1 was used as the component (A) and the polymerization temperature was adjusted to 70° C., to obtain 155.2 g of polypropylene. As a result of the measurements, it was confirmed that the complex activity was $67.5 \times 10^4$, and the obtained polypropylene had a melting point (Tm) of 151.5° C., a melt flow rate (MFR) of 2.0, a weight-average molecular weight (Mw) of $3.8 \times 10^5$ and a Q-value (Mw/Mn) of 2.1. Further, the measurement of $^{13}$C-NMR spectrum showed that the [mmmm] was 95.5%, the 2,1-inversion was 0.4% and the 1,3-insertion was not detected. The results are shown in Tables 1 and 2.

TABLE 1

| | Catalyst | | | Evaluation (catalyst performance) | |
|---|---|---|---|---|---|
| | Component (A) | Component (C) | Conditions of polymerization | Catalytic activity | Complex activity ($\times 10^4$) |
| Ex. 1 | (1)* | Triethyl aluminum | 70° C./bulk/2 Hr | 1665 | 17.1 |
| Ref. Ex. 1 | (1) | MMAO | 70° C./bulk/1 Hr | — | 16.7 |
| Ex. 2 | (1) | Triethyl aluminum | 80° C./bulk/2 Hr | 2350 | 24.1 |
| Ex. 3 | (1) | Triethyl aluminum | 70° C., 5 kgf/cm²G/ slurry/ 1 Hr | 170 | 0.65 |
| Ex. 4 | (1) | Triethyl aluminum | 70° C./bulk/2 Hr | 1800 | 2.7 |
| Ex. 5 | (1) | Triethyl aluminum | 70° C./bulk + ethylene/2 Hr | 3830 | 5.9 |
| Comp. Ex. 1 | (2)** | Triethyl aluminum | 70° C./bulk/1 Hr | 1600 | 5.8 |
| Comp. Ex. 2 | (2) | MMAO | 70° C./bulk/1 Hr | — | 67.5 |

Note:
(1)*: dimethylsilylene bis{1,1'-(2-methyl-4-phenyl-4-hydroazulenyl} zirconium dichloride;
(2)**: dimethylsilylene bis{1,1'-(2-methyl-4,5-benzoindenyl} zirconium dichloride

TABLE 2

| | Properties of polymer | | | |
|---|---|---|---|---|
| | Melting point (° C.) | MFR (g/10 min) | Mw ($\times 10^5$) | Q (Mw/Mn) |
| Example 1 | 150.1 | 2.5 | 3.1 | 2.8 |
| Reference Example 1 | 150.9 | 1.3 | 3.5 | 2.7 |
| Example 2 | 148.8 | 8.5 | 2.1 | 2.7 |
| Example 3 | 150.9 | 3.5 | 3.0 | 2.8 |
| Example 4 | 148.4 | 11.1 | 1.9 | 2.7 |
| Example 5 | 141.7 | 9.7 | 2.1 | 2.6 |
| Comparative Example 1 | 132.0 | 200 | 1.1 | 2.2 |
| Comparative Example 2 | 151.5 | 2.0 | 3.8 | 2.1 |

| | [mmmm] (%) | 2,1-(mol %) | 1,3-(mol %) |
|---|---|---|---|
| Example 1 | 98.9 | 0.9 | 0.08 |
| Reference Example 1 | 99.0 | 0.9 | 0.10 |
| Example 2 | 98.8 | 0.9 | 0.06 |
| Example 3 | 99.0 | 0.7 | 0.10 |
| Example 4 | 98.8 | 0.9 | 0.10 |
| Example 5 | 98.8 | 0.8 | 0.08 |
| Comparative Example 1 | 95.1 | 0.8 | not detected |
| Comparative Example 2 | 95.5 | 0.4 | not detected |

Example 6

(1) Synthesis of dimethylsilylene bis{1,1'-(2-ethyl-4-phenyl-4-hydroazulenyl}zirconium dichloride as Component (A):

(a) Synthesis of tosyltropolone:

25.58 g (210 mmol) of tropolone was dissolved in 30 ml of pyridine. 60 ml of a pyridine solution containing 40.77 g (214 mmol) of tosyl chloride was added to the tropolone-containing solution at room temperature. After stirring overnight at room temperature, the resultant reaction solution was supplied with water to deposit a crystallized product. The crystallized product was separated by filtration and dried at 50° C. under a reduced pressure to obtain 57.61 g of tosyltropolone (yield: 99.5%).

(b) Synthesis of 3-propionylcycloheptafuran-2-one:

8.07 g (29.2 mmol) of tosyl tropolone and 6.2 ml (43.8 mmol) of ethyl propionylacetate were suspended in 30 ml of ethanol. A solution containing sodium ethoxide prepared from 60 ml of ethanol and 806 mg (35.1 mmol) of sodium was added to the suspension at 0° C. The mixture was stirred overnight at room temperature and then heated at 50° C. for 45 minutes. The resultant reaction solution was concentrated up to two times an initial concentration thereof. The concentrated solution was supplied with water to obtain a crystallized product. The crystallized product was separated from the reaction solution by filtration. Further, the filtrate was concentrated to crystallize the reaction product remaining therein. The crystallized product obtained from the filtrate was also separated from the solution by filtration. The products thus-obtained from the reaction solution and the filtrate were mixed together and dried under a reduced pressure to obtain 3.62 g of 3-propionylcycloheptafuran-2-one (yield: 61%).

(c) Synthesis of 1-cyano-2-ethylazulene-3-carboxylic acid:

3.62 g (17.9 mmol) of 3-propionylcycloheptafuran-2-one and 3.8 ml (35.8 mmol) of ethyl cyanoacetate were dissolved in 50 ml of ethanol. The solution was mixed with a solution of sodium ethoxide prepared from 80 ml of ethanol and 1.65 g (71.7 mmol) of sodium, at 0° C. After the mixed solution was stirred overnight at room temperature, the obtained reaction solution was concentrated up to two times an initial concentration thereof. The concentrated solution was diluted with 200 ml of water and extracted with dichloromethane. Thereafter, an aqueous phase of the extract was mixed with dilute hydrochloric acid to acidify the aqueous phase, thereby obtaining a crystallized product. After filtration, the crystallized product was dried under a reduced pressure to obtain 3.73 g of 1-cyano-2-ethylazulene-3-carboxylic acid (yield: 93%).

(d) Synthesis of 2-ethylazulene:

3.7 g (16.4 mmol) of the above-obtained 1-cyano-2-ethylazulene-3-carboxylic acid was separated into two parts, i.e., about 1 g and a remaining part. 30 ml of 75% sulfuric acid was added to the first part, i.e., about 1 g of 1-cyano-2-ethylazulene-3-carboxylic acid and heated to 90° C., and thereafter gradually supplied with the remaining part of 1-cyano-2-ethylazulene-3-carboxylic acid. The mixture was heated at 90° C. for 2 hours and further at 120° C. for 2 hours. The obtained reaction solution was added to an aqueous solution containing 35 g of sodium hydroxide and extracted with a mixed solution of hexane and ethyl acetate. An organic phase of the extract was removed under a reduced pressure. The resultant crude product was purified by silica gel column chromatography, to obtain 1.71 g of 2-ethyl azulene (yield: 67%)

(e) Synthesis of bis{1,1'-(2-ethyl-4-phenyl-1,4-dihydroazulenyl}dimethyl silane:

A diethyl ether/cyclohexane solution containing 10.9 mmol (0.1 M) of phenyl lithium was added to 20 ml of a hexane solution containing 1.7 g (10.9 mmol) of 2-ethylazulene at 0° C. After stirring at room temperature for 1.5 hours, the solution was mixed with 20 ml of tetrahydrofuran at 0° C. Further, 0.66 ml (5.45 mmol) of dichlorodimethylsilane was added to the solution at −78° C., followed by stirring at room temperature for one hour and then at 50° C. for 3 hours. After the mixed solution was allowed to stand at room temperature overnight, an aqueous solution of ammonium chloride was added the obtained reaction solution. The solution was separated into aqueous and organic phases. The organic phase was dried with magnesium sulfate, and the solvent was removed under a reduced pressure. The obtained crude product was purified by a column chromatography using a mixed solvent composed of hexane and dichloromethane (10:1 to 5:1) as an eluent solvent to obtain 1.07 g of bis{1,1'-(2-ethyl-4-phenyl dihydroazulenyl)dimethyl silane (yield: 37%).

(f) Synthesis of dimethylsilylene bis{1,1'-(2-ethyl-4-phenyl-4-hydroazulenyl}zirconium dichloride:

A hexane solution containing 6.62 mmol of n-butyl lithium was added to 15 ml of a diethyl ether solution containing 3.32 mmol of the above-produced bis{1,1'-(2-ethyl-4-phenyl-1,4-dihydroazulenyl}dimethylsilane at $-78°$ C. After the solution was stirred at room temperature overnight, the solvent was removed under reduced pressure. 10 ml of toluene and 0.25 ml of diethyl ether were added to the product to form a solution, and 775 mg (3.32 mmol) of zirconium tetrachloride was added to the solution at $-70°$ C. The temperature of obtained reaction solution was gradually raised to room temperature and stirred at room temperature for 3 hours. Successively, the reaction solution was filtered through celite, and the obtained solid component was washed with 6 ml of toluene and 6 ml of hexane. The thus-obtained solid component was dissolved in 30 ml of dichloromethane, and the solvent was removed under a reduced pressure. The resultant concentrated solution was supplied with 10 ml of hexane to form a precipitate. The precipitate was separated from the solution, and then dried and solidified under a reduced pressure to obtain 450 mg of a racemic and meso mixture of dimethylsilylene bis{1,1'-(2-ethyl-4-phenyl-4-hydroazulenyl}zirconium dichloride (yield: 20%).

(a) Purification of Racemic Compound:

400 mg of the above-produced racemic and meso mixture was dissolved in 15 ml of dichloromethane and charged into a Pyrex vessel equipped with a 100 W high-pressure mercury vapor lamp. While stirring, the solution was irradiated with light under normal pressure for 10 minutes to enhance the percentage of the racemic compound therein. Thereafter, dichloromethane was removed under a reduced pressure. The obtained yellow solid was mixed with 5 ml of toluene to form a solution, followed by stirring the solution. After the solution was filtered, the obtained solid component was washed with 6 ml of hexane to obtain 173 mg of the racemic compound of dimethylsilylene bis{1,1'-(2-ethyl-4-phenyl-4-hydroazulenyl)zirconium dichloride.

The chemical shifts of $^1$H-NMR of the above-obtained racemic compound are as follows.

300 MHz, $CDCl_3$ (ppm) 1.00 (s, 6H, $SiMe_2$), 1.05 (t, $^3J=8$ Hz, 6H, $CH_3CH_2$), 2.42 (sext, $^3J=8$ Hz, $^2J=15$ Hz, 2H, $CH_3CHH'$), 2.60 (sext, $^3J=8$ Hz, $^2J=15$ Hz, 2H, $CH_3CHH'$), 4.94 (br s, 2H, 4-H), 5.83–5.95 (m, 4H), 5.99 (s, 2H), 6.08–6.12 (m, 2H), 6.75 (d, 2H, 8-H), 7.2–7.4 (m, 10H, arom).

(2) Polymerization of Propylene:

0.45 mmol of triethylaluminum, a slurry of chemically treated clay minerals described hereinafter in Example 11(2) and 700 ml of liquid propylene were charged into a 1-liter stirring-type autoclave at room temperature in the presence of a nitrogen stream, Further, 1.5 μmol of the racemic compound of dimethylsilylene bis{1,1'-(2-ethyl-4-phenyl-4-hydroazulenyl}zirconium dichloride produced in the above item (1) was dissolved in toluene, and the solution was charged into the autoclave together with a high pressure argon gas breaking through the safety rupture disk. The content of the autoclave was heated to 80° C. and the polymerization of propylene was conducted for one hour. Thereafter, unreacted propylene was purged to terminate the polymerization of propylene, thereby obtaining 180 g of polypropylene. As a result of the measurements, it was confirmed that the catalyst activity was 3600 and the complex activity was $17.6\times10^4$, and the obtained polypropylene had a melting point (Tm) of 149.2° C., a melt flow rate (MFR) of 11, a weight-average molecular weight (Mw) of $20\times10^5$ and a Q-value (Mw/Mn) of 2.5.

Reference Example 2
<Polymerization of Propylene>

4 mmol (calculated as Al atom) of methylalumoxane ("MMAO" produced by TOSOH AKZO CORP.) and a toluene solution containing 0.27 mg of a racemic compound of dimethylsilylene bis{1,1'-(2-ethyl-4-phenyl-4-hydroazulenyl}zirconium dichloride were charged into a 2-liter stirring-type autoclave. Further, 1,500 ml of propylene was introduced into the autoclave. The content of the autoclave was heated to 70° C., and the polymerization of propylene was conducted for one hour to obtain 239 g of polypropylene. As a result of the measurements, it was confirmed that the complex activity was $87.2\times10^4$, and the obtained polypropylene had a melting point (Tm) of 155.2° C., a melt flow rate (MFR) of 0.6, a weight-average molecular weight (Mw) of $4.7\times10^5$ and a Q-value (Mw/Mn), of 3.1.

Example 7

(1) Chemical Treatment of Clay Minerals:

10 g of lithium hectorite (Li-HT produced by TOPY KOGYO CO., LTD.) was weighed and charged into a 300 ml round bottom flask. 100 ml of desalted water was introduced into the flask to form a slurry. The slurry was charged into a mechanical stirrer. While stirring the slurry, 8.9 ml of $TiCl_4$ (EXTRA-HIGH GRADE produced by KISHIDA CHEMICAL CO., LTD.) was gradually dropped thereinto at room temperature. The slurry was further stirred for 3 hours, and then filtered to remove a solid component therefrom. The obtained solid component was washed with water until the pH of filtrate thereof became 5.0. After drying at 100° C. for 3 hours, the obtained filter cake was pulverized in a porcelain mortar and passed through a sieve to separate particles having a particle size of not more than 105 μm from the remainder. The thus-obtained particles were dried at 200° C. for 2 hours under a reduced pressure to obtain the component (B).

(2) Preparation of Solid Catalyst Component:

1.2 g of the $TiCl_4$-treated lithium hectorite obtained in the above item (1) was weighed and charged into a 100 ml flask in a nitrogen atmosphere. 12 ml of toluene was added into the flask to form a slurry. Separately, a toluene solution of triethylaluminum (0.9 mol/liter) was prepared. While the slurry containing $TiCl_4$-treated lithium hectorite was stirred, 6.4 ml of the separately prepared toluene solution of triethylaluminum was introduced into the slurry at room temperature. The slurry was stirred at room temperature for one hour, and then washed with toluene until the washing efficiency reached 1/100. As a result of the measurement, it was confirmed that the concentration of the slurry was 52.6 mg/ml.

(3) Polymerization of Propylene:

0.45 mmol of triisobutylaluminum, 1.9 ml of the catalyst slurry obtained in the above (2) and 1,500 ml of liquid propylene were charged into a 2-liter stirring-type autoclave at room temperature in the presence of a nitrogen stream. Separately, 2.0 mg (3.0 μmol) of a racemic compound of dimethylsilylene bis{1,1'-(2-methyl-4-phenyl-4- hydroazulenyl}zirconium dichloride was dissolved in 1.6 ml of toluene to form a solution. The solution was introduced into the autoclave together with a high pressure argon gas breaking through the safety rupture disk. The content of the autoclave was heated to 80° C. and the polymerization of propylene was conducted at that temperature for one hour. Thereafter, unreacted propylene was purged to terminate the polymerization of propylene, thereby obtaining 110 g of polypropylene. As a result of the measurements, it was confirmed that the catalyst activity was 1100, the complex activity was $5.5 \times 10^4$, and the obtained polypropylene had a melting point (Tm) of 147.0° C., a melt flow rate (MFR) of 24.2, a weight-average molecular weight (Mw) of $1.7 \times 10^5$ and a Q-value (Mw/Mn) of 2.9.

Example 8

(1) Chemical Treatment of Clay Minerals:

10 g of lithium hectorite (Li-HT produced by TOPY KOGYO CO., LTD.) was weighed and charged into a 300 ml round bottom flask. 100 ml of desalted water was introduced into the flask to form a slurry. The slurry was charged into a mechanical stirrer. While stirring the slurry, 25 ml of an aqueous solution containing 19.3 mg of $AlCl_3$ (EXTRA-HIGH GRADE produced by Wako Pure Chemical Industries, LTD.) was gradually dropped thereinto at room temperature. The slurry was further stirred for 3 hours, and then filtered to remove a solid component therefrom. The obtained solid component was washed with water until the pH of filtrate thereof became 5.0. After drying at 100° C. for 3 hours, the obtained filter cake was pulverized in a porcelain mortar and passed through a sieve to separate particles having a particle size of not more than 105 μm from the remainder:. The thus-obtained particles were dried at 200° C. for 2 hours under a reduced pressure to obtain the component (B).

(2) Preparation of Solid Catalyst Component:

1.1 g of the $AlCl_3$-treated lithium hectorite obtained in the above item (1) was weighed and charged into a 100 ml flask in a nitrogen atmosphere. 10 ml of toluene was added into the flask to form a slurry. While stirring the slurry containing the $AlCl_3$-treated lithium hectorite, 5.5 ml of a toluene solution of triethylaluminum (0.91 mol/liter) was introduced thereinto at room temperature. After stirring at room temperature for one hour, the slurry was washed with toluene until the washing efficiency reached 1/100. As a result of the measurement, it was confirmed that the concentration of the slurry was 35.7 mg/ml.

(3) Polymerization of Propylene:

0.45 mmol of triisobutylaluminum, 2–8 ml of the solid catalyst component slurry obtained in the above item (2) and 1,500 ml of liquid propylene were charged into a 2-liter stirring-type autoclave at room temperature in the presence of a nitrogen stream. Separately, 2.0 mg (3.0 μmol) of a racemic compound of dimethylsilylene bis{1,1'-(2-methyl-4-phenyl-4-hydroazulenyl}zirconium dichloride was dissolved in 1.6 ml of toluene to prepare a solution. The solution was introduced into the autoclave together with a high pressure argon gas breaking through the safety rupture disk. The content of the autoclave was heated to 80° C., and the polymerization of propylene was conducted at that temperature for one hour. Thereafter, unreacted propylene was purged to terminate the polymerization of propylene, thereby obtaining 68 g of polypropylene. As a result of the measurements, it was confirmed that the catalyst activity was 660, the complex activity was $3.4 \times 10^4$, and the obtained polypropylene had a melting point (Tm) of 147.3° C. and a melt flow rate (MFR) of 24.2.

Example 9

(1) Synthesis of dimethylsilylene bis{1,1'-(2-methyl-4-phenyl-4-hydroazulenyl}hafnium dichloride:

(a) Synthesis of Racemic and Meso Mixture:

3.22 g of 2-methylazulene was dissolved in 30 ml of hexane. 21 ml of a cyclohexane/diethyl ether solution of phenyl lithium (1.0 equivalent) was gradually added to the hexane solution at 0° C. After stirring at room temperature for 1.5 hours, the resultant solution was cooled to −78° C. and then mixed with 30 ml of tetrahydrofuran. The solution was further supplied with 45 μmol of 1-methylimidazole and 1.37 ml of dimethyldichlorosilane and the temperature thereof was raised to room temperature. The solution was stirred for one hour. After an aqueous ammonium chloride solution was added, the solution was separated into aqueous and organic phases. The organic phase separated was dried with magnesium sulfate and stirred under a reduced pressure to remove the solvent, thereby obtaining 5.84 g of a crude product of bis{1,1'-(2-methyl-4-phenyl-1,4-dihydroazulenyl}dimethylsilane.

The thus-obtained crude product of bis{1,1'-(2-methyl-4-phenyl-1,4-dihydroazulenyl}dimethylsilane was dissolved in 30 ml of diethyl ether. 14.2 ml of a hexane solution of n-butyl lithium (1.64 mol/liter) was dropped into the solution at −78° C., and the temperature of the solution was gradually raised to room temperature and stirred at room temperature for 12 hours. The solution was stirred under a reduced pressure to remove the solvent. Thereafter, 80 ml of a mixture of toluene and dimethyl ether (40:1) was added to the solution. Further, the solution was mixed with 3.3 g of hafnium tetrachloride at −60° C. and temperature thereof was gradually raised to room temperature, followed by stirring at room temperature for 4 hours. The obtained solution was concentrated under a reduced pressure to obtain a solid product. The obtained solid product was washed with toluene and extracted with dichloromethane to obtain 1.74 g of a racemic and meso mixture of dimethylsilylene bis{1,1'-(2-methyl-4-phenyl-4-hydroazulenyl}hafnium dichloride.

(b) Purification of Racemic Compound:

1.74 g of the racemic and meso mixture prepared by repeatedly conducting the above-mentioned reaction was dissolved in 30 ml of dichloromethane and charged into a Pyrex vessel equipped with a 100 W high-pressure mercury vapor lamp. While stirring, the solution was irradiated with light for 40 minutes under normal pressure to enhance a percentage of the racemic compound therein, and stirred under a reduced pressure to remove dichloromethane. 10 ml of toluene was added to the obtained yellow solid. After stirring, the mixture was filtered to separate a solid component therefrom. The thus-obtained solid component was washed with 8 ml of toluene and 4 ml of hexane to obtain 917 mg of a racemic compound of dimethylsilylene bis{1,1'-(2-methyl-4-phenyl-4-hydroazulenyl}hafnium dichloride.

(2) Polymerization of Propylene:

The same procedure as defined in Example 13(2) described hereinafter was conducted except that 1.12 mg of the racemic compound obtained in the above item (1) was used as the component (A) and the polymerization time was changed to 35 minutes, to obtain 163 g of polypropylene. As a result of the measurements, it was confirmed that the catalyst activity was 3260 and the complex activity was $25.0 \times 10^4$. Further, it was confirmed that the obtained polypropylene had a melting point (Tm) of 152.7° C., a melt flow rate (MFR) of 0.8, a weight-average molecular weight (Mw) of $4.1 \times 10^5$ and a Q-value (Mw/Mn) of 2.6.

Reference Example 3

4 mmol (calculated as Al atom) of methylalumoxane ("MMAO" produced by TOSOH AKZO CORP.) and 0.298 mg of the racemic compound obtained in the above item (1) of Example 9 were charged into a 2-liter stirring-type autoclave. Further, 1,500 ml of propylene was introduced into the autoclave. The content of the autoclave was heated to 70° C., and the polymerization of propylene was conducted at that temperature for one hour to obtain 32 g of polypropylene. As a result of the measurements, it was confirmed that the complex activity was $10.7 \times 10^4$, and the obtained polypropylene had a melting point (Tm) of 154.4° C., a melt flow rate (MFR) of 0.08, a weight-average molecular weight (Mw) of $8.4 \times 10^5$ and a Q-value (Mw/Mn) of 3.8.

Example 10

(1) Chemical Treatment of Clay Minerals:

22.20 g of commercially available montmorillonite ("KUNIPIA F" produced by KUNIMINE INDUSTRIES CO., LTD.) was dispersed in a solution prepared by dissolving 15.96 g of $MgSO_4$ in 134 ml of desalted water. The resultant dispersion was heated at 86° C. for one hour while stirring, thereby obtaining a wet cake. Next, the thus-obtained wet cake was dispersed in a solution prepared by dissolving 23.38 g of sulfuric acid and 29.16 g of $MgSO_4$ in 69.24 ml of desalted water, and then treated under reflux for 2 hours. Thereafter, the dispersion was filtered to separate a cake therefrom. The obtained cake was washed with water until the pH of filtrate therefrom reached 6. The resultant product was dried at 100° C. for 3 hours, pulverized in a porcelain mortar and passed through a sieve to separate particles having not more than 105 $\mu$m. The particles were dried at 200° C. for 2 hours under a reduced pressure, thereby obtaining the component (B).

(2) Production of Solid Catalyst Component and Pre-Polymerization of Propylene:

0.8796 g of the component (B) obtained in the above (1) was charged into a 100 ml flask in a nitrogen atmosphere. In addition, 3.5 ml of a toluene solution containing triethylaluminum in an amount of 0.50 mmol/ml was charged into the flask, and then mixture in the flask was stirred at room temperature for 45 minutes. Next, the mixture was filtered to separate a solid component therefrom. The thus-separated solid component was washed with toluene until the washing efficiency reached 1/100. Thereafter, the solid component was mixed with 15 ml of toluene to prepare a toluene slurry.

Separately, 0.6 ml of a toluene solution of triisobutylaluminum (0.50 mmol/ml) and 19.1 ml of a toluene solution of racemic dimethylsilylene bis{1,1'-(2-methyl-4-phenyl-4-hydroazulenyl)}hafnium dichloride (1.5 $\mu$mol/ml) obtained in Example 9(1) were charged into a 100 ml flask, and stirred at room temperature to obtain a solution. The thus-obtained solution was mixed with the above-prepared toluene slurry to form a slurry containing a solid catalyst component.

A 2-liter stirring-type autoclave was charged with 40 ml of toluene and then with 36 ml of the above-prepared slurry containing the solid catalyst component, at room temperature in the presence of a nitrogen stream. While maintaining the temperature of the autoclave at 24° C., 104 ml of propylene was introduced into the autoclave and subjected to pre-polymerization for 3 minutes to obtain a pre-polymerization catalyst slurry. The amount of the polymer obtained by the pre-polymerization was 2.98 g per one gram of the solid catalyst component. The concentration of the solid catalyst component in the obtained pre-polymerization catalyst slurry was 12.5 mg/ml.

(3) Block Copolymerization of Propylene:

0.40 mmol of triisobutylaluminum, the pre-polymerization catalyst slurry obtained in the above (2) which contained 50.0 mg of the solid catalyst component, 200 ml of hydrogen and 1,500 ml of liquid propylene were introduced into a 2-liter stirring-type autoclave. Thereafter, the content of the autoclave was heated to 75° C. to conduct the polymerization of propylene for 45 minutes. Thereafter, unreacted propylene was purged to terminate the polymerization of propylene, thereby obtaining 289 g of polypropylene. As a result of the measurements, it was confirmed that the catalyst activity was 5780, the complex activity was $2.4 \times 10^5$, and the obtained polypropylene had a melting point (Tm) of 151.8° C. and a melt flow rate (MFR) of 14.2.

After 17 g of the obtained polypropylene was removed from the autoclave, while maintaining the content of the autoclave at 60° C., the autoclave was supplied with propylene and then ethylene until propylene and ethylene pressures within the autoclave reached 10 $kgf/cm^2G$ and 20 $kgf/cm^2G$, respectively. The thus-supplied propylene and ethylene we-re polymerized with each other for 80 minutes while introducing a mixed gas of ethylene and propylene having a propylene partial pressure of 49.97% to maintain an internal pressure of the autoclave at 20 $kgf/cm^2G$. Thereafter, the mixed gas of ethylene and propylene was purged to terminate the polymerization, thereby obtaining 46 g of a ethylene/propylene rubber component. As a result of the measurements, it was confirmed that the catalytic activity was 978, the complex activity was $4.0 \times 10^4$, and the content of rubber component in the obtained block copolymer was 14.5% by weight and a melt flow rate (MFR) of 7.0.

Example 11

(1) Synthesis of dimethylgermylene{1.1'-(2-methyl-4-phenyl-4-hydroazulenyl}zirconium dichloride:

1.5 g of 2-methylazulene was dissolved in 38 ml of n-hexane. 9.8 ml of a cyclohexane/diethyl ether solution of phenyl lithium (1.08 M) was gradually dropped into the n-hexane solution at a temperature of 3° C. to 5° C. After stirring at room temperature for one hour, the resultant solution was cooled to 0° C., and then 38 ml of tetrahydrofuran was added. Further, 0.02 ml of 1-methylimidazole and 0.61 ml of dimethylgermanium dichloride were dropped into the solution. After stirring at 0° C. for 20 minutes, the temperature of the reaction solution was raised to room temperature, followed by stirring at room temperature for 3.5 hours. The reaction solution was mixed with a saturated aqueous solution of ammonium chloride and extracted with n-hexane. The extract was separated into aqueous and organic phases. The organic phase was washed with a saturated brine, and dried with magnesium sulfate. The dried product was stirred under a reduced pressure to remove the solvent remaining therein. 2.9 g of the thus-obtained concentrated residue was purified by a column chromatography, thereby obtaining 2.4 g of an amorphous solid product.

Next, 2.4 g of the thus-obtained amorphous solid product was dissolved in 30 ml of diethyl ether. 5.6 ml of an n-hexane solution of n-butyl lithium (1.59 M) was dropped into the diethyl ether solution at −78° C. After stirring at that temperature for 10 minutes, the temperature of the solution was gradually raised to room temperature. After further stirring at room temperature for 2 hours, the solution was allowed to stand overnight. The reaction solution was stirred under a reduced pressure to remove the solvent, and then mixed with 20 ml of toluene and 0.5 ml of diethyl ether. After cooling to −78° C., the reaction solution was mixed with 1.0 g of zirconium tetrachloride, the reaction temperature was gradually increased to room temperature, followed by stirring at room temperature for 5 hours in total. The obtained reaction solution was filtered through celite to separate a solid component therefrom. The thus-obtained solid component was washed with 5 ml of toluene two times and then extracted with dichloromethane. The extract was stirred under a reduced pressure to remove the solvent, thereby obtaining 0.93 g of a racemic and meso mixture (ratio of racemic to meso=about 6:4) of dimethylgermylene bis{1,1'-(2-methyl-4-phenyl-4-hydroazulenyl}zirconium dichloride (yield: 30%).

The chemical shifts of $^1$H-NMR of the above-obtained racemic and meso mixture are as follows.

300 MHz; CDCl$_3$ (ppm) 1.14 (s, meso SiMe), 1.18 (s, meso SiMe), 1.20 (s, meso SiMe), 2.16 (s, 2-Me), 4.98–5.00 (m, —CH=), 5.06–5.08 (m, —Ch=), 5.83–5.94 (m, —CH=), 6.06–6.3 (m, —CH=), 6.67 (s, —CH=), 6.71 (s, —CH=), 7.2–7.5 (m, aromatic ring)

(2) Chemical treatment of Clay Minerals and Preparation of Solid Catalyst Component:

10 g of montmorillonite ("KUNIPIA F" produced by KUNIMINE INDUSTRIES CO., LTD.) was dispersed in dilute sulfuric acid composed of 10 g of sulfuric acid and 90 ml of desalted water. The resultant dispersion was heated up to a boiling point thereof, followed by stirring at that temperature for 6 hours. Thereafter, the montmorillonite recovered was sufficiently washed with desalted water and, after pre-drying, dried at 200° C. for 2 hours to obtain a chemically treated clay minerals. 200 mg of the chemically treated montmorillonite was added to 0.8 ml of a toluene solution of triethylaluminum (0.5 mol/liter). The mixture was stirred at room temperature for one hour, and then washed with toluene to obtain a montmorillonite/toluene slurry containing montmorillonite in an amount of 20 mg/ml.

(3) Polymerization of Propylene:

0.5 mmol (calculated as Al atom) of triisobutylaluminum (produced by TOSOH AKZO CORP.) was charged into a 2-liter stirring-type autoclave. Separately, 2.1 mg of the above-prepared racemic and meso mixture of dimethylgermylene{1,1'-(2-methyl-4-phenyl-4-hydroazulenyl)zirconium dichloride obtained in the above (1) was diluted with 1.1 ml of toluene. The diluted racemic and meso mixture was charged into a catalyst feeder equipped with a safety rupture disc. Further, 100 mg of the triethylaluminum-treated montmorillonite obtained in the above (2) and 0.3 mmol (calculated as Al atom) of triisobutylaluminum were charged into the autoclave. Thereafter, 1,500 ml of propylene was introduced into the autoclave and the safety rupture disc of the catalyst feeder was broken at room temperature. After the content of the autoclave was heated to 80° C., and the polymerization of propylene was conducted at that temperature for one hour, thereby obtaining 69 g of polypropylene. As a result of the measurements, it was confirmed that the catalyst activity was 690 and the complex activity was 3.3×10$^5$. Further, it was confirmed that the polypropylene insoluble in boiled heptane had a melting point (Tm) of 147.9° C., a melt flow rate (MFR) of 7.3, a weight-average molecular weight (Mw) of 2.4×10$^5$ and a Q-value (Mw/Mn) of 2.4.

Example 12

(1) Synthesis of dimethylsilylene bis[1,1'-{2-methyl-4-(4-chlorophenyl)-4-hydroazulenyl}] zirconium dichloride:

(a) Synthesis of Racemic and Meso Mixture:

11.7 ml of a pentane solution containing 19.2 mmol of t-butyl lithium (1.64 M) was dropped into a solution prepared by dissolving 1.84 g (9.6 mmol) of 1-bromo-4-chlorobenzene in a mixed solvent composed of 10 ml of n-hexane and 10 ml of diethyl ether, at −78° C. The resultant solution was stirred at −5° C. for 1.5 hours, and then 1.2 g (8.6 mmol) of 2-methyl azulene was added to the resultant solution. The obtained reaction solution was stirred for 1.5 hours while the temperature thereof was gradually raised to room temperature.

Thereafter, the reaction solution was cooled to 0° C. and mixed with 15 μl (0.19 mmol) of 1-methylimidazole and then with 0.52 ml (4.3 mmol) of dimethyldichlorosilane. After the reaction solution was stirred at room temperature for 1.5 hours, dilute hydrochloric acid was added thereto to terminate the reaction. The reaction solution was separated into organic and aqueous phases, and the organic phase was concentrated under a reduced pressure. After dichloromethane was added to the concentrated organic phase, the mixture was dried with magnesium sulfate and stirred under a reduced pressure to remove the solvent. The thus-obtained product was purified by a silica gel column chromatography (a mixed solvent: dichloromethane and n-hexane), thereby obtaining 2.1 g of an amorphous solid product.

Next, 1.27 g of the thus-obtained amorphous solid product was dissolved in 15 ml of diethyl ether. 2.8 ml of an n-hexane solution containing 4.5 mmol of n-butyl lithium (1.66 M) was dropped into the diethyl ether solution at −78° C. After completion of the dropping, the reaction solution was stirred for 12 hours while the temperature thereof was gradually raised to room temperature. After the reaction solution was stirred under a reduced pressure to remove the solvent, 5 ml of a mixed solvent of toluene and diethyl ether (40:1) was added thereto. After cooling to −78° C., the reaction solution was mixed with 0.53 (2.3 mmol) g of zirconium tetrachloride and the temperature thereof was immediately raised to room temperature, followed by stirring at room temperature for 4 hours. The obtained reaction solution was filtered through celite to separate a solid component therefrom. The thus-obtained solid component was washed with 3 ml of toluene to recover a solid reaction product. The recovered solid reaction product was extracted with dichloromethane. The extract was stirred under a reduced pressure to remove the solvent, thereby obtaining 906 mg of a racemic and meso mixture of dimethylsilylene bis[{1,1'-(2-methyl-4-(4-chlorophenyl-4-hydroazulenyl}] zirconium dichloride (yield: 56%).

The chemical shifts of $^1$H-NMR of the above-obtained racemic and meso mixture are as follows.

300 MHz, C$_6$D$_6$ (ppm) 0.45 (s, meso SiMe), 0.50 (s, racemic SiMe), 0.57 (s, meso SiMe), 1.88 (s, meso 2-Me), 1.96 (s, racemic 2-Me), 5.17 (br s, racemic 4-H), 5.22 (br s, meso 4-H), 5.6–6.1 (m, —CH=), 6.65–6.8 (m, —CH=), 7.1–7.40 (m, —CH=)

(b) Purification of Racemic Compound:

Further, 900 mg of the above-produced racemic and meso mixture was dissolved in 20 ml of dichloromethane and irradiated with light for 40 minutes by a 100 W high-pressure mercury vapor lamp to enhance a percentage of the racemic compound in the mixture. Thereafter, insoluble components were removed from the solution by filtration, and then the recovered filtrate was concentrated, dried and solidified. Next, the thus-obtained solid component was mixed with 22 ml of toluene while stirring and then allowed to stand, followed by removing the supernatant therefrom. Such purifying operations were repeated four times, and the obtained solid residue was dried to obtain 275 mg of a racemic compound of dimethylsilylene bis[{1,1'-(2-methyl-4-(4-chlorophenyl)-4-hydroazulenyl}] zirconium dichloride.

The chemical shifts of $^1$H-NMR of the above-obtained racemic compound are as follows.

300 MHz, CDCl$_3$ (ppm) 0.95 (s, 6H, SiMe), 2.13 (s, 6H, 2-Me), 4.82–4.85 (br d, 2H), 5.70–5.78 (m, 2H), 5.83–5.92 (m, 4H), 6.03–6.12 (m, 2H), 6.70 (d, J=12 Hz, 2H), 7.1–7.35 (m, 8H, —CH=)

(2) Polymerization of Propylene Using Methylalumoxane as Co-Catalyst:

4 mmol (calculated as Al atom) of triethylaluminum ("MMAO", produced by TOSOH AKZO CORP.) and 0.29 mg of the above-obtained racemic compound were charged into a 2-liter stirring-type autoclave. Further, the autoclave was charged with 1,500 ml of propylene. The content of the autoclave was heated to 70° C. to conduct the polymerization of propylene for one hour, thereby obtaining 72 g of polypropylene. As a result of the measurements, it was confirmed that the complex activity was $24.9 \times 10^4$, and the obtained polypropylene had a melting point (Tm) of 150.4° C., a melt flow rate (MFR) of 1.1, a weight-average molecular weight (Mw) of $3.6 \times 10^5$ and a Q-value (Mw/Mn) of 3.0.

Example 13

<Polymerization of Propylene Using Clay Minerals as Co-Catalyst>

(1) Chemical Treatment of Clay Minerals and Preparation of Solid Catalyst Component;

The same procedure as defined in Example 11(2) was conducted to obtain a montmorillonite/toluene slurry containing montmorillonite in an amount of 33 mg/ml.

(2) Polymerization of Propylene:

0.25 mmol (calculated as Al atom) of triisobutylaluminum (produced by TOSOH AKZO CORP.) was charged into a 1-liter stirring-type autoclave. Separately, 1.09 mg of the racemic compound obtained in Example 12(1) was diluted with toluene, and then charged into a catalyst feeder equipped with a safety rupture disc. Further, the above-prepared slurry containing 50 mg of montmorillonite and 0.15 mmol (calculated as Al atom) of triisobutylaluminum were charged into the autoclave. Thereafter, 700 ml of propylene was introduced into the autoclave and the safety rupture disc of the catalyst feeder was broken at room temperature. After the content of the autoclave was heated to 80° C., the polymerization of propylene was conducted at that temperature for one hour, thereby obtaining 131.3 g of polypropylene. As a result of the measurements, it was confirmed that the catalyst activity was 3,000 and the complex activity was $13.5 \times 10^4$, and the obtained polypropylene had a melting point (Tm) of 149.2° C., a melt flow rate (MFR) of 5.8, a weight-average molecular weight (Mw) of $2.4 \times 10^5$ and a Q-value (Mw/Mn) of 2.5.

Example 14

(1) Synthesis of dimethylsilylene bis[1,1'-{2-methyl-4-(4-trifluoromethylphenyl)-4-hydroazulenyl}] zirconium dichloride:

The same procedure as defined in Example 12(1)(a) was conducted except that 1.35 g of 1-bromo-4-trifluoromethyl benzene was used instead of 1.15 g of 1-bromo-4-chlorobenzene in Example 12(1)(a), to obtain 1.16 g of an amorphous solid product.

Using the above-produced amorphous solid product, 2.2 ml of an n-hexane solution of n-butyl lithium (1.66M) and 0.42 g (1.8 mmol) of zirconium tetrachloride, the same procedure as defined in Example 12(1)(a) was conducted, thereby obtaining 0.36 g of a yellow solid product. As a result of $^1$H-NMR analysis, the yellow solid product was identified to be a racemic and meso mixture of dimethylsilylene bis[1,1'-(2-methyl-4-(4-trifluoromethyl phenyl)-4-hydroazulenyl}] zirconium dichloride. The yield of the product was 15%.

(2) Polymerization of Propylene Using Methylalumoxane as Co-Catalyst:

4 mmol (calculated as Al atom) of methylalumoxane ("MMAO" produced by TOSOH AKZO CORP.) and 0.6 mg of the above-produced racemic and meso mixture were charged into a 2-liter stirring-type autoclave. Further, 1,500 ml of propylene was introduced into the autoclave. After the content of the autoclave was heated to 70° C., the polymerization of propylene was conducted at that temperature for one hour, thereby obtaining 50 g of polypropylene. As a result of the measurements, it was confirmed that the complex activity was $8.3 \times 10^4$, and the obtained polypropylene had a melting point (Tm) of 153.2° C. and a melt flow rate (MFR) of 1.0.

Example 15

(1) Synthesis of dimethylsilylene bis[1,1'-{2-methyl-4-(4-fluorophenyl)-4-hydroazulenyl}] zirconium dichloride:

(a) Synthesis of Racemic and Meso Mixture:

10 ml of a pentane solution containing 16.4 mmol of t-butyl lithium (1.64 M) was dropped into a solution prepared by dissolving 0.90 ml (8.2 mmol) of 1-bromo-4-chlorobenzene in a mixed solvent composed of 10 ml of n-hexane and 10 ml of diethyl ether, at −78° C. The obtained solution was stirred at −78° C. for 15 minutes, and then at −10° C. for 45 minutes. Thereafter, the solution was mixed with 1.05 g (7.37 mmol) of 2-methyl azulene to react these components with each other. The resultant reaction solution was stirred for one hour while the temperature thereof was gradually raised to room temperature. Thereafter, the reaction solution was cooled to 0° C., and mixed with 10 ml of tetrahydrofuran. Further, the reaction solution was mixed with 16 μl (0.20 mmol) of 1-methylimidazole and 0.45 ml (3.7 mmol) of dichlorodimethyl silane. After the reaction solution was stirred at room temperature for one hour, dilute hydrochloric acid was added thereto to terminate the reaction. The solution was separated into organic and aqueous phases, and the thus-separated organic phase was concentrated under a reduced pressure and dried with magnesium sulfate. The dried product was stirred under a reduced pressure to remove the solvent remaining therein. The thus-obtained product was purified by a silica gel column chromatography (a mixed solvent: dichloromethane and n-hexane), thereby obtaining 2.1 g of an amorphous solid product.

Next, 1.55 g of the thus-obtained amorphous solid product was dissolved in 15 ml of diethyl ether. 3.5 ml of an n-hexane solution containing 5.8 mmol of n-butyl lithium (1.66 M) was dropped into the diethyl ether solution at −78° C. After completion of the dropping, the reaction solution was stirred for 12 hours while the temperature thereof was gradually raised to room temperature. After the reaction solution was stirred under a reduced pressure to remove the solvent, 6 ml of a mixed solvent of toluene and diethyl ether (40:1) were added thereto. After cooling to −78° C., the solution was further mixed with 0.68 g (2.9 mmol) of zirconium tetrachloride and the temperature thereof was immediately raised to room temperature, followed by stirring at room temperature for 4 hours. The obtained reaction solution was mixed with 30 ml of dichloromethane and filtered through celite. 25 ml of n-hexane was added to the obtained filtrate, thereby obtaining, as a deposited product, 1.0 g of a racemic and meso mixture of dimethylsilylene bis{1,1'-(2-methyl-4-(4-fluorophenyl-4-hydroazulenyl}] zirconium dichloride (yield: 50%).

The chemical shifts of $^1$H-NMR of the above-obtained racemic and meso mixture are as follows.

300 MHz, $C_6D_6$ (ppm) 0.45 (s, meso SiMe), 0.51 (s, racemic SiMe), 0.58 (s, meso SiMe), 1.89 (s, meso 2-Me), 1.97 (s, racemic 2-Me), 5.20 (br s, racemic 4-H), 5.28 (br s, meso 4-H), 5.6–6.2 (m, —CH=), 6.75–7.4 (m, —CH=)

(b) Purification of Racemic Compound:

Next, 333 mg of the above-produced racemic and meso mixture was suspended in 20 ml of dichloromethane and irradiated for 10 minutes by a 100 W high-pressure mercury vapor lamp to enhance a percentage of the racemic compound in the mixture. Thereafter, insoluble components were removed from the solution by filtration, and the recovered filtrate was concentrated, dried and solidified. Next, the thus-obtained solid component was mixed with 4 ml of toluene while stirring and then allowed to stand, followed by removing the supernatant therefrom. Such purifying operations were repeated three times, and the obtained solid residue was washed two times with hexane and then dried, thereby obtaining 115 mg of a racemic compound of dimethylsilylene bis[1,1'-(2-methyl-4-(4-fluorophenyl)-4-hydroazulenyl}] zirconium dichloride.

The chemical shifts of $^1$H-NMR of the above-obtained racemic compound are as follows.

300 MHz, CDCl$_3$ (ppm) 0.95 (s, 6H, Si-Me), 2.14 (s, 6H, 2-Me), 4.84 (br, 2H, 4-H), 5.72–5.90 (m, 6H), 6.05–6.10 (m, 2H), 6.72 (d, J=12 Hz, 2H), 6.95–7.05 (m, 4H, —CH=), 7.32–7.40 (m, 4H, —CH=)

(2) Polymerization of Propylene Using Methylalumoxane as Co-Catalyst:

The same procedure as defined in Example 12(2) was conducted except that 0.29 mg of the racemic compound obtained in the above item (1) was used instead of the racemic compound obtained in Example 12(1), to obtain 30 g of polypropylene. As a result of the measurements, it was confirmed that the complex activity was 10.3×10$^4$, and the obtained polypropylene had a melting point (Tm) of 149.7° C., a melt flow rate (MFR) of 1.3, a weight-average molecular weight (Mw) of 3.4×10$^5$ and a Q-value (Mw/Mn) of 2.3.

Example 16

<Polymerization of Propylene Using Clay minerals as Co-Catalyst>

The same procedure as defined in Example 13(2) was conducted except that 1.035 mg of the racemic compound obtained in Example 15 was used instead of the racemic compound obtained in Example. 13(1), to obtain 154 g of polypropylene. As a result of the measurements, it was confirmed that the catalytic activity was 3080 and the complex activity was 14.2×10$^4$, and the obtained polypropylene had a melting point (Tm) of 148.0° C., a melt flow rate (MFR) of 6.9, a weight-average molecular weight (Mw) of 2.2×10$^5$ and a Q-value (Mw/Mn) of 2.4.

Example 17

(1) Synthesis of dimethylsilylene bis[1,1'-{2-methyl-4-(3-chlorophenyl)-4-hydroazulenyl}]hafnium dichloride:
(a) Synthesis of Racemic and Meso Mixture:

18.7 ml of a pentane solution containing 30.65 mmol of t-butyl lithium (1.64 M) was dropped into a solution prepared by dissolving 1.8 ml (15.32 mmol) of 1-bromo-3-chlorobenzene in a mixed solvent composed of 20 ml of n-hexane and 20 ml of diethyl ether, at −78° C. The resultant solution was stirred at −5° C. for 1 hour, and then mixed with 1.96 g (13.79 mmol) of 2-methylazulene to react these components with each other. The obtained reaction solution was stirred for 1.25 hours while the temperature thereof was gradually raised to room temperature. Thereafter, the reaction solution was cooled to 0° C., and mixed with 20 ml of tetrahydrofuran and 30 µl (0.38 mmol) of 1-methylimidazole and then with 0.84 ml (6.9 mmol) of dichlorodimethyl silane. After the reaction solution was stirred at room temperature for 1.5 hours, dilute hydrochloric acid was added thereto to terminate the reaction. The reaction solution was separated into organic and aqueous phases, and the organic phase was concentrated under a reduced pressure. After dichloromethane was added to the concentrated organic phase, the mixture was dried with magnesium sulfate and stirred under a reduced pressure to remove the solvent, thereby obtaining an amorphous crude reaction product.

Next, the thus-obtained amorphous crude reaction product was dissolved in 20 ml or dry diethyl ether. 8.6 ml of an n-hexane solution containing 13.8 mmol of n-butyl lithium (1.6 M) was dropped into the diethyl ether solution at −78° C. After completion of the dropping, the reaction solution was stirred for 12 hours while the temperature thereof was gradually raised to room temperature. After the reaction solution was stirred under a reduced pressure to remove the solvent, 15 ml of a mixed solvent of toluene and diethyl ether (40:1) was added thereto. After cooling to −78° C., the reaction solution was mixed with 2.2 g (6.9 mmol) of hafnium tetrachloride and the temperature thereof was immediately raised to room temperature, followed by stirring at room temperature for 5 hours. The obtained reaction solution was filtered through celite to separate a solid component therefrom. The thus-obtained solid component was washed with 5 ml of toluene and 4 ml of hexane to recover a solid reaction product. The recovered solid reaction product was extracted with 40 ml of dichloromethane. The extract was stirred under a reduced pressure to remove the solvent, thereby obtaining 571 mg of a racemic and meso mixture of dimethylsilylene bis[1,1'-(2-methyl-4-(3-chlorophenyl-4-hydroazulenyl}]hafnium dichloride (yield: 10%).

b) Purification of Racemic Compound:

Further, 571 mg of the above-produced racemic and meso mixture was dissolved in 15 ml of dichloromethane and irradiated with light for 15 minutes by a 100 W high-pressure mercury vapor lamp to enhance a percentage of the racemic compound in the mixture. Thereafter, insoluble components were removed from the solution by filtration, and then the recovered filtrate was concentrated, dried and solidified. Next, the thus-obtained solid component was mixed with 5 ml of toluene while stirring, followed by filtration of the resultant mixture through frit. The obtained solid residue was washed with 3 ml of toluene and 4 ml of hexane, and then dried under a reduced pressure, thereby obtain 290 mg of a racemic compound of dimethylsilylene bis[1,1'-(2-methyl-4-(3-chlorophenyl)-4-hydroazulenyl}] hafnium dichloride.

The chemical shifts of $^1$H-NMR of the above-obtained racemic compound are as follows.

300 MHz, CDCl$_3$ (ppm) 0.95 (s, 6H, SiMe), 2.22 (s, 6H, 2-Me), 4.93–4.97 (br d, 2H), 5.70–5.90 (m, 6H), 5.97–6.05 (m, 2H), 6.75 (d, 2H), 7.15–7.27 (m, 6H, arom), 7.33 (s, 2H, arom)

(2) Polymerization of Propylene Using Clay Minerals as Co-Catalyst:

The same procedure as defined in Example 13(2) was conducted except that 1.22 mg of the racemic compound obtained in the above item (1) was used instead of the racemic compound obtained in Example 12(1), to obtain 110 g of polypropylene. As a result of the measurements, it was confirmed that the complex activity was 9.0×10$^4$, the catalytic activity was 2200, and the obtained polypropylene had a melting point (Tm) of 152.4° C. and a melt flow rate (MFR) of 0.5.

Example 18

(1) Synthesis of dimethylsilylene bis[1,1-(2-methyl-4-(4-chlorophenyl)-4-hydroazulenyl)}hafnium dichloride:

29 ml of a pentane solution containing 47.0 mmol of t-butyl lithium (1.64 M) was dropped into a solution prepared by dissolving 4.5 g (23.53 mmol) of 1-bromo-4-chlorobenzene in a mixed solvent composed of 30 ml of n-hexane and 30 ml of diethyl ether, at −78° C. The resultant solution was stirred at −5° C. for 1.5 hours, and then mixed with 3.0 g (21.2 mmol) of 2-methyl azulene to react these components with each other. The reaction solution was stirred for 1 hour while the temperature thereof was gradually raised to room temperature.

Thereafter, the reaction solution was cooled to −5° C., and then mixed with 40 μl (0.47 mmol) of 1-methylimidazole and then with 1.28 ml (10.59 mmol) of dichlorodimethyl silane. After the reaction solution was stirred at room temperature for 1.5 hours, dilute hydrochloric acid was added thereto to terminate the reaction. The reaction solution was separated into organic and aqueous phases, and the organic phase was concentrated under a reduced pressure. After the solvent is removed, the obtained product was purified by a silica gel column chromatography (a mixed solvent: dichloromethane and n-hexane), thereby obtaining 2.74 g of an amorphous solid product.

Next, the thus-obtained reaction product was dissolved in 20 ml of dry diethyl ether. 6.3 ml of an n-hexane solution containing 9.72 mmol of n-butyl lithium (1.54 M) was dropped into the diethyl ether solution at −78° C. After completion of the dropping, the reaction solution was stirred for 12 hours while the temperature thereof was gradually raised to room temperature. Thereafter, the reaction solution was stirred under a reduced pressure to remove the solvent, and then mixed with 15 ml of a mixed solvent of dry toluene and dry diethyl ether (40:1). After cooling to −78° C., the reaction solution was mixed with 1.56 g (4.86 mmol) of hafnium tetrachloride and the temperature thereof was immediately raised to room temperature, followed by stirring at room temperature for 4 hours. The obtained reaction solution was filtered through celite to separate a solid component therefrom. The thus-obtained solid component was extracted with 90 ml of dichloromethane. The extract was subjected to distillation to remove the solvent therefrom, thereby obtaining 320 mg of a racemic compound of dimethylsilylene bis[1,1'-{2-methyl-4-(4-chlorophenyl)-4-hydroazulenyl}]hafnium dichloride (yield: 7%).

The chemical shifts of $^1$H-NMR of the above-obtained racemic compound are as follows.

300 MHz, $CDCl_3$ (ppm) δ 0.95 (s, 6H, $SiMe_2$), 2.21 (s, 6H, 2-Me), 4.92–4.96 (br d, 2H), 5.70–6.15 (m, 8H), 6.78 (d, 2H), 7.28 (s, 8H, arom)

(2) Polymerization of Propylene Using Methylalumoxane as Co-Catalyst:

<Polymerization of Propylene>

4 mmol (calculated as Al atom) of methylalumoxane ("MMAO" produced by TOSOH AKZO CORP.) and a toluene solution containing 0.65 mg of a racemic compound of dimethylsilylene bis[1,1'-(2-methyl-4-(4-chlorophenyl)-4-hydroazulenyl}] hafnium dichloride obtained in the above item (1) were charged into a 2-liter stirring-type autoclave. Further, 1,500 ml of propylene was introduced into the autoclave. The content of the autoclave was heated to 70° C., and the polymerization of propylene was conducted for one hour to obtain 8 g of polypropylene. As a result of the measurements, it was confirmed that the complex activity was $1.23 \times 10^4$, and the obtained polypropylene had a melting point (Tm) of 154.4° C., a melt flow rate (MFR) of 0.07, a weight-average molecular weight (Mw) of $14 \times 10^5$ and a Q-value (Mw/Mn) of 4.0.

Example 19
Polymerization of Propylene:

The same procedure as defined in Example 6(2) was conducted except that the racemic compound of dimethylsilylene bis[1,1'-{2-methyl-4-(4-chlorophenyl)-4-hydroazulenyl}] hafnium dichloride obtained in Example 18(1) was used as the component (A), to obtain 146 g of polypropylene. As a result of the measurements, it was confirmed that the catalytic activity was 2900, the complex activity was $12.0 \times 10^4$, and the obtained polypropylene had a melting point (Tm) of 150.6° C., a melt flow rate (MFR) of 0.4, a weight-average molecular weight (Mw) of $5.6 \times 10^5$ and a Q-value (Mw/Mn) of 3.1.

Example 20

(1) Chemical Treatment and Granulation of Clay Minerals:

3 Kg of commercially available montmorillonite ("KUNIPIA F" produced by KUNIMINE INDUSTRIES CO., LTD.) was pulverized by a vibrating mill and dispersed in 16 liters of 3% aqueous solution of sulfuric acid./The dispersion was mixed with 2.1 Kg of magnesium sulfate, followed by stirring at 90° C. for 3 hours. Thereafter, the dispersion was filtered to separate a solid component therefrom. The thus-obtained solid component was washed with water to adjust the pH thereof to not less than 5. Successively, after the solid content of the obtained slurry was adjusted to 15%, the slurry was sprayed by means of a spray drier to conduct granulation of the solid component. The thus-obtained particles were of a spherical shape.

10.0 g of the chemically treated montmorillonite obtained in the above was charged into a 200 ml flask and subjected to heating and desiccation treatment at 300° C. for 2 hours under a reduced pressure, thereby obtaining a component (B).

(2) Preparation of Solid Catalyst Component and Pre-Polymerization of Propylene:

400 ml of heptane was introduced into a 1-liter stirring-type autoclave and maintained at 40° C.

Separately, 10 g of the component (B) obtained in the above item (1) was dispersed in 40.2 ml of toluene. The dispersion was mixed with 79.8 ml of a dilute toluene solution containing triethylaluminum in an amount corresponding to 60 mmol. After these components were contacted with each other at room temperature for one hour, the supernatant was removed from the mixture, and the obtained solid residue was washed with toluene and then charged into the autoclave.

Next, 48.8 ml of a toluene solution containing dimethylsilylene bis[1,1'-{2-methyl-4-(4-chlorophenyl)-4-hydroazulenyl}] hafnium dichloride obtained in Example 18(1) in an amount corresponding to 0.10 mmol was charged into the autoclave. Further, 4.96 ml of a dilute toluene solution containing triisobutylaluminum in an amount corresponding to 4 mmol was dropped into the autoclave and then propylene was fed thereinto to initiate the polymerization (pre-polymerization) of propylene. The polymerization of propylene was continued for 15 minutes while maintaining the propylene pressure within the autoclave at 5 kgf/$cm^2$G. After completion of the polymerization, the polymerized slurry was taken out of the autoclave and the supernatant was removed therefrom to obtain a solid residue. The solid residue was dried at 40° C. for 3 hours under a reduced pressure, thereby obtaining a dry catalyst. The amount of the polymer obtained by the pre-polymerization was 3.1 g based on one gram of the component (B).

(3) Polymerization of Propylene:

0.4 g of triisobutylaluminum and 1.5 liters of propylene were charged into a 3-liter stirring-type autoclave. While maintaining the content of the autoclave at 30° C., 30 mg of the dry catalyst (as the amount of the component (B) except for the pre-polymerized product) obtained in the above item (2) was introduced under pressure into the autoclave. Next, the content of the autoclave was heated to 75° C. to conduct the polymerization of propylene for one hour. After completion of the polymerization, unreacted propylene was purged to recover polypropylene produced. The results are shown in Table 3.

Examples 21 and 22
<Polymerization of Propylene>

The same procedure as defined in Example 20(1)–(3) was conducted except that after introduction of the dry catalyst in Example 20(3), hydrogen was introduced into the autoclave in amounts shown in Table 3. The results are shown in Table 3.

Example 23
<Polymerization of Propylene>

The same procedure as defined in Example 20(1)–(3) was conducted except that the amount of the dry catalyst charged into the autoclave in Example 20(3) was changed to 15 mg (as the amount of the component (B) except for the pre-polymerized product). The results are shown in Table 3.

Example 24
<Random Copolymerization of Propylene and Ethylene>

The same procedure as defined in Example 20(1)–(3) was conducted except that the amount of the dry catalyst charged into the autoclave in Example 20(3) was changed to 15 mg (as the amount of the component (B) except for the pre-polymerized product), and further 1.5,liters of propylene and 45 g of ethylene were introduced into the autoclave. The results are shown in Table 3.

Examples 25 to 27

The same procedure as defined in Example 20(1)–(3) was conducted except that the respective conditions as defined in Example 20 were changed as follows. The results are shown in Table 3.
(1) Preparation of Solid Catalyst Component and Pre-Polymerization of Propylene:

The dry catalysts were prepared under the same conditions as defined in Example 20(2) except that compounds shown in Table 3 were used as the component (A).
(2) Polymerization of Propylene:

The polymerization of propylene was conducted under the same conditions as defined in Example 20(3) except that 50 mg of each of the dry catalysts (as the amount of the component (B) except for the pre-polymerized product) obtained in the above (1) was used.

Comparative Example 3
(1) Preparation of Solid Catalyst Component and Pre-Polymerization of Propylene:

The dry catalysts were prepared under the same conditions as defined in Example 20(2) except that 10 g of dimethylsilylene bis{1,1'-(2-methyl-4-phenylhydroazulenyl)}zirconium dichloride was used as the compound (A) and 10 g of methylalumoxane supported by silica carrier (MAO on $SiO_2$ by WITCO Co.,Ltd., Al atom content: 23 wt %) was used as the compound (B) instead of the chemical-treated clay mineral. The amount of the polymer obtained by the pre-polymerization was 2.8 g based on one gram of the MAO on $SiO_2$.

(2) Polymerization of Propylene:

The same procedure as defined in Example 20(3) was conducted except that the catalyst component prepared in the above item (1) was used instead of the catalyst used in Example 20(3). The results are shown in Table 3.

TABLE 3

| | Component (A) | Amount of solid catalyst component used (mg) | Component (C): triisobutyl aluminum (mg) | Amount of hydrogen supplied (ml) | Amount of ethylene supplied (g) |
|---|---|---|---|---|---|
| Ex. 20 | a | 30 | 400 | 0 | 0 |
| Ex. 21 | a | 30 | 400 | 42.5 | 0 |
| Ex. 22 | a | 30 | 400 | 136 | 0 |
| Ex. 23 | a | 15 | 400 | 0 | 0 |
| Ex. 24 | a | 15 | 400 | 0 | 45 |
| Ex. 25 | b | 50 | 400 | 0 | 0 |
| Ex. 26 | c | 50 | 400 | 0 | 0 |
| Ex. 27 | d | 50 | 400 | 0 | 0 |
| Comp. Ex. 3 | d | 50 | 400 | 0 | 0 |

| | Catalytic activity | Complex activity | Melting point (° C.) | MFR (g/10 min) |
|---|---|---|---|---|
| Example 20 | 1900 | 23.4 | 153.1 | 0.19 |
| Example 21 | 5600 | 68.9 | 153.7 | 1.87 |
| Example 22 | 9400 | 115.7 | 155.0 | 16.1 |
| Example 23 | 1600 | 19.7 | 154.0 | 0.076 |
| Example 24 | 9700 | 119.4 | 127.7 | 0.038 |
| Example 25 | 1430 | 19.7 | 149.3 | 4.6 |
| Example 26 | 3100 | 41.7 | 150.9 | 0.84 |
| Example 27 | 2020 | 30.8 | 147.7 | 6.2 |
| Comparative Example 3 | 710 | 10.8 | 146.7 | 7.6 |

| | Mw (×10⁵) | Q (Mw/Mn) | Bulk density (g/ml) |
|---|---|---|---|
| Example 20 | — | — | 0.38 |
| Example 21 | — | — | 0.38 |
| Example 22 | — | — | 0.41 |
| Example 23 | — | — | 0.39 |
| Example 24 | — | — | 0.38 |
| Example 25 | 3.2 | 3.4 | 0.48 |
| Example 26 | 5.8 | 3.9 | 0.48 |
| Example 27 | 2.8 | 3.0 | 0.47 |
| Comparative Example 3 | 2.5 | 2.8 | 0.37 |

Note:
a: dimethylsilylene bis[1,1'-{2-methyl-4-(4-chlorophenyl)-4-hydroazulenyl}] hafnium dichloride;
b: dimethylsilylene bis[1,1'-{2-methyl-4-(4-chlorophenyl)-4-hydroazulenyl}] zirconium dichloride;
c: dimethylsilylene bis[1,1'-(2-methyl-4-phenyl-4-hydroazulenyl)] hafnium dichloride;
d: dimethylsilylene bis[1,1'-(2-methyl-4-phenyl-4-hydroazulenyl)] zirconium dichloride;

Example 28
(1) Synthesis of dimethylsilylene bis{1,1'-(2-methyl-4-phenyl-7-isopropyl-4-hydroazulenyl}zirconium dichloride:

4.9 ml of a cyclohexane/diethyl ether solution containing 5.2 mmol of phenyl lithium (1.08 M) was dropped into 20 ml of a hexane solution containing 0.97 g (5.2 mmol) of 2-methyl-5-isopropylazulene, at 0° C. The resultant solution was stirred for 1 hour while the temperature thereof was gradually raised to room temperature. Thereafter, the reaction solution was cooled to 0° C., and mixed with 20 ml of tetrahydrofuran and 12 μl (0.15 mmol) of dimethylaminopyridine and then with 0.34 g (2.6 mmol) of dichlorodimethylsilane. After the reaction solution was stirred at room temperature for 2 hours, dilute hydrochloric acid was added thereto to terminate the reaction. The reaction solution was separated into organic and aqueous phases, and the organic phase was extracted with hexane, dried with magnesium sulfate and stirred under a reduced pressure to remove the solvent. The obtained product was purified by a silica gel column chromatography. (a mixed solvent: dichloromethane and n-hexane), thereby obtaining 1.4 g of dark green powder as a reaction product.

Next, 1.4 g of the thus-obtained reaction product was dissolved in 15 ml of diethyl ether. 3.2 ml of an n-hexane solution containing 4.9 mmol of n-butyl lithium (1.54 M) was dropped into the diethyl ether solution at −78° C. After completion of the dropping, the reaction solution was stirred for 2 hours while the temperature thereof was gradually raised to 0° C. After the reaction solution was stirred under a reduced pressure to remove the solvent, 23 ml of a mixed solvent of toluene and diethyl ether (20:1) was added thereto. After cooling to −78° C., the reaction solution was mixed with 0.57 g (2–4 mmol) of zirconium tetrachloride and the temperature thereof was immediately raised to 0° C., followed by stirring at 0° C. for one hour. Further, the temperature of reaction solution was raised to room temperature and stirred at room temperature for 6 hours. The obtained reaction solution was filtered through celite to separate a solid component therefrom. The thus-separated solid component was washed with 3 ml of toluene to recover a solid product. The recovered solid product was extracted with dichloromethane. The extract was stirred under a reduced pressure to remove the solvent, thereby obtaining 0.11 g of a racemic and meso mixture of dimethylsilylene bis{1,1'-(2-methyl-4-phenyl-7-isopropyl-4-hydroazulenyl)}zirconium dichloride (yield: 6%).

The chemical shifts of $^1$H-NMR of the above-obtained racemic and meso mixture are as follows.

300 MHz, $C_6D_6$ (ppm) 0.55 (s, meso SiMe), 0.57 (s, racemic SiMe), 0.60 (s, meso SiMe), 1.00 (d, iPr-Me), 1.12 (d, iPr-Me), 1.88 (s, 2-Me), 1.90 (s, 2-Me), 3.1 (m, iPr—CH), 5.26 (br s, 4-H), 5.28 (br s, 4-H), 5.7–5.9 (m, —CH=), 7.0–7.5 (m, —CH=)

(2) Polymerization of Propylene Using Methylalumoxane as Co-Catalyst:

4 mmol (calculated as Al atom) of methylalumoxane ("MMAO" produced by TOSOH AKZO CORP.) was charged into a 2-liter stirring-type autoclave. Separately, 0.3 mg of the above-produced racemic and meso mixture was diluted with toluene, and then charged into a catalyst feeder equipped with a safety rupture disc. Thereafter, 1,500 ml of propylene was introduced into the autoclave and the safety rupture disc of the catalyst feeder was broken at room temperature. After the content of the autoclave was heated to 70° C., the polymerization of propylene was conducted at that temperature for one hour, thereby obtaining 32 g of polypropylene. As a result of the measurements, it was confirmed that the complex activity was $1.1 \times 10^5$, and the obtained polypropylene had a melting point (Tm) of 152.6° C., a melt flow rate (MFR) of 1.4, a weight-average molecular weight (Mw) of $3.6 \times 10^5$ and a Q-value (Mw/Mn) of 3.5.

Example 29
<Polymerization of α-olefin Using Clay Minerals as Co-Catalyst>
(1) Chemical Treatment of Clay Minerals and Preparation of Solid Catalyst Component:

The same procedure as defined in Example 11(2) was conducted to obtain a montmorillonite/toluene slurry having a montmorillonite content of 33 mg/ml.

(2) Polymerization of Propylene:

0.5 mmol (calculated as Al atom) of triisobutylaluminum (produced by TOSOH AKZO CORP.) was charged into a 2-liter stirring-type autoclave. Separately, 1.8 mg of the racemic and meso mixture obtained in Example 28(1) was diluted with toluene, and then charged into a catalyst feeder equipped with a safety rupture disc. Further, the above-prepared slurry containing 100 mg of montmorillonite and 0.3 mmol (calculated as Al atom) of triisobutylaluminum were charged into the catalyst feeder. Thereafter, 1,500 ml of propylene was introduced into the autoclave and the safety rupture disc of the catalyst feeder was broken at room temperature. After the content of the autoclave was heated to 80° C., the polymerization of propylene was conducted at that temperature for one hour, thereby obtaining 37 g of polypropylene. As a result of the measurements, it was confirmed that the catalyst activity was 370, the complex activity was $2.1 \times 10^4$, and the obtained polypropylene had a melting point (Tm) of 146.0° C., a melt flow rate (MFR) of 143, a weight-average molecular weight (Mw) of $1.4 \times 10^5$ and a Q-value (Mw/Mn) of 2.2.

Example 30
(1) Synthesis of dimethylsilylene bis{1,1'-(2-ethyl-4-phenyl-7-isopropyl-4-hydroazulenyl)}zirconium dichloride:

7.2 ml of a cyclohexane/diethyl ether solution containing 7.8 mmol of phenyl lithium (1.08 M) was dropped into 20 ml of a hexane solution containing 1.54 g (7.8 mmol) of 2-ethyl-5-isopropyl azulene, at 0° C. The resultant solution was stirred for 1 hour while the temperature thereof was gradually raised to room temperature. Thereafter, the reaction solution was cooled to 0° C., and mixed with 20 ml of tetrahydrofuran and 12 μl (0.15 mmol) of dimethylaminopyridine and then with 0.50 g (3.9 mmol) of dichlorodimethylsilane. After the reaction solution was stirred at room temperature for 2 hours, dilute hydrochloric acid was added thereto to terminate the reaction. The reaction solution was separated into organic and aqueous phases, and the organic phase was extracted with hexane, dried with magnesium sulfate and stirred under a reduced pressure to remove the solvent, thereby obtaining 2.5 g of dark green powder as a reaction product.

Next, 2.5 g of the thus-obtained reaction product was dissolved in 30 ml of diethyl ether. 4.9 ml of an n-hexane solution containing 7–8 mmol of n-butyl lithium (1.59 M) was dropped into the diethyl ether solution at −78° C. After completion of the dropping, the reaction solution was stirred for 4 hours while the temperature thereof was gradually raised to room temperature. After the reaction solution was stirred under a reduced pressure to remove the solvent, 20 ml of a mixed solvent of toluene and diethyl ether (20:1) was added thereto. After cooling to −78° C., the reaction solution was mixed with 0.91 g (3.9 mmol) of zirconium tetrachloride and the temperature thereof was immediately raised to 0° C., followed by stirring at 0° C. for one hour. Further, the temperature of reaction solution was raised to room temperature and stirred at room temperature for 11 hours. The obtained reaction solution was filtered through celite to separate a solid component therefrom. The thus-obtained solid component was washed with 3 ml of toluene to recover a solid reaction product. The recovered solid reaction product was extracted with dichloromethane. The extract was stirred under a reduced pressure to remove the solvent, thereby obtaining 0.4 g of a racemic and meso mixture of dimethylsilylene bis{1,1'-(2-ethyl-4-phenyl-7-isopropyl-4-hydroazulenyl)}zirconium dichloride (yield: 7%).

The chemical shifts of $^1$H-NMR of the above-obtained racemic and meso mixture are as follows.

300 MHz, $C_6D_6$ (ppm) 0.58 (s, meso SiMe), 0.60 (s, racemic SiMe), 0.62 (s, meso SiMe), 1.1 (m, iPr-Me, Et-Me), 1.92 (q, Et-CH$_2$), 1.98 (q, Et-CH$_2$), 3.2 (m, iPr—

CH), 5.26 (br s, 4-H), 5.29 (br s, 4-H), 5.7–5.9 (m, —CH═), 7.0–7.5 (m, —CH═)

(2) Polymerization of Propylene Using Methylalumoxane as Co-Catalyst:

4 mmol (calculated as Al atom) of methylalumoxane ("MMAO" produced by TOSOH AKZO CORP.) was charged into a 2-liter stirring-type autoclave. Separately, 0.3 mg of the above-produced racemic and meso mixture was diluted with toluene, and then charged into a catalyst feeder equipped with a safety rupture disc. Thereafter, 1,500 ml of propylene was introduced into the autoclave and the safety rupture disc of the catalyst feeder was broken at room temperature. After the content of the autoclave was heated to 70° C., the polymerization of propylene was conducted at that temperature for one hour, thereby obtaining 52 g of polypropylene. As a result of the measurements, it was confirmed that the complex activity was $1.7 \times 10^5$, and the obtained polypropylene had a melting point (Tm) of 155.5° C., a melt flow rate (MFR) of 0.2, a weight-average molecular weight (Mw) of $5.3 \times 10^5$ and a Q-value (Mw/Mn) of 3.8.

Example 31

<Polymerization of Propylene Using Clay Minerals as Co-Catalyst>

0.25 mmol (calculated as Al atom) of triisobutylaluminum (produced by TOSOH AKZO CORP.) was charged into a 1-liter stirring-type autoclave. Separately, 0.8 mg of the racemic and meso mixture obtained in Example 30(1) was diluted with toluene, and then charged into a catalyst feeder equipped with a safety rupture disc. Further, 50 mg of the triethylaluminum-treated montmorillonite obtained in Example 29(1) and 0.15 mmol (calculated as Al atom) of triisobutylaluminum were charged into the catalyst feeder. Thereafter, 700 ml of propylene was introduced into the autoclave and the safety rupture disc of the catalyst feeder was broken at room temperature. After the content of the autoclave was heated to 80° C., the polymerization of propylene was conducted at that temperature for one hour, thereby obtaining 4 g of polypropylene. As a result of the measurements, it was confirmed that the catalyst activity was 76, the complex activity was $5.0 \times 10^3$, and the obtained polypropylene had a melting point (Tm) of 148.4° C., a weight-average molecular weight (Mw) of $1.5 \times 10^5$ and a Q-value (Mw/Mn) of 2.8.

Example 32

(1) Synthesis of dimethylsilylene bis{1,1'-(2-methyl-4-phenyl-6-isopropyl-4-hydroazulenyl)}zirconium dichloride as Component (A):

(a) Synthesis of 2-tosyl-4-isopropyltropolone:

10.2 g (62.3 mmol) of hinokitiol was dissolved in 20 ml of pyridine. 20 ml of a pyridine solution containing 12.1 g (63.5 mmol) of tosyl chloride was added to the above-prepared solution at room temperature. The resultant reaction solution was extracted with toluene. An organic phase of the extract was dried with magnesium sulfate, and then the solvent contained therein was removed under a reduced pressure, thereby obtaining 20.7 g of a mixture of 2-tosyl-4-isopropyltropolone and 2-tosyl-6-isopropyltropolone.

(b) Synthesis of 1-methoxy carbonyl-6-isopropylcycloheptafuran-2-one:

A sodium methoxide solution prepared from 100 ml of methanol and 2.1 g (94.3 mmol) of sodium was added to 100 ml of a methanol solution containing 17.6 g (55.5 mmol) of the mixture obtained in the above item (a) and 10.8 ml (94.3 mmol) of dimethyl malonate at 0° C. The mixed solution was stirred at 0° C. for one hour and then at room temperature overnight. After the solvent contained in the mixed solution was removed under a reduced pressure, the mixed solution was mixed with water and then extracted with a mixed solvent composed of hexane and ethyl acetate. An organic phase of the extract was dried with magnesium sulfate, and the solvent was removed under a reduced pressure, thereby obtaining 12.2 g of a crude product of 1-methoxycarbonyl-6-isopropylcycloheptafuran-2-one.

(c) Synthesis of 1-methoxycarbonyl-2-methyl-6-isopropylazulene:

600 ml of acetone and 200 ml of diethyl amine were added to 12.2 g of the above-obtained crude product of 1-methoxycarbonyl-6-isopropylcycloheptafuran-2-one. The mixture was subjected to intermittent reflux for 15 hours while heating. Thereafter, the solvent contained in the mixture was removed under a reduced pressure. The resultant crude product was purified by a column chromatography using a mixed solvent composed of hexane and ethyl acetate (5:1) as an eluent solvent, thereby obtaining 3.93 g of 1-methoxy arbonyl-2-methyl-6-isopropylazulene.

(d) Synthesis of 2-methyl -6-isopropylazulene:

70 ml of phosphoric acid was added to 3.93 g (16.2 mmol) of 1-methoxycarbonyl-2-methyl-6-isopropylazulene, and the mixture was heated at 100° C. for one hour. The resultant reaction solution-was added to 300 ml of an aqueous solution containing 30 g of sodium hydroxide and extracted with hexane. An organic phase of the extract was dried with magnesium sulfate, and the solvent remaining therein was removed under a reduced pressure. The obtained crude product was filtered through silica gel. Further, the solvent contained in the filtered solid component was removed, thereby obtaining 2.23 g of 2-methyl-6-isopropylazulene (yield: 75%).

(e) Synthesis of bis{1,1'-(2-methyl-4-phenyl-6-isopropyldihydroazulenyl)}dimethyl silane:

A diethyl ether/cyclohexane solution containing 12.1 mmol (1.0 N) of phenyl lithium was added to 40 ml of a hexane solution containing 2.08 g (11.3 mmol) of the above-produced 2-methyl-6-isopropylazulene at 0° C. The mixed solution was stirred at room temperature for 2 hours, and then mixed with 30 ml of tetrahydrofuran at −10° C. Further, 0.68 ml (5.64 mmol) of dichlorodimethylsilane was added to the mixed solution at −30° C., followed by stirring for one hour at room temperature and then for 2 hours at 45° C. After the mixed solution was allowed to stand at room temperature overnight, an ammonium chloride aqueous solution was added to the obtained reaction solution. After the reaction solution was separated into aqueous and organic phases and the organic phase separated was dried with magnesium sulfate, the solvent was removed under a reduced pressure. The obtained crude product was purified by a column chromatography using a mixed solvent composed of hexane and dichloromethane (10:1 to 5:1) as an eluent solvent, thereby obtaining 1.23 g of bis{1,1'-(2-methyl-4-phenyl-6-isopropyl-1,4-dihydroazulenyl)}dimethylsilane (yield: 38%).

(f) Synthesis of dimethylsilylene bis{1,1'-(2-methyl-4-phenyl-6-isopropyl-4-hydroazulenyl)}zirconium dichloride:

A hexane solution containing 4.55 mmol (1.63 N) of n-butyl lithium was added to 20 ml of a diethyl ether solution containing 1.2 g (2.07 mmol) of the above-produced bis{1,1'-(2-methyl-4-phenyl-6-isopropyl-1,4-dihydroazulenyl)}dimethylsilane at −78° C. After the mixed solution was stirred at room temperature overnight, the solvent contained in the obtained product was removed. The resultant product was washed with hexane, dried and solidified again. The obtained solid product was mixed with 20 ml of toluene and 0.5 ml of diethyl ether to form a solution. 434 mg (1.89 mmol) of zirconium tetrachloride was then added to the solution at −70° C.

The temperature of obtained reaction solution was gradually raised to room temperature and stirred at room temperature overnight. Thereafter, the reaction solution was filtered through celite, and the solvent contained in the separated solid component was removed under a reduced pressure. The solid component was dissolved again in 1 ml of dichloromethane and then mixed with 10 ml of hexane. At this time, no precipitate was formed. The obtained solution was dried and solidified under a reduced pressure, thereby obtaining 1.36 g of dimethylsilylene bis{1,1'-(2-methyl-4-phenyl-6-isopropyl-4-hydroazulenyl)}zirconium dichloride.
(2) Polymerization of Propylene:

The same procedure as defined in Example 1(4) was conducted except that the above-produced dimethylsilylene bis{1,1'-(2-methyl-4-phenyl-6-isopropyl-4-hydroazulenyl)}zirconium dichloride was used as the component (A), to obtain 120 g of polypropylene. As a result of the measurements, it was confirmed that the catalytic activity was 1200, the complex activity was $11.6 \times 10^4$, and the obtained polypropylene had a melting point (Tm) of 148.5° C., a melt flow rate (MFR) of 8.8, a weight-average molecular weight (Mw) of $2.4 \times 10^5$ and a Q-value (Mw/Mn) of 2.8.

Example 33
<Polymerization of Propylene Using Methylalumoxane as Co-Catalyst>

4 mmol (calculated as Al atom) of methylalumoxane ("MMAO" produced by TOSOH AKZO CORP.) and 1 mg of dimethylsilylene bis{1,1'-(2-methyl-4-phenyl-6-isopropyl-4-hydroazulenyl)}zirconium dichloride produced in Example 32(1) were diluted with toluene, and then charged into a 2-liter stirring-type autoclave. Thereafter, 1,500 ml of propylene was introduced into the autoclave. After the content of the autoclave was heated to 70° C., the polymerization of propylene was conducted at that temperature for one hour, thereby obtaining 70.4 g of polypropylene. As a result of the measurements, it was confirmed that the complex activity was $7.0 \times 10^4$, and the obtained polypropylene had a melting point (Tm) of 149.8° C., a melt flow rate (MFR) of 7.9, a weight-average molecular weight (Mw) of $2.6 \times 10^5$ and a Q-value (Mw/Mn) of 2.8.

Example 34
(1) Synthesis of dimethylsilylene bis{1,1'-(2-benzyl-4-phenyl-4-hydroazulenyl)}zirconium dichloride:

7.2 ml of a cyclohexane/diethyl ether solution containing 7.8 mmol of phenyl lithium (1.08 M) was dropped into 35 ml of a hexane solution containing 1.7 g (7.8 mmol) of 2-benzylazulene, at −5° C. The resultant solution was stirred for 2 hour while the temperature thereof was gradually raised to room temperature. Thereafter, the reaction solution was cooled to 0° C., and mixed with 35 ml of tetrahydrofuran and 0.016 g of 1-methylimidazole and then with 0.5 g (3.9 mmol) of dichlorodimethylsilane. After the reaction solution was stirred at room temperature for 1 hour, dilute hydrochloric acid was added thereto to terminate the reaction. The reaction solution was separated into organic and aqueous phases, and the organic phase was extracted with ether, dried with magnesium sulfate and stirred under a reduced pressure to remove the solvent. The obtained product was purified by a silica gel column chromatography (a mixed solvent: dichloromethane and n-hexane), thereby obtaining 1.5 g of dark green powder as a reaction product.

Next, 1.5 g of the thus-obtained reaction product was dissolved in 10 ml of diethyl ether. 2.9 ml of an n-hexane solution containing 46.4 mmol of n-butyl lithium (1.59 M) was dropped into the diethyl ether solution at −78° C. After completion of the dropping, the reaction solution was stirred for 4 hours while the temperature thereof was gradually raised to room temperature. After the reaction solution was stirred under a reduced pressure to remove the solvent, 15 ml of a mixed solvent of toluene and diethyl ether (40:1) was added thereto. After cooling to −78° C., the reaction solution was mixed with 0.54 g (23.2 mmol) of zirconium tetrachloride and the temperature thereof was immediately raised to room temperature, followed by stirring at room temperature for 12 hours. The obtained reaction solution was filtered through celite in the presence of a nitrogen stream to separate a solid component therefrom. The thus-obtained solid component was washed with toluene and stirred under a reduced pressure to remove the solvent, thereby obtaining 1.4 g of a racemic and meso mixture of dimethylsilylene bis{1,1'-(2-benzyl-4-phenyl-4-hydroazulenyl)}zirconium dichloride (yield: 74%).

The chemical shifts of $^1$H-NMR of the above-obtained racemic and meso mixture are as follows.

300 MHz, $C_6D_6$ (ppm) 0.83 (s, meso SiMe), 0.92 (s, racemic SiMe), 1.05 (meso SiMe), 3.75 (d, racemic benzyl $CH_2$), 3.90 (d, meso benzyl $CH_2$), 4.04 (d, racemic and meso benzyl $CH_2$), 4.99 (d, racemic 4-H), 5.06 (d, meso 4-H), 5.8–6.2 (m, —CH=), 6.8–7.6 (m, —CH=)
(2) Polymerization of Propylene Using Methylalumoxane as Co-Catalyst:

2 mmol (calculated as Al atom) of methylalumoxane ("MMAO" produced by TOSOH AKZO CORP.) was charged into a 1-liter stirring-type autoclave. Separately, 0.32 mg of the above-produced racemic and meso mixture was diluted with toluene, and then charged into a catalyst feeder equipped with a safety rupture disc. Thereafter, 700 ml of propylene was introduced into the autoclave and the safety rupture disc of the catalyst feeder was broken at room temperature. After the content of the autoclave was heated to 70° C., the polymerization of propylene was conducted at that temperature for one hour, thereby obtaining 10 g of polypropylene. As a result of the measurements, it was confirmed that the complex activity was $3.1 \times 10^4$, and the obtained polypropylene had a melting point (Tm) of 156.6° C., a melt flow rate (MFR) of 400, a weight-average molecular weight (Mw) of $0.8 \times 10^5$ and a Q-value (Mw/Mn) of 3.2.

Example 35
<Polymerization of Propylene Using Clay Minerals as Co-Catalyst>
(1) Chemical Treatment of Clay Minerals and Preparation of Solid Catalyst Component:

The same procedure as defined in Example 11(2) was conducted to obtain a montmorillonite/toluene slurry having a montmorillonite content of 33 mg/ml.
(2) Polymerization of Propylene:

0.25 mmol (calculated as Al atom) of triisobutylaluminum (produced by TOSOH AKZO CORP.) was charged into a 1-liter stirring-type autoclave. Separately, 2.4 mg of the racemic and meso mixture obtained in Example 34(1) was diluted with toluene, and then charged into a catalyst feeder equipped with a safety rupture disc. Further, the above-prepared toluene slurry containing 50 mg of montmorillonite and 0.15 mmol (calculated as Al atom) of triisobutylaluminum were charged into the catalyst feeder. Thereafter, 700 ml of propylene was introduced into the autoclave and the safety rupture disc of the catalyst feeder was broken at room temperature. After the content of the autoclave was heated to 80° C., the polymerization of propylene was conducted at that temperature for one hour, thereby obtaining 0.8 g of polypropylene. As a result of the measurements, it was confirmed that the catalyst activity was 16, the complex activity was 300, and the obtained polypropylene had a melting point (Tm) of 152.4° C., a weight-average molecular weight (Mw) of $0.5\times10^5$ and a Q-value (Mw/Mn) of 2.5.

Example 36

(1) Synthesis of dimethylsilylene bis{1,1'-(2-benzyl-4-phenyl-7-isopropyl-4-hydroazulenyl)}zirconium dichloride:

5.5 ml of a cyclohexane/diethyl ether solution containing 5.9 mmol of phenyl lithium (1.08 M) was dropped into 20 ml of a hexane solution containing 1.54 g (5.9 mmol) of 2-benzyl-5-isopropylazulene, at 0° C. The resultant solution was stirred for 1.5 hours while the temperature thereof was gradually raised to room temperature. Thereafter, the reaction solution was cooled to 0° C., and mixed with 20 ml of tetrahydrofuran and 11 µl (0.14 mmol) of dimethylaminopyridine and further with 0.36 g (3.0 mmol) of dichlorodimethylsilane. After the reaction solution was stirred for 3.5 hours while the temperature thereof was gradually raised to 10° C., dilute hydrochloric acid was added thereto to terminate the reaction. The reaction solution was separated into organic and aqueous phases, and the organic phase was extracted with hexane, dried with magnesium sulfate and stirred under a reduced pressure to remove the solvent. The obtained product was purified by a silica gel column chromatography (a mixed solvent: dichloromethane and n-hexane), thereby obtaining 1.7 g of dark green powder as a reaction product.

Next, 1.7 g of the thus-obtained reaction product was dissolved in 20 ml of diethyl ether. 2.9 ml of an n-hexane solution containing 4.7 mmol of n-butyl lithium (1.59 M) was dropped into the diethyl ether solution at –5° C. After completion of the dropping, the reaction solution was stirred for 3 hours while the temperature thereof was gradually raised to 10° C. After the reaction solution was stirred under a reduced pressure to remove the solvent, 12 ml of a mixed solvent of toluene and diethyl ether (20:1) was added thereto. After cooling to –78° C., the reaction solution was mixed with 0.55 g (2.4 mmol) of zirconium tetrachloride. Thereafter, the reaction solution was stirred for 4 hours while the temperature thereof was gradually raised to room temperature, followed by further stirring at room temperature for 11 hours. The obtained reaction solution was filtered through celite to separate a solid component therefrom. The thus-obtained solid component was washed with 3 ml of toluene to recover a solid product. The thus-recovered solid product was extracted with dichloromethane and then the extract was stirred under a reduced pressure to remove the solvent, thereby obtaining 0.23 g of a racemic and meso mixture of dimethylsilylene bis{1,1'-(2-benzyl-4-phenyl-7-isopropyl-4-hydroazulenyl)}zirconium dichloride (yield: 11%).

The chemical shifts of $^1$H-NMR of the above-obtained racemic and meso mixture are as follows.

300 MHz, $CDCl_3$ (ppm) 0.86 (s, meso SiMe), 0.90 (s, racemic SiMe), 0.96 (s, meso SiMe), 1.07 (d, iPr-Me), 1.16 (d, iPr-Me), 2.5 (m, iPr—CH), 3.7–4.0 (m, 2-$CH_2$), 4.85–5.00 (m, 4-H), 5.7–6.1 (m, —CH=), 6.4–7.5 (m, —CH=)

(2) Polymerization of Propylene Using Methylalumoxane as Co-Catalyst:

4 mmol (calculated as Al atom) of methylalumoxane ("MMAO" produced by TOSOH AKZO CORP.) was charged into a 2-liter stirring-type autoclave. Separately, 0.36 mg of the above-produced racemic and meso mixture was diluted with toluene, and then charged into a catalyst feeder equipped with a safety rupture disc. Thereafter, 1,500 ml of propylene was introduced into the autoclave and the safety rupture disc of the catalyst feeder was broken at room temperature. After the content of the autoclave was heated to 70° C., the polymerization of propylene was conducted at that temperature for one hour, thereby obtaining 25 g of polypropylene. As a result of the measurements, it was confirmed that the complex activity was $7.0\times10^4$, and the obtained polypropylene had a melting point (Tm) of 156.4° C., a melt flow rate (MFR) of 36, a weight-average molecular weight (Mw) of $1.6\times10^5$ and a Q-value (Mw/Mn) of 3.5.

Example 37

<Polymerization of Propylene Using Clay Minerals as Co-Catalyst>

0.25 mmol (calculated as Al atom) of triisobutylaluminum (produced by TOSOH AKZO CORP.) was charged into a 1-liter stirring-type autoclave. Separately, 1.8 mg of the racemic and meso mixture obtained in Example 36(1) was diluted with toluene, and then charged into a catalyst feeder equipped with a safety rupture disc. Further, 50 mg of the triethylaluminum-treated montmorillonite obtained in Example 35(1) and 0.15 mmol (calculated as Al atom) of triisobutylaluminum were charged into the catalyst feeder. Thereafter, 700 ml of propylene was introduced into the autoclave and the safety rupture disc of the catalyst feeder was broken at room temperature. After the content of the autoclave was heated to 80° C., the polymerization of propylene was conducted at that temperature for one hour, thereby obtaining 0.5 g of polypropylene. As a result of the measurements, it was confirmed that the catalyst activity was 1, the complex activity was 37, and the obtained polypropylene had a melting point (Tm) of 147.6° C.

Example 38

(1) Synthesis of 9-silafluorene-9,9-diyl bis{1,1'-(2-methyl-4-phenyl-4-hydroazulenyl)}zirconium dichloride:

5.2 ml of a cyclohexane/diethyl ether solution containing 5.6 mmol of phenyl lithium (1.08 M) was dropped into 10 ml of a hexane solution containing 0.8 g (5.6 mmol) of 2-methylazulene, at –5° C. The resultant solution was stirred for 2 hours while the temperature thereof was gradually raised to room temperature. Thereafter, the reaction solution was cooled to 0° C., and mixed with 10 ml of tetrahydrofuran and 0.017 g of dimethylaminopyridine and further with 0.7 g (2.8 mmol) of 9,9-dichloro-9-dimethylsilafluorene. After the reaction solution was stirred at room temperature for one hour, dilute hydrochloric acid was added thereto to terminate the reaction. The reaction solution was separated into organic and aqueous phases, and the aqueous phase was extracted with ether, the organic phases were combined, dried with magnesium sulfate and stirred under a reduced pressure to remove the solvent. The obtained product was purified by a silica gel column chromatography (a mixed solvent: dichloromethane and n-hexane), thereby obtaining 0.9 g of dark green powder as a reaction product.

Next, 0.9 g of the thus-obtained reaction product was dissolved in 6 ml of diethyl ether. 1.98 ml of an n-hexane solution containing 2.9 mmol of n-butyl lithium (1.47 M) was dropped into the diethyl ether solution at –78° C. After completion of the dropping, the reaction solution was stirred for 4 hours while the temperature thereof was gradually raised to room temperature. After the reaction solution was stirred under a reduced pressure to remove the solvent, 15 ml of a mixed solvent of toluene and diethyl ether (40:1) was added thereto. After cooling to –78° C., the reaction solution was mixed with 0.35 g (1.5 mmol) of zirconium tetrachloride. Thereafter, the reaction solution was the temperature thereof was immediately raised to room temperature, followed by further stirring at room temperature for 12 hours. The obtained reaction solution stirred under a reduced pressure to remove the solvent, and then mixed with toluene to form a suspension. The suspension was filtered through celite in the presence of a nitrogen stream to separate a solid component therefrom. The thus-obtained solid component was washed with toluene, and then extracted with dichloromethane. Thereafter, the extract was stirred under a reduced pressure to remove dichloromethane contained as a solvent therein, thereby obtaining 0.25 g of a racemic and meso mixture of 9-silafluorene-9,9-diyl bis{1,1'-(2-methyl-4-phenyl-4-hydroazulenyl)}zirconium dichloride (yield: 22%).

The chemical shifts of $^1$H-NMR of the above-obtained racemic and meso mixture are as follows.

300 MHz, CDCl$_3$ (ppm) 2.40 (s, meso 2-Me), 2.44 (s, racemic 2-Me), 5.01 (br s, racemic 4-H), 5.03 (br s, meso 4-H), 5.8–6.2 (m, —CH═), 7.1–7.7 (m, —CH═), 7.9–8.1 (m, —CH═), 8.3–8.5 (m, —CH═)

(2) Polymerization of Propylene Using Methylalumoxane as Co-Catalyst:

2 mmol (calculated as Al atom) of methylalumoxane ("MMAO" produced by TOSOH AKZO CORP.) was charged into a 1-liter stirring-type autoclave. Separately, 0.1 mg-of the above-produced racemic and meso mixture was diluted with toluene, and then charged into a catalyst feeder equipped with a safety rupture disc. Thereafter, 700 ml of propylene was introduced into the autoclave and the safety rupture disc of the catalyst feeder was broken at room temperature. After the content of the autoclave was heated to 70° C., the polymerization of propylene was conducted at that temperature for one hour, thereby obtaining 20 g of polypropylene. As a result of the measurements, it was confirmed that the complex activity was 20×10$^4$, and the obtained polypropylene had a melting point (Tm) of 152.8° C. and a melt flow rate (MFR) of 1.3.

Example 39
<Polymerization of Propylene Using Methylalumoxane as Co-Catalyst>

500 ml of toluene was charged into a 1-liter stirring-type autoclave. Successively, 2.1 mmol (calculated as Al atom) of methylalumoxane ("MMAO" produced by TOSOH AKZO CORP.) and 0.3 mg of the racemic and meso mixture obtained Example 38(1) were diluted with toluene, and then charged into the autoclave. Thereafter, propylene was introduced into the autoclave. After the content of the autoclave was heated to 70° C., the polymerization of propylene was conducted at that temperature for one hour while the propylene pressure in the autoclave was maintained at 5 kgf/cm$^2$G, thereby obtaining 4 g of polypropylene. As a result of the measurements, it was confirmed that the complex activity was 1.3×10$^4$, and the obtained polypropylene had a melting point (Tm) of 156.2° C.

Example 40
<Polymerization of Propylene Using Clay Minerals as Co-Catalyst>

(1) Chemical Treatment of Clay Minerals and Preparation of Solid Catalyst Component:

The same procedure as defined in Example 11(2) was conducted to obtain a montmorillonite/toluene slurry having a montmorillonite content of 33 mg/ml.

(2) Polymerization of Propylene:

0.25 mmol (calculated as Al atom) of triisobutylaluminum (produced by TOSOH AKZO CORP.) was charged into a 1-liter stirring-type autoclave. Separately, 3 mg of the racemic and meso mixture obtained in Example 38(1) was diluted with toluene, and then charged into a catalyst feeder equipped with a safety rupture disc. Further, the above-prepared toluene slurry containing 50 mg of montmorillonite and 0.15 mmol (calculated as Al atom) of triisobutylaluminum were charged into the catalyst feeder. Thereafter, 700 ml of propylene was introduced into the autoclave and the safety rupture disc of the catalyst feeder was broken at room temperature. After the content of the autoclave was heated to 80° C., the polymerization of propylene was conducted at that temperature for one hour, thereby obtaining 72 g of polypropylene. As a result of the measurements, it was confirmed that the catalyst activity was 1.4×10$^3$, the complex activity was 3.0×10$^4$, and the obtained polypropylene had a melting point (Tm) of 147.9° C. and a melt flow rate (MFR) of 21.3.

What is claimed is:

1. A catalyst component comprising a transition metal compound represented by the general formula (VI):

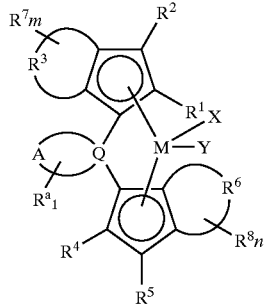

(VI)

wherein $R^1$, $R^2$, $R^4$ and $R^5$ are independently a hydrogen atom, a hydrocarbon group having 1 to 10 carbon atoms, a silicon-containing hydrocarbon group having 1 to 18 carbon atoms or a halogenated hydrocarbon group having 1 to 18 carbon atoms; $R^3$ and $R^6$ are independently a saturated or unsaturated divalent hydrocarbon group having 3 to 10 carbon atoms and forms a condensed ring in cooperation with 5-membered rings to which $R^3$ and $R^6$ are respectively bonded, with the proviso that at least one of $R^3$ and $R^6$ has 5 to 8 carbon atoms and forms a 7- to 10-membered condensed ring having at least one unsaturated bond derived from $R^3$ or $R^6$; $R^7$ and $R^8$ are independently a hydrocarbon group having 1 to 20 carbon atoms, an oxygen-containing hydrocarbon group having 1 to 20 carbon atoms, an amino group, a nitrogen-containing hydrocarbon group having 1 to 20 carbon atoms or a sulfur-containing hydrocarbon group having 1 to 20 carbon atoms; Q is a silicon atom, a germanium atom or a tin atom; A is a divalent unsaturated hydrocarbon group having 3 to 12 carbon atoms and forms a ring in cooperation with the Q to which A is bonded; $R^a$ is a saturated or unsaturated hydrocarbon group having 1 to 10 carbon atom; m and n are independently an integer of 0 to 20 with the proviso that m and n are not 0 at the same time, that when m or n is an integer of not less than 2, the $R^7$ or the $R^8$ may be bonded to each other to form a ring; l is an integer of 0 to 22, when l is an integer of not less than 2, the $R^a$ may be bonded to each other to form a ring; X and Y are independently a hydrogen atom, a halogen atom, a hydrocarbon group having 1 to 20 carbon atoms, a silicon-containing hydrocarbon group having 1 to 20 carbon atoms, a halogenated hydrocarbon group having 1 to 20 carbon atoms, an oxygen-containing hydrocarbon group having 1 to 20 carbon atoms, an amino group or a nitrogen-containing hydrocarbon group having 1 to 20 carbon atoms; and M is a transition metal selected from the group consisting of elements belonging to Group 4–6 of the Periodic Table.

2. The catalyst component according to claim 1, wherein M is an atom of zirconium or hafnium.

* * * * *